(12) United States Patent
Leonhardt

(10) Patent No.: US 11,110,274 B2
(45) Date of Patent: Sep. 7, 2021

(54) SYSTEM AND METHOD FOR TREATING INFLAMMATION

(71) Applicant: LEONHARDT VENTURES LLC, Corona Del Mar, CA (US)

(72) Inventor: Howard J. Leonhardt, Playa Vista, CA (US)

(73) Assignee: LEONHARDT VENTURES LLC, Corona Del Mar, CA (US)

( * ) Notice: Subject to any disclaimer, the term of this patent is extended or adjusted under 35 U.S.C. 154(b) by 215 days.

(21) Appl. No.: 16/137,467

(22) Filed: Sep. 20, 2018

(65) Prior Publication Data
US 2019/0022389 A1 Jan. 24, 2019

Related U.S. Application Data

(63) Continuation-in-part of application No. 15/812,760, filed on Nov. 14, 2017, now Pat. No. 10,960,206,
(Continued)

(51) Int. Cl.
*A61N 1/36* (2006.01)
*A61M 5/142* (2006.01)
(Continued)

(52) U.S. Cl.
CPC ...... *A61N 1/36031* (2017.08); *A61B 5/14546* (2013.01); *A61B 5/6803* (2013.01);
(Continued)

(58) Field of Classification Search
CPC ............ A61N 1/36031; A61N 1/36002; A61N 1/37205; A61N 1/3627; A61N 1/36139; A61N 1/3629; A61B 5/6803; A61B 5/14546; A61B 5/369; A61B 5/055; A61B 5/0533; A61B 5/4088; A61B 5/4082; A61B 5/026; A61B 5/14542; A61K 35/28; A61K 38/191; A61K 38/1841; A61K 38/204; A61K 38/2066; A61K 38/2006; A61K 38/195; A61K 38/18; A61M 2202/07; A61M 2205/05; A61M 2205/50;
(Continued)

(56) References Cited

U.S. PATENT DOCUMENTS 4,622,952 A 11/1986 Gordon
4,976,733 A 12/1990 Girardot
(Continued)

FOREIGN PATENT DOCUMENTS

CA 2685161 A1 10/2007
EP 0603451 A1 6/1994
(Continued)

OTHER PUBLICATIONS

Alghatrif et al. "The Conundrum of Arterial Stiffness, Elevated blood pressure, and Aging" Curr Hypertens Rep. Feb. 2015; 17(2): 12. doi: 10.1007/s11906-014-0523-z.
(Continued)

*Primary Examiner* — Mark W. Bockelman
(74) *Attorney, Agent, or Firm* — TraskBritt

(57) ABSTRACT

Described is a low voltage, pulsed electrical stimulation device for reducing inflammation in a subject, which can be useful in the treatment of concussions, traumatic brain injury, cancer, and so forth.

15 Claims, 21 Drawing Sheets

Related U.S. Application Data which is a continuation-in-part of application No. 15/460,129, filed on Mar. 15, 2017, now Pat. No. 10,646,644.

(60) Provisional application No. 62/308,702, filed on Mar. 15, 2016, provisional application No. 62/364,472, filed on Jul. 20, 2016, provisional application No. 62/375,271, filed on Aug. 15, 2016, provisional application No. 62/385,124, filed on Sep. 8, 2016, provisional application No. 62/454,521, filed on Feb. 3, 2017, provisional application No. 62/352,930, filed on Jun. 21, 2016, provisional application No. 62/363,012, filed on Jul. 15, 2016.

(51) Int. Cl.

| | | |
|---|---|---|
| *A61N 1/362* | (2006.01) | |
| *A61H 39/00* | (2006.01) | |
| *A61K 35/28* | (2015.01) | |
| *A61K 38/18* | (2006.01) | |
| *A61K 38/19* | (2006.01) | |
| *A61K 38/20* | (2006.01) | |
| *A61B 5/00* | (2006.01) | |
| *A61M 39/02* | (2006.01) | |
| *A61N 1/372* | (2006.01) | |
| *A61B 5/145* | (2006.01) | |
| *A61B 5/055* | (2006.01) | |
| *A61B 5/0533* | (2021.01) | |
| *A61M 39/00* | (2006.01) | |
| *A61B 5/026* | (2006.01) | |
| *A61B 5/369* | (2021.01) | |

(52) U.S. Cl.
CPC .......... *A61H 39/002* (2013.01); *A61K 35/28* (2013.01); *A61K 38/18* (2013.01); *A61K 38/1841* (2013.01); *A61K 38/191* (2013.01); *A61K 38/195* (2013.01); *A61K 38/204* (2013.01); *A61K 38/2006* (2013.01); *A61K 38/2066* (2013.01); *A61M 5/14276* (2013.01); *A61M 39/0208* (2013.01); *A61N 1/3627* (2013.01); *A61N 1/3629* (2017.08); *A61N 1/36139* (2013.01); *A61N 1/37205* (2013.01); *A61B 5/026* (2013.01); *A61B 5/055* (2013.01); *A61B 5/0533* (2013.01); *A61B 5/14542* (2013.01); *A61B 5/369* (2021.01); *A61B 5/4082* (2013.01); *A61B 5/4088* (2013.01); *A61H 2201/165* (2013.01); *A61M 2039/0036* (2013.01); *A61M 2202/07* (2013.01); *A61M 2205/05* (2013.01); *A61M 2205/50* (2013.01); *A61M 2205/502* (2013.01); *A61N 1/36002* (2017.08)

(58) Field of Classification Search
CPC .... A61M 2205/502; A61M 2039/0036; A61M 39/0208; A61M 5/14276; A61H 2201/165; A61H 39/002
See application file for complete search history.

(56) References Cited

U.S. PATENT DOCUMENTS

| | | | |
|---|---|---|---|
| 5,211,622 A | 5/1993 | Liboff et al. | |
| 5,543,318 A | 8/1996 | Smith et al. | |
| 5,693,029 A | 12/1997 | Leonhardt | |
| 5,713,917 A | 2/1998 | Leonhardt et al. | |
| 5,725,377 A | 3/1998 | Lemler et al. | |
| 5,817,139 A | 10/1998 | Kasano | |
| 5,957,949 A | 9/1999 | Leonhardt et al. | |
| 6,344,052 B1 | 2/2002 | Greenan et al. | |
| 6,618,625 B2 | 9/2003 | Silverstone | |
| 6,957,106 B2 | 10/2005 | Schuler et al. | |
| 6,988,004 B2 | 1/2006 | Kanno et al. | |
| 7,029,276 B2 | 4/2006 | Mao | |
| 7,136,699 B2 | 11/2006 | Palti | |
| 7,341,062 B2 | 3/2008 | Chachques et al. | |
| 7,483,749 B2 | 1/2009 | Leonhardt et al. | |
| 7,686,799 B2 | 3/2010 | Leonhardt et al. | |
| 7,881,784 B2 | 2/2011 | Pasricha et al. | |
| 8,133,267 B2 | 3/2012 | Leonhardt et al. | |
| 8,226,407 B2 | 7/2012 | Hanewinkel et al. | |
| 8,465,533 B2 | 6/2013 | Palti | |
| 8,639,361 B2 | 1/2014 | Nathanson | |
| 8,656,930 B2 | 2/2014 | Schuler et al. | |
| 8,660,669 B2 | 2/2014 | Nemeh et al. | |
| 8,738,144 B2 | 5/2014 | Schneider | |
| 8,909,346 B2 | 12/2014 | Chalmers | |
| 8,945,104 B2 | 2/2015 | Boone et al. | |
| 9,032,964 B2 | 5/2015 | Schuler | |
| 9,533,170 B2 | 1/2017 | Dye et al. | |
| 9,656,096 B2 | 5/2017 | Pilla | |
| 9,662,184 B2 | 5/2017 | Lowe | |
| 2002/0143373 A1 | 10/2002 | Courtnage et al. | |
| 2003/0032998 A1 | 2/2003 | Altman | |
| 2003/0220556 A1 | 11/2003 | Porat et al. | |
| 2004/0010231 A1 | 1/2004 | Leonhardt et al. | |
| 2004/0115587 A1 | 6/2004 | Breining et al. | |
| 2004/0147906 A1 | 7/2004 | Voyiazis et al. | |
| 2004/0236238 A1 | 11/2004 | Schuler et al. | |
| 2005/0171578 A1 | 8/2005 | Leonhardt | |
| 2006/0030908 A1 | 2/2006 | Powell et al. | |
| 2006/0100553 A1 | 5/2006 | Lodin | |
| 2007/0167984 A1 | 7/2007 | Kieval et al. | |
| 2007/0190028 A1 | 8/2007 | Qu et al. | |
| 2007/0265680 A1 | 11/2007 | Liu et al. | |
| 2008/0227046 A1 | 9/2008 | Lowe et al. | |
| 2008/0243060 A1 | 10/2008 | Hartmann et al. | |
| 2010/0082027 A1 | 4/2010 | Chalmers | |
| 2010/0184183 A1 | 7/2010 | Schussler et al. | |
| 2012/0156648 A1 | 6/2012 | Kaufman et al. | |
| 2013/0253413 A1 | 9/2013 | Levine et al. | |
| 2014/0023983 A1 | 1/2014 | Lowe et al. | |
| 2014/0214115 A1 | 7/2014 | Greiner et al. | |
| 2014/0214116 A1 | 7/2014 | Peterson et al. | |
| 2014/0214124 A1 | 7/2014 | Greiner et al. | |
| 2014/0214144 A1 | 7/2014 | Peterson et al. | |
| 2017/0028184 A1 | 2/2017 | Godden et al. | |
| 2017/0036032 A1 | 2/2017 | Schuler et al. | |
| 2017/0112983 A1 | 4/2017 | Thorne et al. | |
| 2017/0266371 A1 | 9/2017 | Leonhardt et al. | |
| 2017/0274206 A1 | 9/2017 | Leonhardt | |
| 2018/0064935 A1 | 3/2018 | Leonhardt et al. | |
| 2019/0015661 A1 | 1/2019 | Leonhardt et al. | |
| 2019/0022389 A1 | 1/2019 | Leonhardt | |
| 2019/0022396 A1 | 1/2019 | Leonhardt | |

FOREIGN PATENT DOCUMENTS

| | | |
|---|---|---|
| JP | 2013-034881 A | 2/2013 |
| KR | 10-2007-0010908 A | 1/2007 |
| KR | 10-0726825 B1 | 6/2007 |
| WO | 92/17118 A1 | 10/1992 |
| WO | 2006116728 A2 | 11/2006 |
| WO | 2007/146187 A2 | 12/2007 |
| WO | 2008/145724 A1 | 12/2008 |
| WO | 2009/021535 A1 | 2/2009 |
| WO | 2011/016629 A2 | 2/2011 |

OTHER PUBLICATIONS

Andersson et al. "Drinking, antidiuresis and milk ejection from electrical stimulation within the hypothalamus of the goat," Acta Physiol Scand. Dec. 31, 1955; 35(2):191-201; DOI: 10.1111/j.1748-1716.1955.tb01277.x.

Ando et al."RANKL/RANK/OPG: key therapeutic target in bone oncology" Curr Drug Discov Technol. Sep. 2008; 5(3): 263-268.

(56) References Cited

OTHER PUBLICATIONS

Aronowitz et al "Mechanical versus enzymatic isolation of stromal vascular fraction cells from adipose tissue" SpringerPlus (2015) 4:713 DOI 10.1186/s40064-015-1509-2.
Atkinson et al. "Bioelectric Properties of the Tooth" 1969 vol. 48 issue: 5, pp. 789-794.
Aubert et al. "A new ultrasonic process for a renewal of aortic valve decalcification" Cardiovascular Ultrasound 2006, 4:2 doi:10.1186/1476-7120-4-2.
Back et al. "Endogenous Calcification Inhibitors in the Prevention of Vascular Calcification: A Consensus Statement From the COST Action EuroSoftCalcNet" Frontiers in Cardiovascular Medicine | www.frontiersin.org, Jan. 2019 | vol. 5 | Article 196.
Bang et al., "Attenuation of Hypertension by C-Fiber Stimulation of the Human Median Nerve and the Concept-Based Novel Device," Scientific Reports, vol. 8, (2018), 12 pages.
Beitelshees et al "CXCL5 polymorphisms are associated with variable blood pressure in cardiovascular disease-free adults" Hum Genomics. 2012; 6(1): 9.
Berman "Suzanne Somers' Experimental Breast Reconstruction" Medpage Today, Feb. 7, 2012, www.medpagetoday.com > blogs > celebritydiagnosis.
Bi et al. "Key Triggers of Osteoclast-Related Diseases and Available Strategies for Targeted Therapies: A Review" Front Med (Lausanne). 2017; 4: 234. doi: 0.3389/fmed.2017.00234.
Boyle "Wound-Treating Jelly Regenerates Fresh, Scar-Free Skin", Popular Science, (Dec. 15, 2011), "New material developed for accelerated skin regeneration in major wounds", Science Highlight, (National Institute of Biomedical 11Imaging and Bioengineering, Dec. 17, 2015).
Brooks et al. "Bioelectric impedance predicts total body water, blood pressure, and heart rate during hemodialysis in children and adolescents" J. Ren Nutr., 18(3):304-311 (May 2008); doi: 10.1053/j.jm.2017.11.008.
Buckle et al. "Soluble Rank Ligand Produced by Myeloma Cells Causes Generalised Bone Loss in Multiple Myeloma" PLoS One. 2012; 7(8): e41127. doi: 10.1371/journal.pone.0041127 PMCID: PMC3430669.
CalXStars Business Accelerator, Inc.—Website—Justia Patents—Mar 15, 2017—US Patent Application for Stimulator, Pump & Composition Patent Application (Application #20170266371) https://protect-us.mimecast.com/s/tSaBCxkVIwuDr61CvMWbF?domain=patents.justia.com.
Chen et al. "Secreted Klotho Attenuates Inflammation-Associated Aortic Valve Fibrosis in Senescence-Accelerated Mice P1" Hypertension. 2018;71:877-885. DOI: 10.1161/Hypertensionaha.117. 10560.) Downloaded from http://ahajournals.org by on Apr. 24, 2020 (9 pages).
Chen et al., Efficacy and Safety of Acupuncture for Essential Hypertension: A Meta-Analysis, Medical Science Monitor, vol. 24, (2018), pp. 2946-2969.
Christouls et al. "Pathogenesis and Management of Myeloma Bone Disease" Expert Rev Hematol. 2009; 2(4):385-398.
Collins "Bioelectric Signals Can Be Used to Detect Early Cancer," Tufts News, http://now.tufts.edu/news-releases/bioelectric-signals-used-detect-early-cancer (Feb. 1, 2013).
Cowburn et al. "HIF isoforms in the skin differentially regulate systemic arterial pressure" Proc Natl Acad Sci U S A. Oct. 22, 2013; 110(43): 17570-17575.
Cross et al. "Milk Ejection following Electrical Stimulation of the Pituitary Stalk in Rabbits," Nature 166, 994-995 (Dec. 9, 1950); doi:10.1038/166994b0 (Abstract Only).
Dietrich et al. "Decalcification of the mitral annulus: surgical experience in 81 patients" Thorac Cardiovasc Surg. Oct. 2006;54(7):464-7 (Abstract Only).
El-Bialy et al "Effect of Low Intensity Pulsed Ultrasound (LIPUS) on Tooth Movement and Root Resorption: A Prospective Multi-Center Randomized Controlled Trial" J. Clin. Med. 2020, 9, 804; doi:10.3390/jcm9030804.

Eurekalert, UCI Study Finds Acupuncture Lowers Hypertension by Activating Natural Opioids, Available Online at < https://www.eurekalert.org/pub_releases/2016-10/uoc-usf103116.php >, (2016), 2 pages.
Fan et al., "A Review on the Nonpharmacological Therapy of Traditional Chinese Medicine with Antihypertensive Effects," Evidence-Based Complementary and Alternative Medicine, vol. 2019, (2019), Article ID 1317842, 7 pages.
Fatemi et al. "Imaging elastic properties of biological tissues by low-frequency harmonic vibration" Proceedings of the IEEE, 91(10):1503-1519 (Oct. 2003).
Fili et al. "Therapeutic implications of osteoprotegerin" Cancer Cell International vol. 9, Article No. 26 (2009).
Flachskampf et al., "Randomized Trial of Acupuncture to Lower Blood Pressure," Circulation, vol. 115, (2007), pp. 3121-3129.
Fonseca et al. "Electrical stimulation: Complementary therapy to improve the performance of grafts in bone defects?" Journal of Biomedical Materials Research Part B: Applied Biomaterials 2018 vol. 000b, Issue 0.
Goranov et al. "Bone Lesions in Multiple Myeloma—The OPG/RANK-ligand System" Folia Med (Plovdiv). 2004; 46(3): 5-11 (Abstract Only).
Goswami et al. "Osteoprotegerin rich tumor microenvironment: implications in breast cancer" Oncotarget. Jul. 5, 2016; 7(27): 42777-42791.
Greenwald "Pulse pressure and arterial elasticity" QJM: An International Journal of Medicine, vol. 95, Issue 2, 2002, pp. 107-112.
Guimaraes-Camboa et al. "Redox Paradox: Can Hypoxia Heal Ischemic Hearts?" Cell, 39(4):392-394, (Nov. 21, 2016) DOI: http://dx.doi.org/10.1016/j.devcel.2016.11.007.
Gurbax et al. "Accelerated Orthodontic Tooth Movement: A Review" mod Res Dent. 1(2). MRD.000508. 2017. DOI: 10.31031/MRD.2017.01.000508.
HealthCmi, "Acupuncture Combats Hypertension in University of California Research," Available online at < https://www.healthcmi.com/Acupuncture-Continuing-Education-News/1688-acupuncture-c . . . >, (2016), 9 pages.
HealthCMI, "Acupuncture Controls Hypertension in Groundbreaking Trial," Available online at < https://www.healthcmi.com/Acupuncture-Continuing-Education-News/1804-acupuncture-c . . . >, (2017), 9 pages.
HealthCMI, "UC Irvine—Acupuncture Reduces Hypertension Confirmed," Available Online at < https://www.healthcmi.com/Acupuncture-Continuing-Education-News/1792-uc-irvine-acup . . . >, (2017), 6 pages.
Heart Valve Calcifications—Focused Ultrasound TherapyFocused Ultrasound Therapy; Research Paper Last Updated: Jan. 28, 2020, The Focused Ultrasound Foundation Newsletter (5 pages).
Holen et al. "Role of Osteoprotegerin (OPG) in Cancer" Clin Sci (Lond). Mar. 2006; 110(3):279-91. doi: 10.1042/CS20050175.
Hu et al. "Klotho Deficiency Causes Vascular Calcification in Chronic Kidney Disease" J Am Soc Nephrol. Jan. 2011; 22(1): 124-136.
Hu et al. "Exosomes derived from human adipose mesenchymal stem cells accelerates cutaneous wound healing via optimizing the characteristics of fibroblasts", Nature Scientific Reports, vol. 6, Article No. 32993 (2016).
Huang et al. "Myocardial transfection of hypoxia-inducible factor-1a and co-transplantation of mesenchymal stem cells enhance cardiac repair in rats with experimental myocardial infarction", Stem Cell Research & Therapy 5:22 (2014) DOI: 10.1186/scrt410.
Hudson et al. "Local delivery of recombinant osteoprotegerin enhances postorthodontic tooth stability" Calcif Tissue Int. Apr. 2012; 90(4):330-42. doi: 10.1007/s00223-012-9579-4.
Iglesias-Linares et al. "The use of gene therapy vs. corticotomy surgery in accelerating orthodontic tooth movement." Orthod Craniofac Res. Aug. 2011; 14(3):138-48. doi: 10.1111/j.1601-6343.2011.01519.x.
Infante et al. "RANKL/RANK/OPG system beyond bone remodeling: involvement in breast cancer and clinical perspectives" Journal of Experimental & Clinical Cancer Research (2019) 38:12. https://doi.org/10.1186/s13046-018-1001-2.

(56) References Cited

OTHER PUBLICATIONS

International Search Report for International Application No. PCT/US19/52288, dated Jan. 10, 2020, 11 pages.
International Search Report for International Application No. PCT/US2019/025177, dated Sep. 3, 2019, 3 pages.
International Written Opinion for International Application No. PCT/US19/52288, dated Jan. 10, 2020, 07 pages.
International Written Opinion for International Application No. PCT/US2019/025177, dated Sep. 3, 2019, 5 pages.
Jouybar et al. "Enhanced Skin Regeneration by Herbal Extract-Coated Poly-L-Lactic Acid Nanofibrous Scaffold" Artif Organs. Nov. 2017; 41(11):E296-E307. doi: 10.1111/aor.12926 (Abstract Only).
Zupan et al. "The relationship between osteoclastogenic and anti-osteoclastogenic pro-inflammatory cytokines differs in human osteoporotic and osteoarthritic bone tissues," Journal of Biomedical Science, 2012, 19:28 (DOI: 10.1186/1423-0127-19-28).
Zhang et al. "Exosomes derived from human embryonic mesenchymal stem cells promote osteochondral regeneration", Osteoarthritis and Cartilage, vol. 24, Issue 12, Dec. 2016, pp. 2135-2140.
Yamakazi et al., "Hair cycle-dependent expression of hepatocyte growth factor (HGF) activator, other proteinases, and proteinase inhibitors correlates with the expression of HGF in rat hair follicles", J Investig Dermatol Symp Proc., 4(3):312-5 (Dec. 1999).
Yamaguchi, "RANK/RANKL/OPG during orthodontic tooth movement", Orthod Craniofac Res. May 2009; 12(2):113-9. doi: 10.1111/j.1601-6343.2009.01444.x.
What Is Elastin? http://www.keracyte.com/index.php/site/page?view=whatIsElastin.
Wei et al., "Epicardial FSTL1 reconstitution regenerates the adult mammalian heart," Nature 525: 479-485 (Sep. 24, 2015).
Walsh & Choi "Biology of the RANK* RAN* OPG System in Immunity, Bone, and Beyond", Front Immunol. 2014; 5: 511.
W. Hoffmann, "Regeneration of the gastric mucosa and its glands from stem cells", Curr Med Chem, 15(29):3133-44 (2008).
Thattaliyath et al. "Modified Skeletal Myoblast Therapy for Cardiac Failure Using AAV SDF-1," Proc. Inti. Soc. Mag. Reson. Med. 16, p. 579 (2008).
Tamaki et al., "Cardiomyocyte Formation by Skeletal Muscle-Derived Multi-Myogenic Stem Cells after Transplantation into Infarcted Myocardium", PLoS ONE 3(3): e1789.doi:10.1371/journal.pone.0001789 (Mar. 2008).
Stenn et al., "Bioengineering the Hair Follicle," Organogenesis, 3(1): 6-13 (Jan.-Mar. 2007).
Spadari et al., Electrical stimulation enhances tissue reorganization during orthodontic tooth movement in rats; Clinical Oral Investigations, Jan. 2017, vol. 21, Issue 1, pp. 111-120, Abstract.
Signature Orthodontics "Accelerated Tooth Movement", http://www.sigortho.com/accelerated-tooth-movement, visited Mar. 15 2017.
Seifi & Jeszri "Correlation of bone resorption induced by orthodontic tooth movement and expression of RANKL in rats", Dental Journal, vol. 26, No. 4 (2009).
Salcedo et al., "Low current electrical stimulation upregulates cytokine expression in the anal sphincter," Int. J. Colorectal Dis., Feb. 2012;27(2):221-5. doi: 10.1007/s00384-011-1324-3. Epub (Oct. 2011).
Sahoo and Losardo, "Exosomes and Cardiac Repair After Myocardial Infarction", Circulation Research, 114:333-344 (Jan. 16, 2014).
Robert Ferris, "Battle against baldness turns to stem cells" http://www.cnbc.com/2015/01/29/studies-indicate-its-possible-to-use-stem-cells-to-cure-baldness.html (Jan. 29, 2015).
Reversing Age-Related Hair Loss and Restoring Healthy Hair Growth in Men and Women https://nutritionreview.org/2015/08/reversing-age-related-hair-loss-and-restoring-healthy-hair-growth-in-men-and-women/ (Aug. 24, 2015).
R. Hamman "Modulation of RANKL and Osteoprotegerin in Adolescents Using Orthodontic Forces", Masters Thesis, University of Tennessee (2010).
Prochazka et al., "Cocktail of Factors from Fat-derived Stem Cells Shows Promise for Critical Limb Ischemia" http://www.sciencenewsline.com/news/2016012204520017.html (Jan. 21, 2016).
Prochazka et al. "Therapeutic Potential of Adipose-Derived Therapeutic Factor Concentrate for Treating Critical Limb Ischemia," Cell Transplantation, 25(9), pp. 1623-1633(11) (2016).
Park et al. "Effects of SM-215 on Hair Growth by Hair Follicle Stimulation", Indian Journal of Science and Technology, vol. 8(25), DOI: 10.17485/ijst/2015/v8i25/80263, (Oct. 2015).
P. Banerjee "Electrical muscle stimulation for chronic heart failure: an alternative tool for exercise training?" Curr Heart Fail Rep., 7(2):52-8. doi: 10.1007/s11897-010-0013-9 (Jun. 2010).
Our Approach to Improve Hair Loss by Increasing Hair Growth Factor IGF-1, http://www.jhgc.com.sg/theory/igf-1/index.html.
Otero et al. "Expression and Presence of OPG and RANKL mRNA and Protein in Human Periodontal Ligament with Orthodontic Force", Gene-Regulation-and-Systems-Biology, 2016, 10, 15-20.
Nimeri et al. "Acceleration of tooth movement during orthodontic treatment—a frontier in Orthodontics", Prog Orthod 2013; 14:42; DOI: 10.1186/2196-1042-14-42.
Mosteiro et al. "Tissue damage and senescence provide critical signals for cellular reprogramming in vivo." Science, 2016; 354 (6315): aaf4445 DOI: 10.1126/science.aaf4445.
Medtronic "Cardiac Resynchronization Therapy (CRT) Devices for Heart Failure" http://www.medtronic.com/us-en/patients/treatments-therapies/crt-devices.html.
Mass Device "Greatbatch wins FDA PMA for Algovita SCS" http://www.massdevice.com/greatbatch-wins-fda-pma-for-algovita-scs/ (Dec. 1, 2015).
Marie Ellis, "Cure for baldness? Stem cells bring hope" http://www.medicalnewstoday.com/articles/271898.php.
Li et al., "Exogenous IGF-1 promotes hair growth by stimulating cell proliferation and down regulating TGF-(Beta)1 in C57BL/6 mice in vivo" Growth Hormone & IGF Research, vol. 24, Issues 2-3, pp. 89-94 (Apr.-Jun. 2014).
Kim et al., The effects of electrical current from a micro-electrical device on tooth movement, http://e-kjo.org/search.php?where=aview&id=10.4041/kjod.2008.38.5.337& . . . visited Aug. 2, 2017.
Khan et al. "Accelerating Tooth Movement: What Options We Have?" J Dent Health Oral Disord Ther 2016, 5(7): 00181.
Keles et al. "Inhibition of tooth movement by osteoprotegerin vs. pamidronate under conditions of constant orthodontic force", Eur J Oral Sci. Apr. 2007;115(2):131-6.
Kaur et al. "Electrically conductive polymers and composites for biomedical applications", RSC Adv., 2015,5, 37553-37567 DOI: 10.1039/C5RA01851J.
Kanzaki et al. "Periodontal ligament cells under mechanical stress induce osteoclastogenesis by receptor activator of nuclear factor kappaB ligand up-regulation via prostaglandin E2 synthesis", J Bone Miner Res 2002;17:21 / 220.
Kanzaki et al. "Local RANKL gene transfer to the periodontal tissue accelerates orthodontic tooth movement", Gene Therapy, (2006) 13, 678-685.
Kanzaki et al. "Local OPG gene transfer to periodontal tissue inhibits orthodontic tooth movement." J Dent Res 2004;83:92/ 925.
Kanno et al., Establishment of a Simple and Practical Procedure Applicable to Therapeutic Angiogenesis, Circulation, 1999, pp. 2682-2687, vol. 99.
K. Hart, Katherine A.nn D.D.S., "RANKL and Osteoprotegerin Levels in Response to Orthodontic Forces" (2012). Theses and Dissertations (ETD). Paper 107. http://dx.doi.org/10.21007/etd.cghs.2012.0127.
Jia et al., "Activin B Promotes Initiation and Development of Hair Follicles in Mice" Cells Tissues Organs, 198:318-326 (Feb. 2014).
Jansen et al. "Stimulation of osteogenic differentiation in human osteoprogenitor cells by pulsed electromagnetic fields: an in vitro study" BMC Musculoskeletal Disorders (2010) 11:188 DOI: 10.1186/1471-2474-11-188.
Israeli innovation uses nerve stimulation to treat heart failure https://www.israel21c.org/israeli-innovation-uses-nerve-stimulation-to-treat-heart-failure/ (Feb. 11, 2007).

(56) References Cited

OTHER PUBLICATIONS

Involvement of hepatocyte growth factor/scatter factor and Met receptor signaling in hair follicle morphogenesis and cycling, FASEB J Feb. 2000 14:319-332.
Interesting study about prolactin, VEGF and angiogenic inhibition, http://www.regrowth.com/hair-loss-forums/topic/interesting-study-about-prolactin-vegf-and-angiogenic-inhibition/ (Nov. 2006).
Hy et al., "Insulin-like growth factor 1 and hair growth," Dermatol Online J,; 5(2):1 (Nov. 1999).
Hu Klein, "Vagus Nerve Stimulation: A new approach to reduce heart failure" Cardiology Journal (2010).
Hopkins Medicine "Overview of Pacemakers and Implantable Cardioverter Defibrillators (ICDs)," hopkinsmedicine.org/healthlibrary/conditions/cardiovascular_diseases/ )verview of pacemakers and implantable cardioverter defibrillators icds 85,P00234/, last visited Sep. 12, 2018.
Holding et al. "The correlation of RANK, RANKL and TNFa expression with bone loss volume and polyethylene wear debris around hip implants" Biomaterials 27(30):5212-9—Nov. 2006.
HN Sabbah "Electrical vagus nerve stimulation for the treatment of chronic heart failure", Cleve Clin J Med, 78 Suppl 1: S24-9. doi: 10.3949/ccjm.78.s1.04 (Aug. 2011).
Jung et al. "Prospective 1-Year Follow-Up Study of Breast Augmentation by Cell-Assisted Lipotransfer" Aesthetic Surgery Journal 2016, vol. 36(2) 179-190 © 2015 The American Society for Aesthetic Plastic Surgery, Inc.
Kido et al. "Hypoxia-Inducible Factor 1-Alpha Reduces Infarction and Attenuates Progression of Cardiac Dysfunction After Myocardial Infarction in the Mouse" JACC, vol. 46, Issue 11, Dec. 6, 2005, pp. 2116-2124. https://doi.org/10.1016/j.jacc.2005.08.045.
King et al. "Mechanical Decalcification of the Aortic Valve" 272 The Annals of Thoracic Surgery vol. 42 No. 3 Sep. 1986 (pp. 269-272).
Kondo et al. "Types of tooth movement, bodily or tipping, do not affect the displacement of the tooth's center of resistance but do affect the alveolar bone resorption" Angle Orthod Jul. 2017; 87(4):563-569.
Kose et al. "Citric acid as a decalcifying agent for the excised calcified human heart valves" Anadolu Kardiyol Derg 2008; 8: 94-8 (Eng Abstract).
Lamoureux et al. "Therapeutic Relevance of Osteoprotegerin Gene Therapy in Osteosarcoma: Blockade of the Vicious Cycle between Tumor Cell Proliferation and Bone Resorption" Cancer Res 1 2007 67(15):7308-7318; DOI: 10.1158/0008-5472.CAN-06-4130.
Landau et al. "Review: Proposed Methods to Improve the Survival of Adipose Tissue in Autologous Fat Grafting" Plast Reconstr Surg Glob Open. 2018;6(8):e1870. Published Aug. 3, 2018. doi:10.1097/GOX.0000000000001870.
Lei "Mechanisms and Reversal of Elastin Specific Medial Arterial Calcification" (2014). All Dissertations, Papei 1307, (available at https://tigerprints.clemson.edu/all_dissertations/1307), 214 pages.
Leonhardt "Leonhardt Adds HIF-1 Alpha to Estate of Bioelectric Controlled Release Regenerative Proteins" Press Release, Published Jun. 13, 2017.
Li "Regulation of Renal Oxygenation and Blood Pressure" Art. Virginia Commonwealth University, Richmond, VA, United States (Abstract).
Li et al., "Long-Lasting Reduction of Blood Pressure by Electroacupuncture in Patients with Hypertension: Randomized Controlled Trial," Medical Acupuncture, vol. 27, No. 4, (2015), pp. 253-266.
Li et al., "Repetitive Electroacupuncture Attenuates Cold-Induced Hypertension through Enkephalin in the Rostral Ventral Lateral Medulla," Scientific Reports, vol. 6, (2016), 10 pages.
Li et al., "The Mechanism of Acupuncture in Treating Essential Hypertension: A Narrative Review," International Journal of Hypertension, vol. 2019, (2019), Article ID 8676490, 10 pages.
Liang et al. "Therapeutic effect of low-intensity pulsed ultrasound on temporomandibular joint injury induced by chronic sleep deprivation in rats" Am J Transl Res. 2019; 11(6): 3328-3340.
Longhurst et al. "Evidence-based blood pressure reducing actions of electroacupuncture: mechanisms and clinical application" Sheng Li Xue Bao. Oct. 25, 2017; 69(5): 587-597.
Malakhov et al. "Assessment of Efficacy of Non-Invasive Peripheral Transcutaneous Electrical Nerve Stimulation for Correction of Blood Pressure in Patients With Arterial Hypertension" Journal of Hypertension: Jul. 2019—vol. 37—Issue—p. e88-e89 doi: 10.1097/01.hjh.0000570296.70620.44.
Martin "Historically significant events in the discovery of RANK/RANKL/OPG" World J Orthop. Oct. 18, 2013; 4(4): 186-197. doi: 10.5312/wjo.v4.i4.186.
McBride et al. "Aortic valve decalcification" J Thorac Cardiovasc Surg. Jul. 1990;100(1):36-42; discussion 42-3 (Abstract Only).
McGrath "OPG/RANKL/RANK Pathway as a Therapeutic Target in Cancer" Journal of Thoracic Oncology, Sep. 2011 6(9): 1468-1473.
Nordstorm "Electrical Stimulation Blood Pressure Treatment Devices Market to Set Astonishing Growth by 2026" Art. Apr. 4, 2019 Gator Ledger.
Norton et al. "Bioelectric Perturbations of Bone: Research Directions and Clinical Applications" Angle Orthod (1984) 54 (1): 73-87.
Novack "Inflammatory osteoclasts, a different breed of bone eaters?" Arthritis Rheumatol. Dec. 2016; 68(12): 2834-2836. doi: 10.1002/art.39835.
Oranger et al. "Cellular Mechanisms of Multiple Myeloma Bone Disease" Clinical and Developmental Immunology vol. 2013, Article ID 289458, 11 pages http://dx.doi.org/10.1155/2013/289458.
Oyajobi "Multiple myeloma/hypercalcemia" Arthritis Research & Therapy vol. 9, Article No. S4 (2007).
Pierce et al. "Collection and characterization of amniotic fluid from scheduled C-section deliveries," Cell Tissue Bank, DOI 10.1007/s10561-016-9572-7 (Springer, 2012) and is available from Irvine Scientific.
Price et al. "Mitral Valve Repair is Feasible Following Extensive Decalcification and Reconstruction of the Atrioventricular Groove" J Heart Valve Dis. Jan. 2015;24(1):46-52 (Abstract Only).
Rachner et al. "Prognostic Value of RANKL/OPG Serum Levels and Disseminated Tumor Cells in Nonmetastatic Breast Cancer" Clin Cancer Res Feb. 15, 2019 (25) (4) 1369-1378; DOI: 10.1158/1078-0432.CCR-18-2482.
Raje et al. "Role of the RANK/RANKL Pathway in Multiple Myeloma" Clin Cancer Res 2019 25(1):12-20; DOI: 10.1158/1078-0432.CCR-18/1537.
Sahmeddini et al., "Electro-Acupuncture Stimulation at Acupoints Reduced the Severity of Hypotension During Anesthesia in Patients Undergoing Liver Transplantation," Journal of Acupuncture and Meridian Studies, vol. 5, Issue 1, (2012), pp. 11-14.
Sethi et al. "Aortic stiffness: pathophysiology, clinical implications, and approach to treatment" Integr Blood Press Control. 2014; 7: 29-34.
Showkatbakhsh et al. "Effect of Intra-Canal Direct Current Electric Stimulation on Orthodontic Tooth Movement: An Experimental Study in Canines" Journal of Dental School 2016; 34(3): 157-67.
Showkatbakhsh et al. "The effect of pulsed electromagnetic fields on the acceleration of tooth movement." World J Orthod. 2010 Winter;11(4):e52-6.
Sisay et al. "The RANK/RANKL/OPG system in tumorigenesis and metastasis of cancer stem cell: potential targets for anticancer therapy" Onco Targets Ther. 2017; 10: 3801-3810.
Spiridonov et al. "Effect of Transcutaneous Electrical Stimulation of Nerves on Blood Pressure and Blood Content of Neuropeptide CGRP and Nitric Oxide in Hypertensive Rats with Metabolic Disturbances" Bull Exp Biol Med (Feb. 2019) 166: 436-437.
Sutherland et al. "Prolonged electrical stimulation of the nipples evokes intermittent milk ejection in the anaesthetised lactating rat," Exp Brain Res. 1987;66(1)29-34.
Tajima et al. "HIF-1alpha is necessary to support gluconeogenesis during liver regeneration" Biochem Biophys Res Commun. Oct. 2, 2009; 387(4):789-94. doi: 10.1016/j.bbrc.2009.07.115. Epub Jul. 28, 2009.
Tan et al. "Bioelectric Perturbations in Orthodontic tooth movement" 2010 Journal of Dental Sciences & Research 1:1: pp. 41-49.

(56) References Cited

OTHER PUBLICATIONS

Tan et al., "Acupuncture Therapy for Essential Hypertension: a Network Meta-Analysis," Annals of Translational Medicine, vol. 7, (2019), pp. 1-12.
Tavlasoglu et al. "Is partial decalcification of posterior mitral annular bed logical in all mitral valve replacement procedures?" European Journal of Cardio-Thoracic Surgery 43 (2013) 449-450.
Tokyo Medical and Dental University "RANKL expressed by osteocytes has an important role in orthodontic tooth movement" Science Daily Oct. 20, 2017.
Totsugawa, et al. "Ultrasonic annular debridement in minimally invasive aortic valve replacement" Gen Thorac Cardiovasc Surg. Jan. 2020;68(1):81-83. doi: 10.1007/s1511748-019-01158-8. Epub Jun. 15, 2019. (Abstract Only).
Ucirvine, "Electroacupuncture for Hypertension in Women: The Susan Samueli Center for Integrative Medicine at UC Irvine is Recruiting Patients for a Study", Principle Investigators: Dr. Stephanie Tjen-a-Looi and Dr. Shaista Malik, MOD# 20266, HS# 1999-2222, (2017), 1 page.
Valvublator Heart Valve Regeneration, accessed Apr. 24, 2020 https://valvublator.com (6 pages).
Van Dam et al. "RANK/RANKL signaling inhibition may improve the effectiveness of checkpoint blockade in cancer treatment" Critical Reviews in Oncology/Hematology vol. 133, Jan. 2019, pp. 85-91.
Verna et al. "The rate and the type of orthodontic tooth movement is influenced by bone turnover in a rat model" European Journal of Orthodontics 22 (2000) 343-352.
Vilela-Martin et al., "Effects of Transcutaneous Electrical Nerve Stimulation (TENS) on Arterial Stiffness and Blood Pressure in Resistant Hypertensive Individuals: Study Protocol for a Randomized Controlled Trial," Trials, vol. 17, (2016), pp. 1-13.
Wang et al. "Local and sustained miRNA delivery from an injectable hydrogel promotes cardiomyocyte proliferation and functional regeneration after ischemic injury", Nat Biomed Eng. 2017; 1: 983-992, doi: 10.1038/s41551-017-0157-y.
Warner "Inflammation Adds to Blood Pressure Risks, High Blood Pressure and C-Reactive Protein May Trigger Heart Attack, Stroke" Art. WebMD Health News (2003) 2 pages.
Welch "RGS2 Proteins Regulate Blood Pressure" JASN Nov. 2010, 21 (11) 1809-1810.
Yang "Effect RANKL Produced by Periodontal Ligament Cells on Orthodontic Tooth Movement" (2016) Dental Theses. Paper 13.
Hearts build new muscle with this simple protein patch, jacobsschool,ucsd.edu/news/news_ releases/release.sfe?id=1813 (Sep. 16, 2015).
Hair Growth Factors, Nanogen, http://www.svijet-kose.com/dokumenti/Serum-vegf.pdf.
Giganti et al. "Changes in serum levels of TNF-alpha, IL-6, OPG, RANKL and their correlation with radiographic and clinical assessment in fragility fractures and high energy fractures", J Biol Regul Homeost Agents, Oct.-Dec. 2012; 26 (4):671-80.
Fukuoka et al., "The Latest Advance in Hair Regeneration Therapy Using Proteins Secreted by Adipose-Derived Stem Cells" The American Journal of Cosmetic Surgery, 29(4):273-282 (2012).
Fukuoka and Suga, "Hair Regeneration Treatment Using Adipose-Derived Stem Cell Conditioned Medium: Follow-up With Trichograms" Eplasty, 15:e10 (Mar. 2015).
Elastatropin(Registered) in Scalp & Hair Conditioning https://www.proteingenomics.com/haircare.html.
Dong-Hwan Kim et al., The effects of electrical current from a micro-electrical device on tooth movement, Korean Orthod., Oct. 2008, 38(5):337-346.
Dibart et al. "Tissue response during Piezocision-assisted tooth movement: a histological study in rats", Eur J Orthod (2014) 36 (4): 457-464; DOI: https://doi.org/10.1093/ejo/cjt079.
D. Grad, "Electrical Scalp Device Can Slow Progression of Deadly Brain Tumors", New York Times, https://www.nytimes.com/2014/11/16/health/electrical-scalp-device-can-slow-progression-of-deadly-brain-tumors.html?_r=0 (Nov. 15, 2014).

D'Apuzzo et al. "Biomarkers of Periodontal Tissue Remodeling during Orthodontic Tooth Movement in Mice and Men: Overview and Clinical Relevance", The Scientific World Journal, vol. 2013 (2013), Article ID 105873, 8 pages, http://dx.doi.org/10.1155/2013/105873.
Control of pelage hair follicle development and cycling by complex interactions between follistatin and activin, FASEB J (Jan. 2, 2003).
Control of Hair Growth by a Growth Factor Protein, http://www.hairloss-reversible.com/control-of-hair-growth-by-a-growth-factor-protein/.
Columbia "Implant Procedure Concepts—Pacemaker, ICD and CRT Overview," columbia.edu/itc/hs/medical/hickey/docs/Pacemaker,%20ICD%20and%20CRT%20Overview%20022007.pdf, last risited Sep. 12, 2018.
Chen et al., "Regenerative Hair Waves in Aging Mice and Extra-Follicular Modulators Follistatin, Dkk1, and Sfrp4," Journal of Investigative Dermatology, Aug. 2014, vol. 134, Issue 8, pp. 2086-2096.
Chemet & Levin, "Transmembrane voltage potential is an essential cellular parameter for the detection and control of tumor development in a Xenopus model," Dis. Models & Mech. 6, pp. 595-607 (2013); doi:10.1242/dmm.010835.
Chang et al. Effect of Pulse-Burst Electromagnetic Field Stimulation on Osteoblast Cell Activities; Bioelectromagnetics 25:457-465 (2004).
Chang et al. "Pulsed electromagnetic fields stimulation affects osteoclast formation by modulation of osteoprotegerin, RANK ligand and macrophage colony-stimulating factor", Journal of Orthopaedic Research, 23 (2005) 1308-1314.
Cerrada et al. "Hypoxia—Inducible Factor 1 Alpha Contributes to Cardiac Healing in Mesenchymal Stem Cells-Mediated Cardiac Repair," Stem Cells and Development, 22(3): 501-511 (2013).
Bradshaw et al. "Designer self-assembling hydrogel scaffolds can impact skin cell proliferation and migration" Nature Scientific Reports, vol. 4, Article No. 6903 (2014).
Blood Vessels Hold Key to Thicker Hair Growth, https://www.sciencedaily.com/releases/2001/02/010215074636.htm(Feb. 2001).
Bio-Leonhardt "Micro Stimulator" http://www.bioleonhardt.com/micro-stimulator/.
Barbault et al., Amplitude-modulated electromagnetic fields for the treatment of cancer: Discovery of tumor-specific frequencies and assessment of a novel therapeutic approach, Journal of Experimental & Clinical Cancer Research, Apr. 14, 2009, vol. 28, No. 51, doi:10.1186/1756-9966-28-51, 10 pages.
B. Borgobello "FDA approves the treatment of brain tumors with electrical fields," New Atlas, http://newatlas.com/treatment-of-brain-tumors-with-electrical-fields/21433/(Feb. 13, 2012), last visited Sep. 12, 2018.
Almpani et al., "Nonsurgical Methods for the Acceleration of the Orthodontic Tooth Movement", Tooth Movement Fronl Oral Biol., vol. 18, pp. 80-91 (Karger, Basel, CH 2016) (DOI:10.1159/000382048), Published online: Nov. 24, 2015.
Alice Park, "Shrinking Stem Cells Are the Real Reason for Hair Loss" Time, (Feb. 5, 2016).
"FDA Approves Algovita Spinal Cord Stimulation System from Greatbatch,"http://www.odtmag.com/contents/view_breaking-news/2015-12-02/fda-approves-algovita-spinal-cord-stimulation-jystem-from-greatbatch (Dec. 2, 2015).
"Electrical brain stimulation could support stroke recovery," sciencedaily.com/releases/2016/03/160316151108.htm (Mar. 16, 2016), last visited Sep. 12, 2018.
"Electric Tumor Treatment Fields," No. 0827 Policy, aetna.com/cpb/medical/data/800_899/0827.html (Nov. 18, 2016), last visited Sep. 12, 2018.
Apuzzo et al. "Biomarkers of Periodontal Tissue Remodeling during Orthodontic Tooth Movement in Mice and Men: Overview and Clinical Relevance", The Scientific World Journal, vol. 2013 (2013), Article ID 105873, 8 pages, http://dx.doi.org/10.1155/2013/105873.
Yang et al., "Acupuncture for hypertension," Cochrane Database of Systematic Reviews, Available Online at < https://www.cochranelibrary.com/cdsr/doi/10.1002/14651858.CD008821.pub2/full >, (2018), 4 pages.

(56) References Cited

OTHER PUBLICATIONS

Yu et al. "Association between inflammation and systolic blood pressure in RA compared to patients without RA" Arthritis Research & Therapy vol. 20, Article No. 107 (2018).
Zaniboni et al. "Do electrical current and laser therapies improve bone remodeling during an orthodontic treatment with corticotomy?" Clin Oral Invest 23, 4083-4097 (2019). https://doi.org/10.1007/s00784-019-02845-9.
Zdzisinska et al. "RANK/RANKL i OPG w szpiczaku plazmocytowym [The role of RANK/RANKL and OPG in multiple myeloma]" Postepy Hig Med Dosw (Online). 2006; 60:471-482 (Abstract Only).
Zhao et al. "Local osteoprotegerin gene transfer inhibits relapse of orthodontic tooth movement." Am J Orthod Dentofacial Orthop. Jan. 2012; 141(1):30-40. doi: 10.1016/j.ajodo.2011.06.035.
Wagenseil et al., "Elastin in large artery stiffness and hypertension," Journal of Cardiovascular Translational Research, vol. 5, No. 3, 2012, pp. 264-273, Available online at < https://www.ncbi.nlm.nih.gov/pmc/articles/PMC3383658/ >, 21, pages.
Stein et al., "The effect of transcutaneous electrical nerve stimulation on blood pressure," Blood Pressure, vol. 22, Issue 3, 2013, available online at < https://www.tandfonline.com/doi/full/10.3109/08037051.2012.722271 >, 5 pages.
Schardong et al., "Intradialytic neuromuscular electrical stimulation reduces DNA damage in chronic kidney failure patients: a randomized controlled trial," Biomarkers, vol. 23, Issue 5, 2018, pp. 1-11.
Niiranen et al., "Relative Contributions of Arterial Stiffness and Hypertension to Cardiovascular Disease: The Framingham Heart Study," Journal of the American Heart Association, vol. 5, No. 11, 2016, 8 pages.
Leonhardt's Launchpads Announces Filing of Patent for Bioelectric Stimulation Controlled Klotho Expression—Powerful Anti-aging and Regeneration Promoting Protein, by API Podder, Published: Mar. 13, 2019, available online at < https://mysocialgoodnews.com/leonhardts-launchpads-announces-filing-of-patent-for-bioelectric-stimulation-controlled-klotho-expression-powerful-anti-aging-and-regeneration-promoting-protein/.
Almpani et al., "Nonsurgical Methods for the Acceleration of the Orthodontic Tooth Movement", Tooth Movement. Front Oral Biol., vol. 18, pp. 80-91 (Karger, Basel, CH 2016) (DOI:10.1159/000382048), Published online: Nov. 24, 2015.
Abstract of Zhang et al., "Comparison of arterial stiffness in non-hypertensive and hypertensive population of various age groups," Jan. 24, 2018, 2 pages.
Abstract of Sabino-Carvalho et al., "Non-invasive Vagus Nerve Stimulation Acutely Improves Blood Pressure Control in a Placebo Controlled Study," The FASEB Journal, vol. 31, 2017, available online at < https://www.fasebj.org/doi/abs/10.1096/fasebj.31.1_supplement.848.8 >, 2 pages.
Abstract of Collette et al., "Measurement of the local aortic stiffness by a non-invasive bioelectrical impedance technique," in Medical & Biological Engineering, vol. 49, No. 4, Feb. 2011, pp. 431-439, Available online at < https://www.ncbi.nlm.nih.gov/pubmed/21286830 >, 1 page
Sandvik et al., "Direct Electric Current Treatment under Physiologic Saline Conditions Kills *Staphylococcus epidermidis* Biofilms via Electrolytic Generation of Hypochlorous Acid," PloS one, vol. 8, (Feb. 2013), e55118, 14 pages.
Schmidt-Malan et al., "Activity of Fixed Direct Electrical Current in Experimental *Staphylococcus aureus* Foreign-Body Osteomyelitis," Diagnostic Microbiology and Infectious Disease, vol. 93, (2019), pp. 92-95.
Scott Jeffrey, "How to Decalcify Your Pineal Gland (and Why It's Really Important for Higher Mental Performance)," (available at https://scottjeffrey.com/decalcify-your-pineal-gland/), Retrieved on May 23, 2019, 23 pages.
Shahid et al., "Rhinosinusitis in Children," ISRN Otolaryngology, vol. 2012, Article ID 851831, (Dec. 2012), 11 pages.
Sharon M Moe, "Klotho: A Master Regulator of Cardiovascular Disease?," Circulation, vol. 125, (2012), pp. 2181-2183.
Shirtliff et al., "Assessment of the Ability of the Bioelectric Effect to Eliminate Mixed-Species Biofilms," Applied and Environmental Microbiology, vol. 71, (2005), pp. 6379-6382.
Shoji-Matsunaga et al. "Osteocyte regulation of orthodontic force-mediated tooth movement via RANKL expression." Scientific Reports, 7: 8753, published online Aug. 18, 2017, DOI:10.1038/s41598-017-09326-7.
Somayaji et al., "In Vitro Scanning Electron Microscopic Study on the Effect of Doxycycline and Vancomycin on Enterococcal Induced Biofilm," Iranian Endodontic Journal, vol. 5, (2010), pp. 53-58.
Souli et al., "Effects of Slime Produced by Clinical Isolates of Coagulase-Negative Staphylococci on Activities of Various Antimicrobial Agents," Antimicrobial Agents and Chemotherapy, vol. 42, (Apr. 1998), pp. 939-941.
Stewart et al., "Electrolytic Generation of Oxygen Partially Explains Electrical Enhancement of Tobramycin Efficacy Against Pseudomonas Aeruginosa Biofilm," Antimicrobial Agents and Chemotherapy, vol. 43, (1999), pp. 292-296.
Stoodley et al., "Influence of Electric Fields and pH on Biofilm Structure as Related to the Bioelectric Effect," Antimicrobial Agents and Chemotherapy, vol. 41, (1997), pp. 1876-1879.
Sultana et al., "Electrochemical Biofilm Control: A Review," Biofouling, vol. 31, (2015), pp. 745-758.
Szkotak et al., "Differential Gene Expression to Investigate the Effects of Low-Level Electrochemical Currents on Bacillus subtilis," AMB Express, vol. 1, (Nov. 2011), 12 pages.
Vinod Krishnan, Ze'ev Davidovitch (eds.), Biological Mechanisms of Tooth Movement, (John Wiley & Sons 2015 (10 Pages).
Wang et al., "Controlling *Streptococcus mutans* and *Staphylococcus aureus* Biofilms With Direct Current and Chlorhexidine," AMB Express, vol. 7, (Nov. 2017), 9 pages.
Wellman et al., "Bacterial Biofilms and the Bioelectric Effect," Antimicrobial Agents and Chemotherapy, vol. 40, (1996), pp. 2012-2014.
Wong et al., "Dual Functional Polyelectrolyte Multilayer Coatings for Implants: Permanent Microbicidal Base With Controlled Release of Therapeutic Agents," Journal of the American Chemical Society, vol. 132, (2010), pp. 17840-17848.
Wu et al., "Vascular Calcification: an Update on Mechanisms and Challenges in Treatment," Calcified Tissue International, vol. 93, (Oct. 2013), pp. 365-373.
Yang Lei, "Mechanisms and Reversal of Elastin Specific Medial Arterial Calcification" (2014). All Dissertations, Paper 1307, (available at https://tigerprints.clemson.edu/all_dissertations/1307), 214 pages.
Yarbrough et al., "Specific Binding and Mineralization of Calcified Surfaces by Small Peptides," Calcified Tissue International, vol. 86, (2010), pp. 58-66.
Zalavras, Charalampos G. "CORR Insights(Registered): Cathodic Voltage-Controlled Electrical Stimulation Plus Prolonged Vancomycin Reduce Bacterial Burden of a Titanium Implant-associated Infection in a Rodent Model," Clinical Orthopaedics and Related Research, vol. 474, (2016), pp. 1676-1678.
Zhang et al., "Highly Stable and Reusable Imprinted Artificial Antibody Used for in Situ Detection and Disinfection of Pathogens," Chemical Science, vol. 6, (2015), pp. 2822-2826.
Anne Trafton, "A Noninvasive Method for Deep Brain Stimulation," MIT News Office, (available at http://news.mit.edu/2017/noninvasive-method-deep-brain-stimulation-0601), (Jun. 01, 2017), 3 pages.
Aydin et al., "Focusing of Electromagnetic Waves by a Left-Handed Metamaterial Flat Lens," vol. 13, (2005), pp. 8753-8759.
Barker et al., "A Formidable Foe is Sabotaging Your Results: What You Should Know About Biofilms and Wound Healing," Plastic and Reconstructive Surgery, vol. 139, (2017), pp. 1184e-1194e.
Bioleohardnew, "Leonhardt Ventures Files Patent for Heart Valve Regeneration," (available at https://bioleonhardt.com/leonhardt-ventures-files-patent-for-heart-valve-regeneration/), (Mar. 20, 2018), 6 pages.
Borden et al., "Electric Current-Induced Detachment of *Staphylococcus epidermidis* Biofilms from Surgical Stainless Steel," Applied and Environmental Microbiology, vol. 70, (2004), pp. 6871-6874.

(56) References Cited

OTHER PUBLICATIONS

Cai et al., "Intermedin Inhibits Vascular Calcification by Increasing the Level of Matrix (Gamma)-Carboxyglutamic Acid Protein," Cardiovascular Research, vol. 85, (2010), pp. 864-873.
Canty et al., "Antibiotics Enhance Prevention and Eradication Efficacy of Cathodic-Voltage-Controlled Electrical Stimulation against Titanium-Associated Methicillin-Resistant *Staphylococcus aureus* and Pseudomonas aeruginosa Biofilms," mSphere, vol. 4, (May/Jun. 2019), e00178-19, 14 pages.
Caubet et al., "A Radio Frequency Electric Current Enhances Antibiotic Efficacy Against Bacterial Biofilms," Antimicrobial Agents and Chemotherapy, vol. 48, (2004), vol. 4662-4664.
Chen et al., "Deficiency in the Anti-Aging Gene Klotho Promotes Aortic Valve Fibrosis Through AMPK(Alpha)-Mediated Activation of RUNX2," Aging Cell, vol. 15, (Oct. 2016), pp. 853-860.
Chen et al., "The Role and Mechanism of (Alpha)-Klotho in the Calcification of Rat Aortic Vascular Smooth Muscle Cells," BioMed Research International, vol. 2015, (2015), 7 pages.
Chen et al., "The Strategy to Prevent and Regress the Vascular Calcification in Dialysis Patients," BioMed Research International, vol. 2017, (2017), 11 pages.
Chiang et al, "Silver-Palladium Surfaces Inhibit Biofilm Formation," Applied and Environmental Microbiology, vol. 75, (2009), pp. 1674-1678.
Costerton et al., "Mechanism of Electrical Enhancement of Efficacy of Antibiotics in Killing Biofilm Bacteria," Antimicrobial Agents and Chemotherapy, vol. 38, (1994), pp. 2803-2809.
Costerton et al., "The Application of Biofilm Science to the Study and Control of Chronic Bacterial Infections," The Journal of Clinical Investigation, vol. 112, (2003), pp. 1466-1477.
Delcaru et al., "Microbial Biofilms in Urinary Tract Infections and Prostatitis: Etiology, Pathogenicity, and Combating strategies," Pathogens, vol. 5, (2016), 12 pages.
Ehrlich et al., "Engineering Approaches for the Detection and Control of Orthopaedic Biofilm Infections," Clinical Orthopaedics and Related Research, vol. 437, (2005), pp. 59-66.
Froughreyhani et al, "Effect of Electric Currents on Antibacterial Effect of Chlorhexidine Against Entrococcus Faecalis Biofilm: an in Vitro Study," Journal of Clinical and Experimental Dentistry, vol. 10, (Dec. 2018), pp. e1223-e1229.
Giladi et al., "Microbial Growth Inhibition by Alternating Electric Fields," Antimicrobial Agents and Chemotherapy, vol. 52, (2008), pp. 3517-3522.
Golberg et al., "Eradication of Multidrug-Resistant A. Baumannii in Burn Wounds by Antiseptic Pulsed Electric Field," Technology, vol. 2, (2014), pp. 153-160.
Golberg et al., "Pulsed Electric Fields for Burn Wound Disinfection in a Murine Model," Journal of Burn Care & Research, vol. 36, (2015), pp. 7-13.
Hari et al., "Application of Bioelectric Effect to Reduce the Antibiotic Resistance of Subgingival Plaque Biofilm: An in Vitro Study," Journal of Indian Society of Periodontology, vol. 22, (2018), pp. 133-139.
Harkins et al., "Chitosan-Cellulose Composite for Wound Dressing Material. Part 2. Antimicrobial Activity, Blood Absorption Ability, and Biocompatibility," Journal of Biomedical Materials Research Part B, Applied biomaterials, vol. 102, (2014), 1199-1206.
Hleonhardt, Leonhardt Announces Vibrational Energy Device for Preventing Blood Clots Provisional Patent Application and License Agreements, (available at https://leonhardtventures.com/leonhardt-announces-vibrational-energy-device-preventing-blood-clots-provisional-patent-application-license-agreements/), (Jul. 5, 2017), 5 pages.
https://www.dicardiology.com/content/bioleonhardt-unveils-stem-pump Jan. 28, 2014.
Istanbullu et al., "Electrochemical Biofilm Control: Mechanism of Action," Biofouling, vol. 28, (2012), pp. 769-778.
Kasimanickam et al., "Prevention and Treatment of Biofilms by Hybrid- and Nanotechnologies," journal of Nanomedicine, vol. 8, (2013), pp. 2809-2819.

Kim et al., "Effect of Electrical Energy on the Efficacy of Biofilm Treatment Using the Bioelectric Effect," NPJ Biofilms and Microbiomes, vol. 1, (2015), Article 15016, 8 pages.
Kinney et al., "High Intensity Focused Electromagnetic Therapy Evaluated by Magnetic Resonance Imaging: Safety and Efficacy Study of a Dual Tissue Effect Based Non-Invasive Abdominal Body Shaping," Lasers in Surgery and Medicine, vol. 51, (2019), pp. 40-46.
Lasserre et al., "Influence of Low Direct Electric Currents and Chlorhexidine Upon Human Dental Biofilms," Clinical and Experimental Dental Research, vol. 2, (Jul. 2016), pp. 146-154.
Lasserre et al., "Oral Microbes, Biofilms and Their Role in Periodontal and Peri-Implant Diseases," Materials, vol. 11, (Sep. 2018), Article 1802, 17 pages.
Lee et al., "Hepatocyte growth factor (HGF) activator expressed in hair follicles is involved in in vitro HGF-dependent hair follicle elongation," J. Dermatol. Sci., 25(2):156-63 (Feb. 2001).
Lee et al., "Targeted Release of Tobramycin From a pH-Responsive Grafted Bilayer Challenged With *S. aureus*," Biomacromolecules, vol. 16, (2015), pp. 650-659.
Lei et al., "Efficacy of Reversal of Aortic Calcification by Chelating Agents," Calcified Tissue International, vol. 93, (Nov. 2013), 15 pages.
Leibrock et al, "NH4CI Treatment Prevents Tissue Calcification in Klotho Deficiency," Journal of the American Society of Nephrology, vol. 26, (2015), pp. 2423-2433.
Li, et al. "Local injection of RANKL facilitates tooth movement and alveolar bone remodelling." Oral Diseases, 25(2), 550-560. https://doi.org/10.1111/odi.13013.
Lop et al., Cutting-Edge Regenerative Medicine Technologies for the Treatment of Heart Valve Calcification, Calcific Aortic Valve Disease, (2013), (available at http://dx.doi.org/10.5772/55327), 57 pages.
McLean et al., "Training the Biofilm Generation-a Tribute to J. W. Costerton," Journal of Bacteriology, vol. 194, (Dec. 2012), pp. 6706-6711.
Miles et al. "Assessment of the changes in arch perimeter and irregularity in the mandibular arch during initial alignment with the AcceleDent Aura appliance vs no appliance in adolescents: A single-blind randomized clinical trial", Dec. 2016, vol. 150, Issue 6 American Journal of Orthodontics and Dentofacial Orthopedics (9 pages).
Nodzo et al., "Cathodic Electrical Stimulation Combined With Vancomycin Enhances Treatment of Methicillin-Resistant *Staphylococcus aureus* Implant-Associated Infections," Clinical Orthopaedics and Related Research, vol. 473, (2015), pp. 2856-2864.
Nodzo et al., "Cathodic Voltage-Controlled Electrical Stimulation Plus Prolonged Vancomycin Reduce Bacterial Burden of a Titanium Implant-associated Infection in a Rodent Model," Clinical Orthopaedics and Related Research, vol. 474, (2016), 1668-1675.
Novickij et al., "Induction of Different Sensitization Patterns of MRSA to Antibiotics Using Electroporation," Molecules, vol. 23,(2018), Article 1799, 10 pages.
O'Neill et al., "Recent Progress in the Treatment of Vascular Calcification," Kidney International, vol. 78, (Dec. 2010), pp. 1232-1239.
Palza et al, "Electroactive Smart Polymers for Biomedical Applications," Materials, vol. 12, (2019), 24 pages.
Plumbingtoday, "How to Remove Hard, White Mineral Deposits from Faucets/Showerheads," (available at https://plumbingtoday.biz/blog/how-to-remove-hard-white-mineral-deposits-from-faucets-showerheads), (Jul. 11, 2016), 4 pages.
Pozo et al., "Bioelectric Effect and Bacterial Biofilms. A Systematic Review," The International Journal of Artificial Organs, vol. 31, (2008), pp. 786-795.
Pozo et al., "Effect of Electrical Current on the Activities of Antimicrobial Agents Against Pseudomonas Aeruginosa, *Staphylococcus aureus*, and *Staphylococcus epidermidis* Biofilms," Antimicrobial Agents and Chemotherapy, vol. 53, (2009), pp. 35-40.
Pozo et al., "Prevention of *Staphylococcus epidermidis* Biofilm Formation Using Electrical Current," Journal of Applied Biomaterials & Functional Materials, vol. 12, (2014), pp. 81-83.

(56) References Cited

OTHER PUBLICATIONS

Pozo et al., "The Electricidal Effect: Reduction of *Staphylococcus* and Pseudomonas Biofilms by Prolonged Exposure to Low-Intensity Electrical Current," Antimicrobial Agents and Chemotherapy, vol. 53, (2009), pp. 41-45.
Ren et al., "Efficient Eradication of Mature Pseudomonas Aeruginosa Biofilm via Controlled Delivery of Nitric Oxide Combined with Antimicrobial Peptide and Antibiotics," Frontiers in Microbiology, vol. 7, Article 1260, (Aug. 2016), 8 pages.
Roy et al., "Disposable Patterned Electroceutical Dressing (PED-10) Is Safe for Treatment of Open Clinical Chronic Wounds," Advances in Wound Care, vol. 8, (1019), pp. 149-159.
Blum "Role of cytokines in heart failure," American Heart Journal, vol. 135, Issue 2, Feb. 1998, pp. 181-186; doi.org/10.1016/S0002-8703(98)70080-8.
Corrigan et al. "Neurogenic inflammation after traumatic brain injury and its potentiation of classical inflammation", Journal of Neuroinflammation, 2016, 13:264; doi://doi.org/10.1186/s12974-016-0738-9.
Deswal et al. "Cytokines and Cytokine Receptors in Advanced Heart Failure An Analysis of the Cytokine Database from the Vesnarinone Trial (VEST)," Circulation. 2001;103:2055-2059; ://doi.org/10.1161/01.CIR.103.16.2055.
Gavira et al. "Repeated implantation of skeletal myoblast in a swine model of chronic myocardial infarction," Eur. Heart J., 31(8): 1013-1021. doi: 10.1093/eurheartj/ehp342 (2010).
Gullestad et al. "Inflammatory cytokines in heart failure: mediators and markers," Cardiology. 2012;122(1):23-35. doi: 10.1159/000338166. Epub Jun. 12, 2012.
Liesz et al. "Editorial: Mechanisms of neuroinflammation and inflammatory neurodegeneration in acute brain injury" Front. Cell. Neurosci., 2015. doi://doi.org/10.3389/fncel.2015.00300.
Lobo-Silva et al. "Balancing the immune response in the brain: IL-10 and its regulation," Journal of Neuroinflammation, 13:297 (2016); doi.org/10.1186/s12974-016-0763-8.
Mann, "Innate Immunity and the Failing Heart: The Cytokine Hypothesis Revisited," Circ. Res. Mar. 27, 2015; 116(7): 1254-1268.
Matsumori, "Cytokines and Heart Failure: Pathophysiological Roles and Therapeutic Implications," Heart Failure, Springer, Tokyo; doi.org/10.1007/978-4-431-68331-5_3.
Paulus "Cytokines and heart failure," Heart Fail. Monit. 2000; 1(2):50-6.
Schimmel et al. "Neuroinflammation in traumatic brain injury: A chronic response to an acute injury" Brain Circ, 2017, 3(3):135-142.
Ueland et al. "Inflammatory cytokines as biomarkers in heart failure," Clinica Chimica Acta, vol. 443, Mar. 30, 2015, pp. 71-77; doi.org/10.1016/j.cca.2014.09.001.
Xiong et al. "Current understanding of neuroinflammation after traumatic brain injury and cell-based therapeutic opportunities" Chin J Traumatol. Jun. 2018; 21(3): 137-151. doi: 10.1016/j.cjtee.2018.02.003.
Beebe et al. "Bioelectric Applications for Treatment of Melanoma," Cancers (Basel). Sep. 2010; 2(3): 1731-1770, published online Sep. 27, 2010; doi: 10.3390/cancers20317.
Campbell Et Ali. "Electrical stimulation to optimize cardioprotective exosomes from cardiac stem cells" Med Hypotheses. Mar. 2016; 88:6-9. doi: 10.1016/j.mehy.2015.12.022. Epub Jan. 11, 2016.
Cervera "The interplay between genetic and bioelectrical signaling permits a spatial regionalisation of membrane potentials in model multicellular ensembles," Nature, Scientific Reports, Oct. 12, 2016 vol. 6, Article No. 35201 (2016).
Chernet et al. "Transmembrane voltage potential is an essential cellular parameter for the detection and control of the cancer tumor development in a Xenopus model," Dis. Models and Mech. 6, pp. 595-607 (2013); Doi:10.1242/dmm.010835.
Ciria et al., Antitumor effectiveness of different amounts of electrical charge in Ehrlich and fibrosarcoma Sa-37 tumors, BMC Cancer, Nov. 26, 2004, 10 pages, vol. 4, No. 87.
Dai et al. "Nanosecond Pulsed Electric Fields Enhance the Antitumour Effects of the mTOR Inhibitor Everolimus against Melanoma," Scientific Reports vol. 7, Article No. 39597 (2017).
Hamzelou et al. "Cancer reversed in frogs by hacking cells' electricity with light," New Scientist This Week, Mar. 16, 2016.
Jing-Hong et al. "Electrochemical Therapy of Tumors" Hindawi Publishing Corporation, Conference Papers in Medicine, vol. 2013, Article ID 858319, 13 pages, http://dx.doi.org/10.1155/2013/858319.
Keunen et al. "Anti-VEGF treatment reduces blood supply and increases tumor cell invasion in glioblastoma,". Proc. Natl. Acad. Sci. U. S. A. Mar. 1, 2011; 108(9): 3749-3754, published online Feb. 14, 2011; doi: 10.1073/pnas.1014480108.
Lanzetto et al. "Fundamental principles of an anti-VEGF treatment regimen: optimal application of intravitreal anti-vascular endothelial growth factor therapy of macular diseases," Graefes Arch. Clin. Exp. Ophthalmol. 2017; 255(7): 1259-1273 (published online May 19, 2017); doi: 10.1007/s00417-017-3647-4.
Meadows et al. "Anti-VEGF Therapies in the Clinic," Cold Spring Harb. Perspect. Med. Oct. 2012; 2(10): a006577: doi: 10.1101/cshperspect.a006577.
Mishra "Angiogenic neovessels promote tissue hypoxia," Proc. Natl. Acad. Sci. U. S. A. Sep. 20, 2016; 113(38): 10458-10460, published online Sep. 13, 2016; doi: 10.1073/pnas.1612427113.
Pupo et al., Electrotherapy on Cancer: Experiment and Mathematical Modeling, Current Cancer Treatment—Novel Beyond Conventional Approaches, Prof. Oner Ozdemir (Ed.) ISBN: 978-953-307-397-2, InTech, Available from: http://www.intechopen.com/books/current-cancer-treatment-novel-beyond-conventional-approaches/electrotherapy-on-cancer-experiment-and-mathematical-modeling, 2011.
Puro et al "Bioelectric impact of pathological angiogenesis on vascular function," PNAS Aug. 30, 2016 113 (35) 9934-9939; published ahead of print Aug. 22, 2016 https://doi.org/10.1073/pnas.1604757113.
RFA (radiofrequency ablation), Swedish Medical Imaging, 2 pages, author unknown, undated.
Silvers et al. "The Bioelectric Code: Reprogramming Cancer and Aging from the Interface of Mechanical and Chemical Microenvironments," Front. Cell Dev. Biol., Mar. 6, 2018; doi.org/10.3389/fcell.2018.00021.

FluidSync M200 micropump

BioLeonhardt Implantable Stem Cell Pump

Acitivin B: 6.0mV, 150Hz, pulse width 100us, square wave

EGF: 10V/cm (5V here), 500Hz, pulse width 180us, square wave

HGF: 3.5V, 10sec burst every 30 seconds, square wave

IGF-1: 3.0mV, 22Hz, square wave

PDGF30%: 3V/cm (100mV here), 10Hz, pulse width 200us, square wave

Proliferation: 15mV, 70Hz, square wave

Proliferation: 2.5-6.0V (4V here), 20Hz, pulse width 200-700us, square wave

RANKL: 3.0mV, 2Hz, square wave

Tropoelastin: 60mV, 50Hz, square wave

VEGF: 100mV, 50Hz, square wave

SDF-1 (2nd part): 0.25mA (3.0V shown here), 100Hz, 100us pulse width, square wave

# SYSTEM AND METHOD FOR TREATING INFLAMMATION

CROSS-REFERENCE TO RELATED APPLICATIONS

This application is a continuation-in-part of U.S. patent application Ser. No. 15/812,760, filed Nov. 14, 2017, which is a continuation-in-part of U.S. patent application Ser. No. 15/460,129, filed on Mar. 15, 2017, which itself claims the benefit under 35 U.S.C. § 119 of:

U.S. Provisional Patent Application Ser. No. 62/308,702, filed Mar. 15, 2016;
U.S. Provisional Patent Application Ser. No. 62/363,012, filed Jul. 15, 2016;
U.S. Provisional Patent Application Ser. No. 62/364,472, filed Jul. 20, 2016;
U.S. Provisional Patent Application Ser. No. 62/375,271, filed Aug. 15, 2016;
U.S. Provisional Patent Application Ser. No. 62/385,124, filed Sep. 8, 2016;
U.S. Provisional Patent Application Ser. No. 62/454,521, filed Feb. 3, 2017; and
U.S. Provisional Patent Application Ser. No. 62/352,930, filed Jun. 21, 2016, the disclosure of each of which is incorporated herein in its entirety by this reference.

FIELD

This application relates generally to the field of medical devices and associated treatments, and more specifically to precise bioelectrical control of inflammation in a subject. For example, described is that the stimulation of a subject's brain tissue, possibly augmented with the administration of a composition comprising, among other things, stem cells and nutrients, can be useful to stimulate and treat the inflammation associated with, e.g., a concussion.

BACKGROUND

To date, no effective treatment for a concussion exists. Concussion management thus far has focused on prevention and rest, allowing symptoms to subside naturally before normal activity is resumed.

The use of anti-inflammatory drugs for the treatment of concussion has been examined. Non-steroidal anti-inflammatory drugs (NSAIDs) seemed to be an attractive option. However, evidence exists to suggest that NSAIDs may not be the best pharmacotherapy for managing the neurobiological factors underlying concussive injuries. For example, chronic treatment with ibuprofen worsens the cognitive alterations in rodents exposed to an experimental TBI. Other NSAIDs, such as minocycline, are able to reduce apoptotic damage in several forms of CNS injury, such as spinal cord injury, but do not show any beneficial effects when examining recovery times from mild TBI. Taken together, these data demonstrate that preventing an inflammatory response to a concussion is likely not a viable treatment. Furthermore, the evidence suggests that the concussed brain presents a unique inflammatory signature as opposed to a general inflammatory response that occurs following any CNS injury.

The search for a viable concussion treatment continues. An acute metabolic cascade following a concussion has been characterized in detail. Unfortunately, targeting this metabolic cascade has failed to produce viable treatment options. Treatment strategies focused on managing the neuroinflammatory responses to concussion may prove more effective. Data exists suggesting that manipulating neuroinflammation can be used as a treatment strategy to manage the long-term deficits produced by a concussive injury. However, general anti-inflammatory drugs will not serve as a "magic bullet." Rather, it seems that a tailored array of pro- and anti-inflammatory compounds given at particular temporal intervals will likely be implemented given the complexity of the inflammatory response to concussion. Treatments will likely differ based on severity of brain injury, age of the patient, and previous brain injury history. Furthermore, treatment strategies require close attention be paid given the fluctuations of inflammatory profiles over time following a concussion.

The failures of NSAIDs and other anti-inflammatory agents in mitigating post-concussive damage in a subject highlight the need for customized approaches for the subject.

BRIEF SUMMARY

Customized approaches for controlling inflammation in a subject can be provided by controlled protein expression on demand by bioelectric stimulation. Controlled protein expression on demand by bioelectric stimulation can be designed to deliver a very specific protein regimen at a very specific time; often in very specific sequence at a very specific dose.

Described herein is a method of treating inflammation in a subject comprising first reading (or otherwise determining) the levels of a subject's inflammatory cytokines after, e.g., a concussion and then adjusting the subject's levels of inflammatory cytokines to a desired level to improve recovery from the concussion or traumatic brain injury ("TBI"). It is found that the right timing and the right balance in the right sequence of inflammatory cytokines aids in a subject's recovery from stroke, concussion, and/or traumatic brain injury. Electric stimulation should be provided to the subject to control the expression and/or release of SDF-1 (stem cell homing), IGF-1 (DNA repair), HGF, VEGF, PDGF, eNOS, HIF 1 alpha, IL-6, Activin A+B, Stem cell proliferation signals, and stem cell differentiation control signals. To this may be included, e.g., GDF-10, GDF-11, Neurogenin 3, and FGF.

For recovery from stroke, concussion, or traumatic brain injury, if electric stimulation alone does not provide complete recovery, the patient may then also receive a composition comprising adipose-derived or bone marrow-derived stem cells (MSCs), endothelial progenitor cells, a variety of selected growth factors cocktail, selected exosomes, selected micro RNAs, selected alkaloids, selected anti-inflammatory agents, nutrient hydrogel, organ specific matrix, and amniotic fluid.

For severe recovery need cases, the method preferably further includes communicating wirelessly with miniature "Bion" implants that are implanted into the damaged organ and/or tissue (e.g., brain) regions that relay and amplify applied protein expression signals.

Described is a device that determines a subject's inflammatory markers following organ injury and then, in response to the determination(s), delivers regenerative and recovery bioelectric protein expression signals to the subject's tissue so as to up-regulate and/or down-regulate selected protein expression thereby, thus helping to establish inflammatory balance for organ healing and recovery in the subject.

Such a device typically comprises: a power source, an input to determine the subject's inflammatory markers, and means for delivering an electrical signal to the subject's tissue. The device utilizes the electrical signal to precisely control protein expression in the tissue on demand. Such proteins are typically selected from the group consisting of insulin-like growth factor 1 ("IGF1"), interleukin 6 ("IL-6"), interleukin 10 ("IL-10"), interleukin-1β ("IL-1β"), transforming growth factor-β ("TGFβ"), tumor necrosis factor alpha ("TNF-α"), and any combination thereof.

Such a device may be utilized, e.g., to treat a subject suffering from a brain concussion, traumatic brain injury ("TBI"), heart failure, etc. In the methods relating to concussion or TBI, the bioelectric protein expressions sequence typically comprises: from about five (5) to about forty (40) minutes, to increase IL-1β following a concussion (precedes the secretion of ciliary neurotrophic factor (CNTF) and nerve growth factor (NGF), both of which promote the growth and survival of neurons and defend against the instigation of apoptotic pathways), wherein the device then determines and adjusts the bioelectric protein expression signals to the subject's tissue for about five (5) minutes of an IL-1β inhibition shut off signal, and then from about five (5) to forty (40) minutes, a rise in TNF-α, wherein the device then determines and adjusts the bioelectric protein expression signals to the subject's tissue for about five (5) minutes of TNF-α inhibition shut off signal, and then from about five (5) to forty (40) minutes rise in TGFβ, and wherein the device then determines and adjusts the bioelectric protein expression signals to the subject's tissue for about five (5) minutes of a TGFβ inhibition shut off signal, and then about three (3) minutes of a rise in IL-10.

Such a method may further include separately delivering to the subject (e.g., via a pump and catheter) a "cocktail" of regenerative agents comprising any combination of the following: stem cells, endothelial progenitor cells, selected exosomes, selected alkaloids, selected anti-inflammatory agents, nutrient hydrogel, organ specific matrix, selected growth factors, amniotic fluid, placenta fluid, cord blood, and embryonic sourced growth factors and cells.

The method may be used in a subject to regenerate brain cells. Such a method typically comprises generating electrical signals from the device to control the expression and/or release of a protein, wherein the protein is selected from the group consisting of insulin-like growth factor 1 ("IGF1"), interleukin 6 ("IL-6"), interleukin 10 ("IL-10"), interleukin-1β ("IL-1β"), transforming growth factor-β ("TGFβ"), tumor necrosis factor alpha ("TNF-α"), and any combination thereof. Again the method may further comprise separately delivering to the subject stem cells and/or growth factors comprising any combination of IGF1, IL-6, IL-10, IL-1β, TGFβ, TNF-α, and any combination thereof.

The device may be used to achieve brain regeneration, cognitive function brain improvement, brain stroke, heart recovery, and traumatic injury recovery, eye regeneration, and/or ear hearing regeneration.

The described bioelectric signals appear to have two primary mechanisms of action. First, they provide instructions for the subject's DNA to build protein(s). And, second, they provide instructions for cell membranes to open and close pores and to activate electrical transfers of energy on demand. As further described herein, action potentials management are most often controlled by frequency durations.

While not intending to be bound by theory, the following may help to explain the invention. Inflammation is an immune response of the body that works as a contained fire that is pre-emptively sparked as a defensive process during infections or upon any kind of tissue insult, and that is spontaneously extinguished after elimination or termination of the damage. However, persistent and uncontrolled immune reactions act as a wildfire that promote chronic inflammation, unresolved tissue damage, and, eventually, chronic diseases. A wide network of soluble mediators, such as endogenous bioactive lipids, governs all immune processes. These mediators are secreted by basically all cells involved in the inflammatory processes and constitute the crucial infrastructure that triggers, coordinates, and confines inflammatory mechanisms. However, these same molecules are also involved in the detrimental transition from acute to chronic inflammation, be it for persistent or excessive action of pro-inflammatory lipids or for the impairment of the functions carried out by resolving ones. For example, bioactive lipids have been linked to several chronic diseases, including rheumatoid arthritis, atherosclerosis, diabetes, cancer, inflammatory bowel disease, systemic lupus erythematosus, and multiple sclerosis.

Provided are a system and methods designed to promote positive inflammation in moderation, which is essential for healing and when the body is ready to turn off the inflammatory cycle loop to avoid the detrimental effects of chronic inflammation.

The invention includes the idea of recording the ideal neuro inflammation bioelectric and biochemical/hormonal responses of a healthy recovery (without chronic neurological inflammation being triggered) and storing this data in a microprocessor database. For example, recording the brain recovery of a toddler with brain injury. The treatment regime for an injured adult is then compared to this ideal (in addition to real time sensing and adjustments of therapy). The treatment regime chosen is a balance between the ideal recovery sequence (recorded in the microprocessor) and real time adjustments made by real time monitoring.

Provided herein (e.g., in the "neuro hormonal closed loop" approach) are systems and methods that, at times, send bioelectric signals to the brain in order to allow the brain to adjust its response(s) to injury. At times, signals are directed to the injured tissue to allow the tissue to release proteins directly, which influences the neuro hormonal loop with the brain, inflammation, and healing. The system and methods may interfere and control messaging up to the brain, back from the brain, or directly in tissues. Such may be used in combined therapy by combining bioelectric signaling control of inflammation, blood pressure, healing, and programmed biologics delivery via a closed loop sensing and customized therapy neuromodulation system.

DETAILED DESCRIPTION

Customized inflammation control could also be useful for other disease treatment and management. Preferably, one does not deliver a single drug or single signal or one set of signals for inflammation control. A subject suffering from inflammation benefits from real time monitoring and constant adjustment of signals to achieve inflammation balance. Too much is bad, too little is bad, too much or too little at the wrong time can be bad for the subject. The sequence is preferably correct and constantly adjusted. Multiple inflammatory or anti-inflammatory cytokine levels need to be up or down at just the right time depending on the status of recovery and many other variables. Cytokines such as IL-1, TNF-A or IL-6 at the right time at the right levels can be highly useful for healing of an organ, but at the wrong levels at the wrong time, the very same cytokines can be highly damaging to the organ and/or tissue and can cause rapid deterioration, Such adjustments include elevating or reducing TNF-A, IL-1, IL-6, and other inflammatory or anti-inflammatory cytokines. Regardless of inflammation control, the organ or tissue should be regenerated back to maximal health. A healthy regenerated organ does not have an inflammation problem, only an unhealthy organ has an inflammation problem. Controlling inflammation only treats the symptom; not the disease. Inflammation is a reaction to an unhealthy organ; not the other way around. A subject's tooth becomes inflamed when, e.g., there is a root infected from trapped bacteria and breakdown. The problem is the source of the infection and breakdown that is to be treated; not just the inflammation. Inflammation control herein is preferably customized for the subject's condition, and preferably adjusted constantly (e.g., many times a day, sometimes many times a minute, based on real time data).

Figure 23:
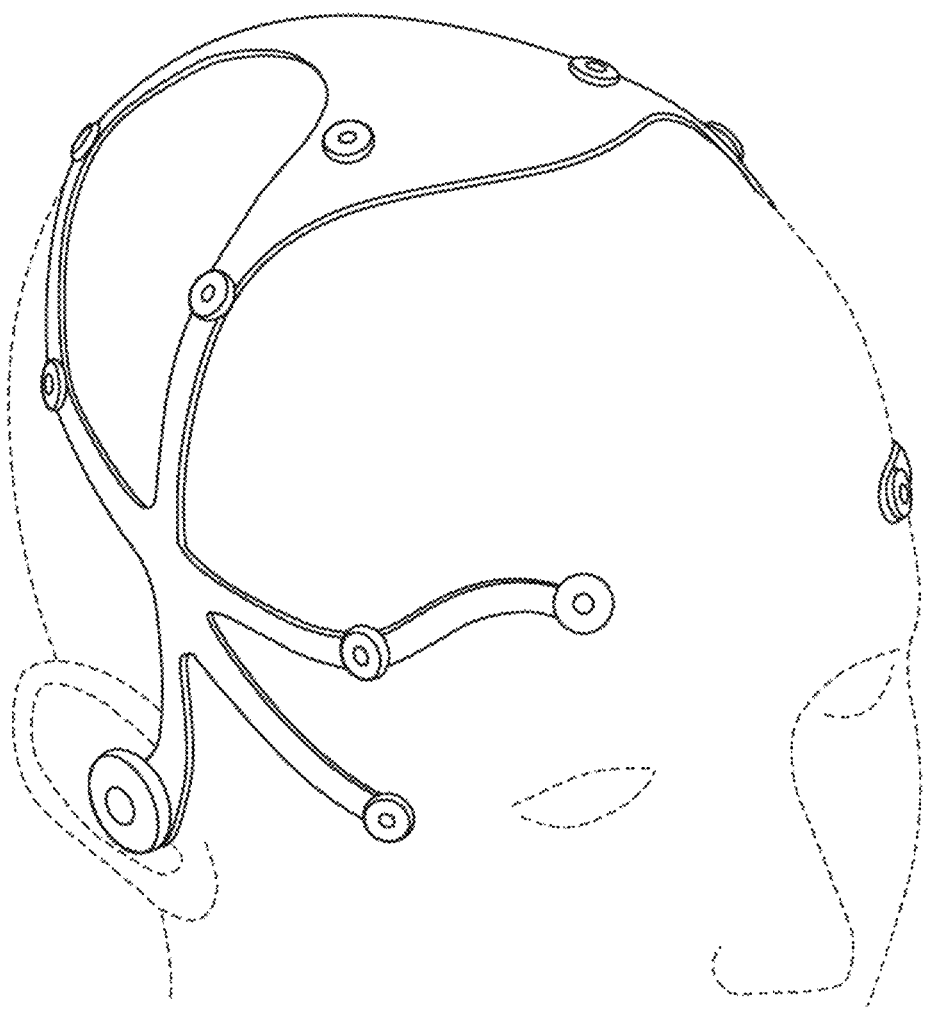
FIG. 23 depicts a helmet design for use as described herein.

Described herein is real time, data-based customized bioelectric inflammation management for, e.g., heart, stroke, traumatic brain injury and concussion recovery (see, e.g., FIG. 23 for a preferred "helmet" with nodes particularly useful for real time management when inflammation follows brain injury or stroke).

Figure 24:
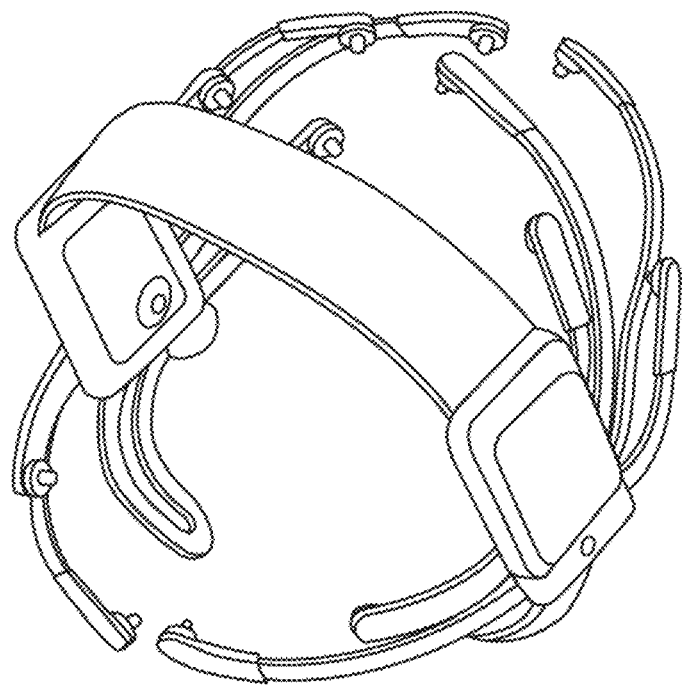
FIG. 24 depicts a helmet design for use as described herein.

As depicted in FIGS. 23 and 24, such a helmet has, as primary components, wireless means to read real time inflammatory and anti-inflammatory cytokine levels in an organ or blood flow (e.g., in the brain), wireless bioelectric signals directed to specific organ regions to manage the control of inflammation with real time customized delivery of signals for balancing cytokine levels, and bioelectric signals delivered via the nervous and cardiovascular system to manage total body electrical potentials balance, all for inflammation control therapy.

In certain embodiments, both recording electrodes and stimulating electrodes are appropriately positioned, e.g., about the patient's head with a helmet to measure and sense the inflammatory situation, and then in response stimulating the inflamed tissue appropriately. In some instances, the stimulating electrode can be an external coil, situated above microbeads placed in close proximity to the inflamed tissue. These embodiments can be readily adapted to areas of the body other than the head.

The device depicted in FIG. 23 has stimulators, EEG hardware (e.g., sensor pads), and stimulator-pump hardware. The legs are relatively thick and follow the form of the subject's head ending in, e.g., EEG sensors. Stimulators are typically placed between the EEG sensors. At the apex of the depicted device, there are hardware storage units for the EEG (e.g., battery and SD storage card) and the stimulator and pump. The stimulator and pump are preferably positioned on the device at the posterior portion of the subject's head.

Applications of the device include treating a subject for: cerebral stroke recovery, concussion recovery, injury-related brain damage, brain cancer recovery, Parkinson's, Alzheimer's and dementia, cerebral aneurysm repair, depression, brain memory recovery and enhancement, and brain function enhancement.

In use, the device is focused on brain regeneration utilizing microcurrent signals that home stem cells to the brain and cause new blood vessels to grow. For severe cases, stem cell and growth factor injections are added, and for extremely severe cases, a re-fillable, programmable micro pump regeneration stimulator is incorporated into the system.

The device is designed to stimulate true neurogenesis, i.e., the formation and nurturing of new neuron cells, to regenerate damaged or diseased brain tissue for true brain regeneration. By bioelectric stimulation, the device controls the release of, e.g., brain regeneration promotion cytokines. Such cytokines may include SDF-1 (for stem cell homing factor and recruitment of stem cells from the patient's own bone marrow, fat and circulating blood to the stimulated brain tissue areas). Another signal of opposite polarity for controlling the differentiation of those recruited stem cells into healthy functioning brain tissue. Other cytokines are IGF-1 (for DNA level repair), HGF, EGF, Activin A+B, eNOS, VEGF, follistatin and tropoelastin (all of which contribute to regeneration), eNOS, HGF and VEGF (which help improve blood supply to the treated area).

For severe brain damage recovery and difficult disease cases, the programmable micro infusion pump (fillable daily or weekly) is included, with angiogenic and regeneration compositions comprised of a variety of cell types, growth factors, nutrient hydrogel, exosomes, Micro RNAs, brain matrix and other neurogenesis promoting molecules including harmine and tetrahydroharmine alkaloids and inflammation control agents. The combination of bioelectric regeneration stimulator, micro infusion pump and angiogenic and regeneration compositions are believed to help people recover from brain injuries or brain related diseases better than with previous therapies.

For brain tumor cancer patients, pending tuned bioelectric signals are used to reduce cell division and blood supply to the tumors.

Inflammation is better managed with more than a single drug or single bioelectric signal. The body produces inflammation to promote healing and the right cytokines at the right time in the right sequence greatly aide in healing. The very same cytokines at the wrong time in the wrong sequence and at the wrong levels for the wrong duration can cause detrimental damage to health. The device determines these inflammatory and anti-inflammatory cytokines to deliver multiple cytokine (up- or down-regulation) real time to best attempt to gain the right inflammatory balance.

The depicted device responds to a subject's inflammatory marker levels, delivers bioelectric protein expression signals to the subject's tissue so as to up-regulate and/or down-regulate select protein expression(s) in the subject so as to balance inflammation in the subject. The device comprises: a power source, an input or several inputs to determine the subject's inflammatory markers, and means for delivering bioelectric signals to the subject's tissue, wherein the device utilizes the electrical signals to precisely control select protein expression(s) in the tissue on demand.

Specifically, anti-inflammatory cytokines serve opposing roles in response to brain injury. Some effects are beneficial while others are detrimental. Balance is essential to optimal recovery.

For example, IL-1β provides neuroprotection following brain injury and therefore might be considered part of the regenerative process. Paradoxically, it has also been shown that chronic inhibition of IL-1β for up to one week following a controlled cortical impact ("CCI")—induced mild/moderate TBI reduces cerebral edema and tissue loss while improving the cognitive outcome by modifying the inflammatory response. These data suggest that prolonged exposure to IL-1β may be associated with neurotoxic effects following a concussion.

TNF-α, in the correct balance, appears to play both neuroprotective and neurotoxic roles following brain injury.

IL-6 acts as both a pro-inflammatory and anti-inflammatory cytokine and is considered to be a key regulator during the acute phase of the inflammatory response to infections and tissue damage. The key is getting the correct IL-6 balance at the right time in the right sequence.

TGF-β confers potential short-term beneficial effects following clinical and experimental TBIs by down-regulating the inflammatory response. However, long-term, TGF-β may be detrimental and may increase the risk of developing other neurological disorders.

The beneficial effects of IL-10 administration are transient and circumstantial. These beneficial effects appear to be dose-specific and site-specific, requiring pre-treatment in order to confer protection.

Lobo-Silva et al. "Balancing the immune response in the brain: IL-10 and its regulation," *Journal of Neuroinflammation*, 13:297 (2016); doi.org/10.1186/s12974-016-0763-8, describes the importance of IL-10 balance in inflammation management. As described therein, manipulating the protective and degenerative neuroinflammation balance is important. Mechanisms exist to avoid exaggerated neuro-immune responses including the production of anti-inflammatory cytokines, such as IL-10. IL-10 binding to its receptor triggers a series of signaling cascades mediated by the Janus kinase signal transducer and activator of transcription (STAT) pathway. Signalling through the IL-10 receptor regulates several steps of the immune response, from decreasing cytokine gene expression to down-regulating the expression of major histocompatibility complex class II and thus antigen presentation to T cells. IL-10 prevents apoptosis by activating the PI3K/Akt cascade and enhancing the expression of anti-apoptotic factors as Bcl-2 and Bcl-xl, while attenuating caspase-3. IL-10 inhibits the production of pro-inflammatory cytokines by microglia, protecting astrocytes from excessive inflammation. IL-10 also acts on astrocytes and potentiates production of TGF-β. IL-10 is an important mediator of the crosstalk between microglia, astrocytes, and neurons. Several studies directly implicate defective IL-10 production or signaling in patients and animal models of neurological diseases, ranging from neuropathic pain to multiple sclerosis, Alzheimer's disease, or Parkinson's disease.

Prolonged exposure to inflammatory cytokines is typically ultimately harmful, shifting the intrinsic neuroprotective efforts of the immune response to the detrimental effects of neuroinflammation. However, neuroinflammation may contribute to the neuroprotective regenerating efforts of the brain and in its absence the cumulative damage is increased following injury.

In certain embodiments, provided is a system that reads inflammation real time and constantly adjusts bioelectric stimulation and cytokine releases to modulate and manage inflammation in a subject in real time. This is preferably done to manage the cycle of chronic inflammation in the subject. In essence, it activates a "re-start button" on the subject's chronic inflammation cycle.

The microprocessor preferably stores ideal optimal healing cycles. Treatment regimes are adjusted real time between data coming in via real time monitoring of inflammation and ideal optimal healing algorithms stored on the microprocessor of the microstimulator and reader. The ideal optimal healing cycles may be derived from measurements made in healthy subjects having an inflammation causing event, who recover quickly and fully (such as a toddler head injury recovery).

Proper inflammation management is believed to be served best by bioelectric energy management that in turn controls release of the proper cytokines in the correct sequence at the correct time for healthy recovery, especially when combined with proper diet and exercise.

Inflammation has long been a well-known symptom of many infectious diseases, but new molecular and epidemiological research increasingly suggests that it is also intimately linked with a broad range of non-infectious diseases.

Inflammation is a response of the immune system to injury, irritation, or infection caused by invading pathogens, radiation exposure, very high or low temperatures, or autoimmune processes. Therefore, inflammation is a mechanism for removing damaged cells, irritants, or pathogens. Inflammation is considered to be beneficial when it is short term and under control within the immune system ("acute inflammation"). Inflammation that persists longer is known as chronic inflammation. This inflammation is characterized by the simultaneous destruction and healing of tissue.

The various factors that are known to induce chronic inflammatory responses also cause numerous chronic diseases. These factors include bacterial, viral, and parasitic infections (e.g., Helicobacter pylori, Epstein-Barr virus, human immunodeficiency virus, flukes, schistosomes); chemical irritants (e.g., tumor promoters, such as phorbol ester 12-O-tetradecanoylphorbol-13-acetate, also known as phorbolmyristate acetate); and non-digestible particles (e.g., asbestos and/or silica). Inflammation produces reactive oxygen species and reactive nitrogen species, which cause oxidative damage and further lead to chronic diseases. Inflammation also recruits leukocytes that secrete inflammatory cytokines and angiogenic factors to the site of tissue insult. These cytokines are required for proper wound healing and to stimulate epithelial cell proliferation. However, if uncontrolled, these cytokines can lead to inflammatory disorders. All these inflammatory products have been shown to be regulated by the nuclear transcription factor NF-κB.

A tailored array of pro-inflammatory and anti-inflammatory compounds given at particular temporal intervals is herein implemented. Treatment differs based upon severity of the brain injury, the age of the patient, and a previous history of brain injury. Furthermore, treatment strategies require close attention be paid to when a patient consults a medical professional after brain injury given the fluctuations of inflammatory profiles over time following a concussion.

A customized real time read and then deliver bioelectric protein expression(s) therapy should be able to better strike the balance between acute and delayed actions of cytokines may prove to be appropriate targets for treatment of concussion.

Following the mechanical injury suffered by concussed patients, there is an acute cytokine response. IL-1, a family of 11 cytokines known for their regulation of inflammatory responses, increases rapidly in both human and rodent cases of mild to severe TBI. Within this cytokine superfamily, IL-1α and IL-1β convey a pro-inflammatory response that aids in the defense against infection or injury. In rodent models of concussion, IL-1α and IL-1β are up-regulated within hours following injury. IL-1α shows an acute spike following a concussion, while IL-1β shows a much more gradual increase which may represent a portion of the delayed cytokine response to CNS injury.

IL-1β levels remain elevated for days following experimental concussions and show significantly higher levels relative to other pro-inflammatory cytokines. The elevation in IL-1β levels seen after brain injury appears to be conditional on the severity of the trauma. As such, experimental injuries lead to contusions, mimicking a more potent TBI than a concussion, and produce more IL-1β mRNA expression in tissues surrounding the contusion, which lasts up to 6 days following the onset of injury.

The rise in IL-1β following a concussion precedes the secretion of ciliary neurotrophic factor (CNTF) and nerve growth factor (NGF), both of which promote the growth and survival of neurons and defend against the instigation of apoptotic pathways. Data suggest that IL-1β provides neuroprotection following brain injury and therefore might be considered part of the regenerative process. Paradoxically, others have shown that chronic inhibition of IL-1β for up to one (1) week following a CCI-induced mild/moderate TBI reduces cerebral edema and tissue loss while improving the cognitive outcome by modifying the inflammatory response. These data suggest that prolonged exposure to IL-1β may be associated with neurotoxic effects following a concussion.

Given that IL-1β is able to stimulate the expression and/or release of other proinflammatory cytokines, such as tumor necrosis factor-alpha (TNF-α), it is not surprising the IL-1β inhibition results in an atypical inflammatory response following fluid percussion injuries. The IL-1β-dependent hypersecretion of other cytokines may produce a toxic inflammatory environment for neurons surrounding the site of injury. Therefore, interrupting IL-1β immediately following the endogenous secretion of neurotrophic factors might prove to be effective in concussion management.

Like the IL-1 family of cytokines, TNF-α shows a rapid response to experimental brain injury and is considered to be an early mediator of CNS damage. Following experimental TBIs, ranging from a mild closed head injury to a more severe lateral fluid percussion injury, TNF-α rises rapidly and peaks within hours, returning to normal levels within 24 hours of the injury. Like IL-1β, TNF-α appears to play both neuroprotective and neurotoxic roles following brain injury.

Acutely, TNF-α alters the permeability of the blood brain barrier (BBB), a well-characterized physiological consequence of concussions. Appropriate alterations to BBB permeability may be necessary to regulate the infiltration of blood-born defense mechanisms following brain injury. For example, mice lacking complete functional TNF-α signaling show greater tissue damage, increased BBB permeability, and increased recovery times following both moderate and severe CCI injuries, suggesting that TNF-α is necessary for normal recovery. However, inhibiting TNF-α transcription and bioactivity pharmacologically following a mild closed head injury improves neurological outcome and motor function recovery, normalize BBB permeability and decrease edema size, suggesting inhibition of TNF-α activity facilitates recovery. TNF-α signaling may be neurotoxic in the acute stages of TBI. In conjunction with IL-1, TNF-α stimulates the expression and/or release of NGF from astrocytes, which may explain some of its neuroprotective effects. TNF-α may promote proliferation of neurons. Central blockade of TNF-α following a concussion may prove to be beneficial, while prolonged antagonism could be detrimental.

TNF-α stimulates IL-6 expression. IL-6 acts as both a pro- and anti-inflammatory cytokine and is considered to be a key regulator during the acute phase of the inflammatory response to infections and tissue damage. IL-6 increases both mild and moderate/severe TBI in rodents and has been detected at high levels for weeks following severe human brain injuries. In mice lacking IL-6, experimental cortical freeze injuries or cytotoxic brain injuries result in increased oxidative stress, decreased cell survival, and lengthened recovery times compared to WT mice. IL-6 secretion leads to elevated production of NGF in astrocytes and suppresses the production of both TNF-α and IL-1β. Also, IL-6 deficient mice exposed to a closed cortical impact, mimicking a mild TBI, show exaggerated behavioral abnormalities and increased expression of IL-1β one hour following injury.

Overexpression of the IL-6 gene, on the other hand, resulted in shortened recovery times.

TGF-β promotes tissue repair. TGF-β expression is induced by the presence of inflammatory cytokines and forms a negative feedback loop by suppressing the production of pro-inflammatory cytokines such as IL-1, IL-6, TNF-α, and IFN-γ. This negative feedback system ensures that the host is protected from proliferating inflammatory attacks. However, the beneficial effects of TGF-β seem to be dependent on its temporal expression and/or release and concentration. Excessive expression of TGF-β, e.g., hinders the intrinsic repair mechanisms of the brain and confers a predisposition for the development of serious infections.

Expression of TGF-β peaks within 24 hours after TBI in human cases. TGF-β may confer potential short-term beneficial effects following clinical and experimental TBIs by down-regulating the inflammatory response. Only local administration has been shown to promote tissue repair, while systemic administration results in an immunosuppressive reaction.

IL-10 may be neuroprotective as it decreases levels of reactive oxygenated species, decreases the expression of pro-inflammatory cytokines such as IL-1 and TNF-α, and suppresses further activation of microglia and astrocytes. The beneficial effects of IL-10 administration are transient and circumstantial. These beneficial effects appear to be dose- and site-specific, requiring pre-treatment in order to confer protection, while the type of injury model also seems to influence the use of IL-10.

Provided is a method and system for the controlled up- or down-regulation of CXCL5 (C—X—C motif chemokine 5) expression. CXCL5 is a protein having a role in preventing artery occlusion and cancer tumor growth as well as many other potential useful therapeutic applications including the treatment of arthritis.

Similarly, other CXCLs were induced by electrical stimulation in vitro. Using 20 V, 1 Hz with a frequency of 5 ms, a 3-time up-regulation in 15 minutes of CXCL5 was attained that decreased to 2.5 times in one hour, which persisted at around 2.5-3 times at 24 hours. These results were obtained on cultured adipocyte-derived mesenchymal stem cells. The results are similar to when the treated cells were bone marrow mesenchymal-derived stem cells. Similar results were found with CXCL1, a chemokine with angiogenic activity, and the potential anti-tumor CXCL3, CXCL 9, and CXCL 10. For CXCL 9 and CXCL 10, the up-regulation was really significant.

The protein encoded by this gene, CXCL5 is a small cytokine belonging to the CXC chemokine family that is also known as epithelial-derived neutrophil-activating peptide 78 (ENA-78). It is produced following stimulation of cells with the inflammatory cytokines interleukin-1 or TNF-alpha. Expression of CXCL5 has also been observed in eosinophils, and can be inhibited with the type II interferon IFN-γ. This chemokine stimulates the chemotaxis of neutrophils possessing angiogenic properties. It elicits these effects by interacting with the cell surface chemokine receptor CXCR2. The gene for CXCL5 is encoded on four exons and is located on human chromosome 4 amongst several other CXC chemokine genes. CXCL5 has been implicated in connective tissue remodeling. CXCL5 has been also described to regulate neutrophil homeostasis.

CXCL5 plays a role in reducing sensitivity to sunburn pain in some subjects, and is a "potential target which can be utilized to understand more about pain in other inflammatory conditions like arthritis and cystitis." CXCL5 has chemotactic and activating functions on neutrophils, mainly during acute inflammatory responses. However, CXCL5 expression is also higher in atherosclerosis (a chronic inflammatory condition), but is not associated with neutrophil infiltration. Instead, CXCL5 has a protective role in atherosclerosis by directly controlling macrophage foam cell formation.

CXCL5 has potential properties for organ regeneration and recovery including cancer tumor treatment including liver cancer, prostate cancer, atherosclerosis, colorectal cancer, pancreatic cancer, pneumonia, acute respiratory distress syndrome, other lung disorders, arthritis, pain associated with, e.g., sunburn, inflammation, diabetic foot and leg ulcer wound healing, knee stem cell therapy, periodontitis, and neuropathic pain management.

The CXCL5 protein was found in previous pre-clinical studies to be a key cytokine in potentially reducing risk of heart attacks, strokes and limb amputations due to atherosclerosis and resulting artery occlusion. Control of CXCL5 expression has also been suggested from data gathered in numerous studies as a possible means to stop cancer tumor growth.

CXCL5 is one of the most potent cytokines known to reduce risk of arterial occlusion that is a primary cause of heart attacks and stroke as well as lower limb ischemia. Numerous studies have demonstrated that controlled down-regulation of CXCL5 can be anti-angiogenic and thus help starve cancer tumors of blood supply.

CXCL5 biological processes include positive regulation of leukocyte chemotaxis, positive regulation of cell proliferation, inflammatory response, G-protein coupled receptor signaling pathway, response to lipopolysaccharide, signal transduction, cell-cell signaling, immune response, chemokine-mediated signaling pathway, cell chemotaxis, and neutrophil-mediated immunity.

Described is a bioelectric stimulation device that treats a subject after concussion through real time biosensing and customized bioelectric signal deliveries. Such a device (e.g., FIGS. 23 and 24), which can be in the form of a helmet (see, e.g., CerebraCell from Leonhardt Ventures), preferably non-invasively recruits a subject's stem cells (e.g., via SDF-1 or down-regulation of CXCR4) to damaged brain tissue via at least one bioelectric homing signal. Signals delivered by, e.g., an implantable lead (or micro implant) are also useful, particularly in severe injury cases. Such bioelectric signals can also control the expression and/or release of many proteins that promote new blood vessel growth and brain tissue repair.

The surest way to intended signal purity to a specific region of the brain for a specific treatment however is via controlled protein expression with an implantable lead. A micro implant may include a multi-site electrode array connected via an output to a VLSI biomimetic model, having an input associated with the subject's hippocampus. An implantable micro stimulator device is already approved for human clinical trials for another deep brain application.

Preferably, the device has sensors (or other means) that are able to determine cytokine levels in the subject. For example, nodes on the "cap" or helmet (FIG. 23 or 24) can communicate with implanted micro implants receiving and send signals constantly (sending and receiving signals 24 hours per day). Multiple implants may be wirelessly powered and programmed in one or more region of the brain. For deep brain stimulation, communication exists between the brain cap and deep brain micro implant.

Programmed into the microprocessor are references to cytokine release that occurs (in both balance and sequence) similar to that of when a healthy baby or young child fully recovers from a brain injury as a baseline. The microprocessor adjusts up and down from there, based on real time input from the injured brain. The microprocessor is also pre-programmed in signals and their resulting cytokine release(s) known to contribute to healthy brain development, function and injury recovery.

The device(s) may be used in conjunction with a microinfusion pump to deliver select proteins to the subject. An implantable combination microstimulator and re-fillable micropump with pacing infusion leads may be directly connected with specific brain locations.

With such a device, electrical signals emitted from the device may be used to cause the subject to halt the unchecked flux of ions through regulated channels in membranes, which minimizes brain damage.

Electrical signals emitted from the device may be used to reverse ionic disequilibrium, which minimizes brain damage.

With such a device, electrical signals emitted from the device may be used to cause the subject to reverse neuronal depolarization, which minimizes brain damage. This helps to bring electrical membrane polarizations into healthy balance.

Electrical signals emitted from the device may be used to encourage a healthy balance of Ca2+ levels so as to avoid over accumulation of Ca2+ in the mitochondria, which can hinder metabolism leading to impairments of ATP production.

With such a device, electrical signals emitted from the device may be used to control dependent Na+ and K+ pumps reacting to the concussion.

With such a device, electrical signals emitted from the device may be used to cause the subject to reduce, stop, or otherwise bring under control indiscriminate release of excitatory neurotransmitters.

With such a device, electrical signals emitted from the device may be used to stop, slow down, or otherwise bring under balanced control, adenosine triphosphate (ATP).

With such a device, electrical signals emitted from the device may be used to control glucose metabolism and hyperglycolysis.

Electrical signals emitted from the device may be used to bring into balance glucose supply and demand, so as to minimize brain damage.

With such a device, electrical signals emitted from the device may be used to encourage a healthy balance of N-methyl-D-aspartate (NMDA), e.g., by receptor activation. Such action decreases over-activation of the NMDA receptors.

With such a device, electrical signals emitted from the device may be used to cause the subject to increase cerebral blow flow to healthy levels via controlled release of VEGF, PDGF, eNOS, and HGF, so as to minimize brain damage. IGF-1, growth and differentiation factor 10 ("GDF10"), EGR, activin, and BDNF/TrkB may also be useful. Such bioelectric signals are described herein.

In summary, bioelectric signals encourage stem cell recruitment to the subject's brain, controlled electrical signals reinforce positive brain pathways, and control expression and/or release of select proteins, thus enhancing memory and recall.

In a preferred embodiment, an organ regeneration composition hereof comprises adipose-derived stem cells, bone marrow-derived stem cells, muscle-derived stem cells (e.g., when needed for muscle), exosomes, MicroRNAs, nutrient hydrogel, growth factor cocktail, organ specific matrix, selected alkaloids, and/or selected anti-inflammatory agents.

Figure 1:
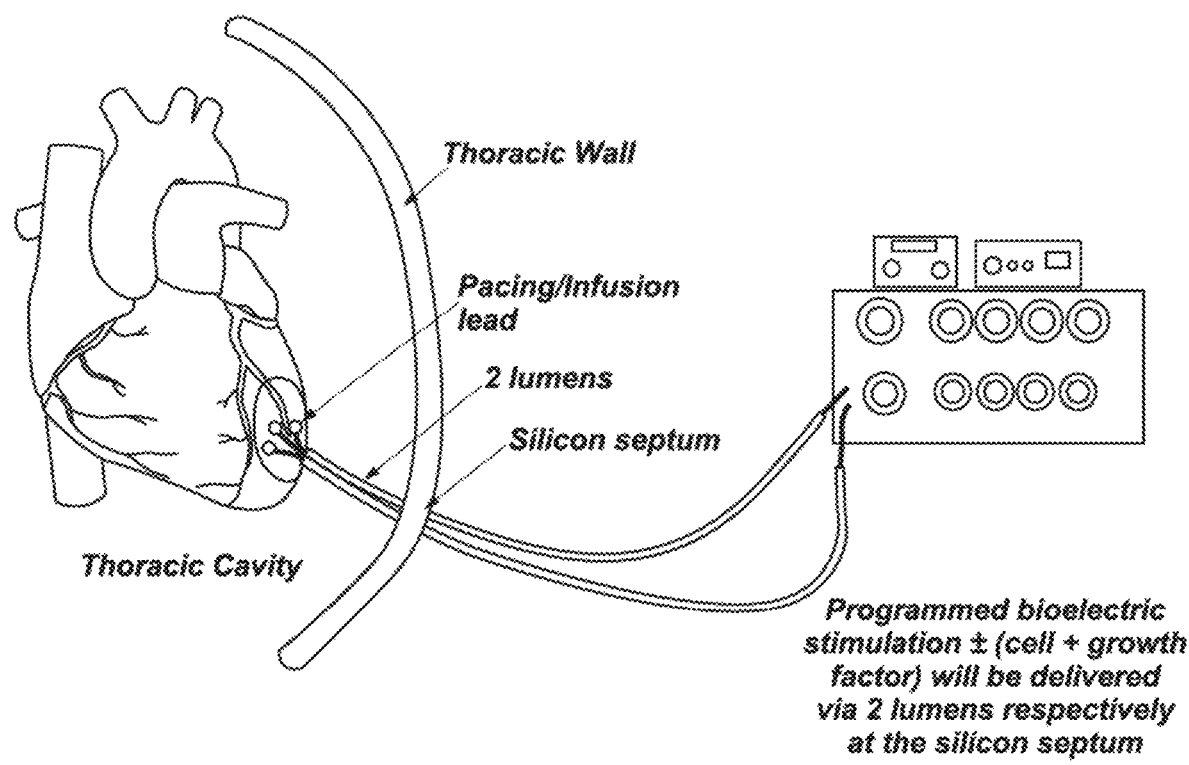
FIG. 1 depicts a programmed bioelectric stimulator (with or without cell and growth factor) for delivery to the heart of a human subject via two lumens respectively at a silicon septum.
Figure 2:
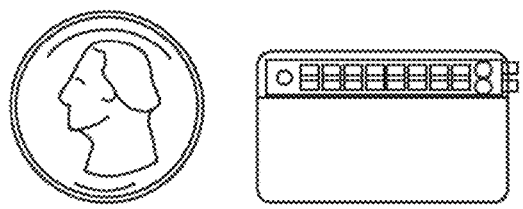
FIG. 2 depicts a programmed bioelectric stimulator depicted alongside a U.S. quarter.

Referring now to FIG. 1, depicted is a human use stimulator and pump for use with treatment of, e.g., the heart. Preferably, such a device is about the size of two quarters (available from QIG Greatbatch/Greatbatch, Inc. of Frisco, Tex., US) (FIG. 2) and is programmable and re-fillable with low cell damage design. Refilling may be by silicon septum ports and reservoir chambers. Depicted particularly in FIG. 1 are the subject's heart, the pacing lead, the infusion lead, the thoracic cavity, two lumens, thoracic wall, silicon septum, and a larger programmed/programmable bioelectric stimulator with composition (e.g., cells and growth factors) for delivery via two lumens via the silica septum. The microinfusion pump for continuous or repeat delivery of a liquid composition, which microinfusion pump includes silicon septum ports and associated reservoir chambers connected to the bioelectric stimulator microinfusion pump to the tissue with a pacing infusion lead.

The described system is currently being investigated for various applications including heart and cardiovascular (e.g., heart regeneration, aorta regeneration, biological pacemaker regeneration, heart valve regeneration, artery regeneration, limb blood flow improvement and limb salvage, and wireless diabetic foot ulcer treatment), brain (e.g., brain regeneration, stroke, concussion, Parkinson's, Alzheimer's, memory and cognitive function improvement, cerebral aneurysm treatment and cancer, and cognitive function improvement), cosmetic and personal care (e.g., breast regeneration, dental gum regeneration and tooth pulp storage, orthodontics, and skin regeneration), major organ regeneration (e.g., eye, pancreas regeneration, lung, liver regeneration, kidney regeneration, ear hearing, bladder regeneration, whole body regeneration, and sub-gastric mucosa), and associated cancer treatment (e.g., some organ specific technology platforms have integrated cancer tumor stoppage signals).

The described system may be incorporated into, for example, a whole body regeneration chamber that scans and/or analyzes the body for its deficiencies and precisely delivers the right stem cells and proteins to the right location at the right time combined with programmed infusion of whole body regeneration substances. Ultimately, the goal for the technology is whole and complete body regeneration, every organ.

The organ specific matrix is a composition comprising cells of an organ which is to be treated. The organ specific matrix is believed to aid in stem cell differentiation, but in any event is found to be useful in the composition. It has been found that for the multicomponent composition, cells plus selected growth factors are better than just cells alone. See, e.g., Procházka et al. "Therapeutic Potential of Adipose-Derived Therapeutic Factor Concentrate for Treating Critical Limb Ischemia," *Cell Transplantation,* 25(9), pp. 1623-1633(11) (2016) and "Cocktail of Factors from Fat-derived Stem Cells Shows Promise for Critical Limb Ischemia," world wide web at sciencenewsline.com/news/2016012204520017.html (Jan. 22, 2016), the contents of each of which are incorporated herein by this reference.

Figure 3:
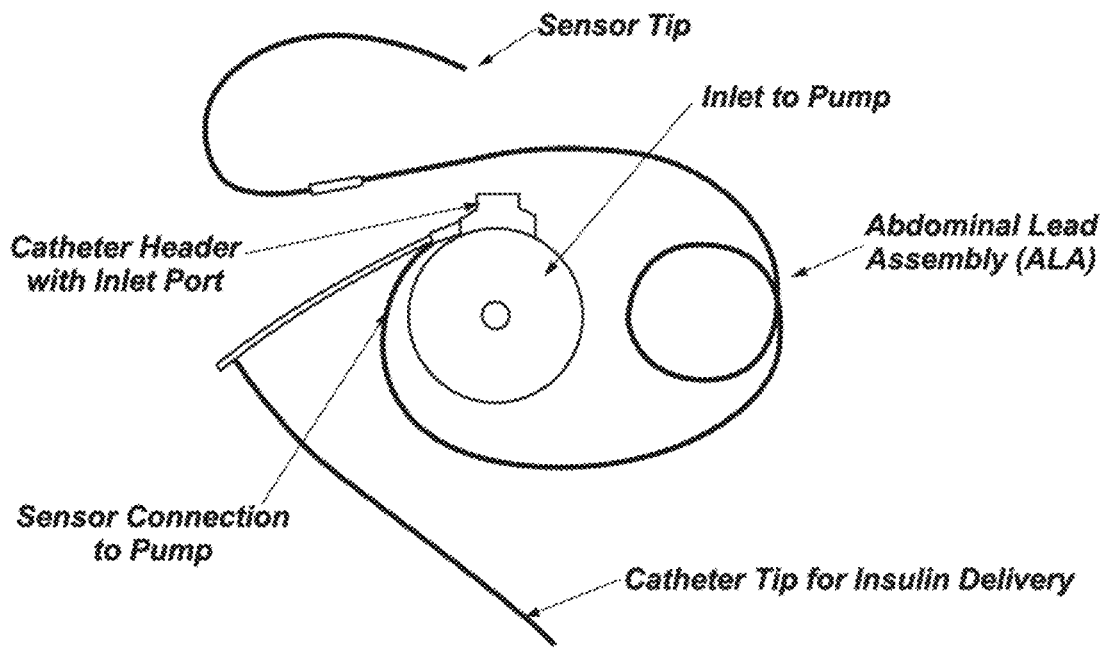
FIG. 3 depicts an interface for use with the system.
Figure 4:
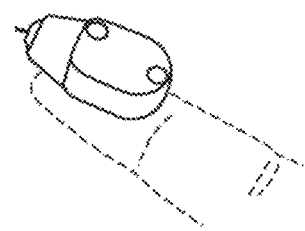
FIG. 4 depicts a micropump for use with the system.
Figure 5:
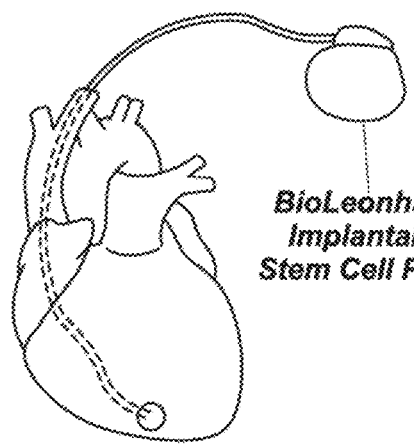
FIG. 5 depicts a pump associated with a subject's heart.

In case of an advanced disease state, a micro infusion pump (e.g., FIGS. 3-5) is used for daily delivery of, e.g., 2 ml of organ regeneration composition (comprised of adipose-derived cells or bone marrow-derived mesenchymal stem cells plus cocktail of growth factors (usually derived from amniotic fluid or placenta), selected Micro RNAs, selected alkaloids, selected anti-inflammatory agents, nutrient hydrogel, organ specific matrix, selected exosomes). For muscle regeneration, immature myoblasts are included in the composition.

Exosomes represent a specific subset of secreted membrane vesicles, which are relatively homogeneous in size (30-100 nm). Exosomes have been proposed to differ from other membrane vesicles by its size, density, and specific composition of lipids, proteins, and nucleic acids, which reflect its endocytic origin Exosomes are formed in endosomal vesicles called multivesicular endosomes (MVEs) or multivesicular bodies, which originate by direct budding of the plasma membrane into early endosomes. The generation of exosomes to form MVEs involves the lateral segregation of cargo at the delimiting membrane of an endosome and inward budding and pinching of vesicles into the endosomal lumen. Because exosomes originate by two successive invaginations from the plasma membrane, its membrane orientation is similar to the plasma membrane. Exosomes from many cell types may contain similar surface proteins as the cell from which it is derived. Membrane proteins that are known to cluster into microdomains at the plasma membrane or at endosomes, such as tetraspanins (CD63, CD81, CD82), often are also enriched in EVs. It is also thought that endosomal sorting complex responsible for transport system and tetraspanins, which are highly enriched in MVEs, play a role in exosome production. How cytosolic constituents are recruited into exosomes is unclear but may involve the association of exosomal membrane proteins with chaperones, such as HSC70, that are found in exosomes from most cell types. MVEs are also sites of miRNA-loaded RNA-induced silencing complex accumulation, and the fact that exosome-like vesicles are considerably enriched in GW182 and AGO2 implicates the functional roles of these proteins in RNA sorting to exosomes. Exosomes are released to the extracellular fluid by fusion of MVE to the plasma membrane of a cell, resulting in bursts of exosome secretion. Several Rab GTPases such as Rab 27a and Rab27b, Rab11 and Rab35, all seem to be involved in exosomes release.

Repeat doses of the composition are also preferred. See, e.g., Gavira et al. "Repeated implantation of skeletal myoblast in a swine model of chronic myocardial infarction," *Eur. Heart J.*, 31(8): 1013-1021. doi: 10.1093/eurheartj/ehp342 (2010), the contents of which are incorporated herein by this reference.

For heart muscle regeneration, immature myoblasts and cardiac-derived progenitors cells as well as endothelial progenitor cells (EPCs) may be included in the composition.

Generally, the system hereof involves a bioelectric stimulator controlling expression and/or release of SDF-1, IGF-1, HGF, EGF, VEGF, PDGF, eNOS, follistatin, Activin A and B, and tropoelastin. Optionally and in certain applications, GDF-10, GDF-11, Neurogenin-3 and Relaxin may also be included.

SDF-1 is generally for recruiting stem cells and maturing blood vessels. IGF-1 is for DNA repair. HGF is for tissue regeneration and reduces arrhythmias in the case of heart. EGF grows tissue. VEGF grows blood vessels. PDGF is a second stem cell homing factor and helps tissue regeneration especially heart. eNOS dilates blood vessels. Follistatin promotes muscle growth. Activin A and B regenerates nerve cells and neurons. tropoelastin increases elasticity of all tissues especially arteries, skin, heart, aorta. GDF-10 and GDF-11 promote regeneration especially of nerve cells and neurons. Neurogenin-3 is especially helpful in brain and pancreas regeneration. Relaxin helps heart regeneration.

The micro voltage signal generator may be produced utilizing the same techniques to produce a standard heart pacemaker well known to a person of ordinary skill in the art. An exemplary microvoltage generator is available (for experimental purposes from Cal-X Stars Business Accelerator, Inc. DBA Leonhardt's Launchpads or Leonhardt Vineyards LLC DBA Leonhardt Ventures of Salt Lake City, Utah, US). The primary difference is the special electrical stimulation signals needed to control, e.g., precise follistatin expression and/or release on demand (which signals are described later herein). The leading pacemaker manufacturers are Medtronic, Boston Scientific Guidant, Abbott St. Jude, BioTronik and Sorin Biomedica.

Construction of the electric signal generators and pacemakers, are known in the art and can be obtained from OEM suppliers as well as their accompanying chargers and programmers. The electric signal generators are programmed to produce specific signals to lead to specific protein expressions at precisely the right time for, e.g., optimal organ treatment or regeneration.

The pacing infusion lead may be constructed or purchased from the same suppliers that build standard heart pacemaker leads. Pacing infusion leads may be purchased from a variety of OEM vendors. The pacing infusion lead may, for example, be a standard one currently used in heart failure pacing studies in combination with drug delivery.

An infusion and electrode wide area pitch may be constructed by cutting conduction polymer to shape and forming plastic into a flat bag with outlet ports in strategic locations.

Micro stimulators may be purchased or constructed in the same manner heart pacemakers have been made since the 1960's. Micro infusion pumps can be purchased or produced similar to how they have been produced for drug, insulin, and pain medication delivery since the 1970's. The programming computer can be standard laptop computer. The programming wand customary to wireless programming wands may be used to program heart pacers.

Any one of the protein expression signals work well on their own for organ regeneration, but they work better together. SDF-1 is the most powerful regeneration protein followed by IGF-1.

Wireless, single lumen infusion pacing lead or infusion conduction wide array patch may all be used to deliver the regeneration signals and substances to the organ of interest to be treated or they may be used in combination.

A re-charging wand for use herein is preferably similar to the pacemaker re-charging wand developed by Alfred Mann in the early 1970's for recharging externally implantable pacemakers.

Figure 21:
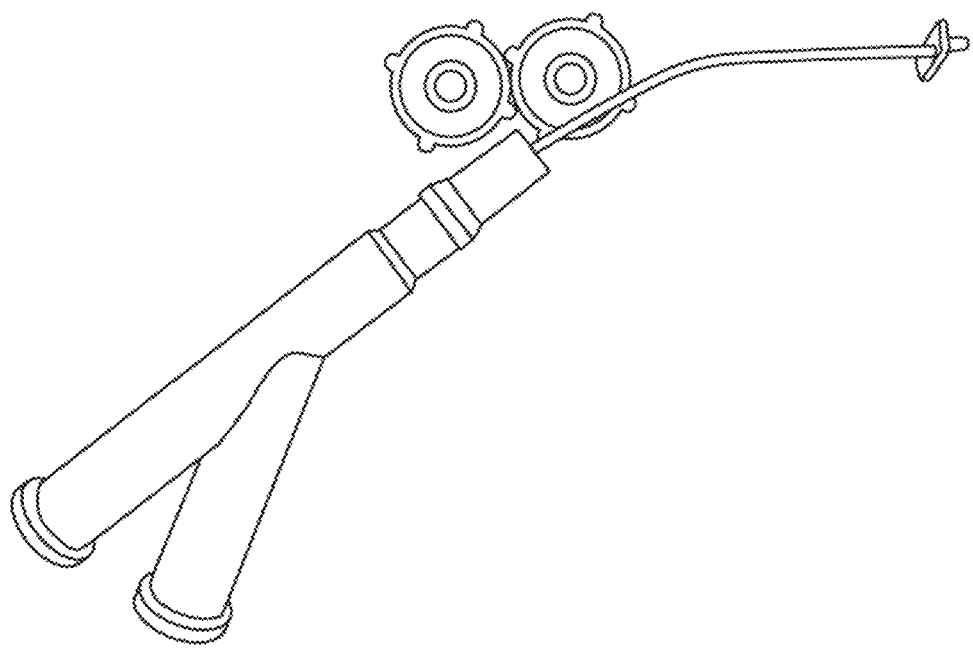
FIG. 21 depicts a combination bioelectric stimulation and stem cells and growth factors infusion catheter.

FIG. 21 depicts a combination bioelectric stimulation and stem cell and growth factor(s) infusion catheter usable with the described system.

Figure 22:
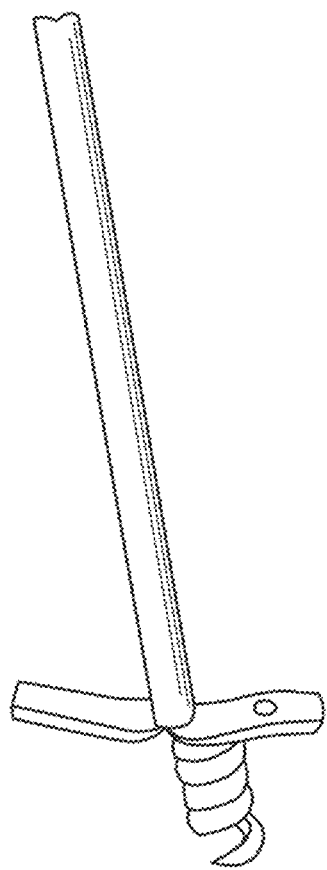
FIG. 22 is a close up view of the conductive and infusion cork screw tip for use with the catheter system of FIG. 21.

A corkscrew tip may be of a standard type utilized to secure most heart pacemakers in heart tissue. Wireless delivery of the signal or electro-acupuncture needle delivery is included. FIG. 22 is a close up of the conductive and infusion cork screw tip for getting deep into target tissue. The tip include suture tabs for even more secure fixation to the target organ.

Additionally, the micro stimulator and micro pump and regeneration composition and bioelectric signaling programming may be used to generate tissue(s) and/or organ(s).

A preferred composition includes adipose-derived cells (or bone marrow derived MSCs or any pluripotent stem cell, such as iPS cells) and growth factor mix which should include (SDF-1, IGF-1, EGF, HGF, PDGF, VEGF, eNOS, activin A, activin B, follistatin, relaxin, GDF-10, GDF-11 and tropoelastin plus selected exosomes (miR-146a, miR-294, mES-Exo) plus selected alkaloids (harmine and tetrahydroharmine) plus selected anti-inflammatory factors plus nutrient hydrogel (IGF-1, SDF-1, HGF plus FGF) plus organ specific matrix. For regenerating muscle, one includes into the composition skeletal muscle or cardiac muscle-derived cells. Also, preferably included are amniotic fluid, placenta, or cord blood when available.

For heart treatment/regeneration (e.g., for treating congestive heart failure), the compositions may be modified to include: cardiac tissue biopsy derived cells, adipose tissue-derived cells, skeletal muscle derived cells (immature myoblasts (Tamaki selection process—Tamaki et al. "Cardiomyocyte Formation by Skeletal Muscle-Derived Multi-Myogenic Stem Cells after Transplantation into Infarcted Myocardium," *PLoS ONE* 3(3): e1789. doi:10.1371/journal.pone.0001789 (2008), the contents of which are incorporated herein by this reference)), nutrient hydrogel, selected growth factors (SDF-1, PDGF, HGF, IGF-1, follistatin, relaxin, tropoelastin, eNOS, VEGF, and EGF), exosomes, alkaloids, anti-inflammatory agent(s), cardiac matrix soaked in selected growth factors, and Micro RNAs.

For human use, longer repeat doses are needed and a natural expression and/or release from a patient's own electrically stimulated cells leads to successful human heart regeneration. For example, the described signals for follistatin expression and/or release match more closely with the natural low voltage signals in the human body.

In a booster composition for heart treatment/regeneration, the composition may include: adipose tissue-derived cells, cardiac tissue-derived cells, skeletal muscle derived cells-immature myoblasts (Tamaki selection process—cardiac progenitor—Tamaki et al. supra (2008)), growth factors (SDF-1, PDGF, HGF, Follistatin, and IGF-1), and cardiac matrix. In the basic composition for heart treatment/regeneration, the composition may include: adipose tissue-derived cells and muscle-derived immature myoblast cells (Tamaki process selection—see Tamaki et al. supra (2008)) or cardiac derived cells, together with selected growth factors (SDF-1, PDGF, HGF, and Follistatin).

There are three compositions, i.e., a basic composition, an intermediate composition, and an advanced composition. The basic composition includes MSCs or adipose derived cells, amniotic fluid, and myoblasts. The intermediate composition includes the ingredients of the basic composition together with a cocktail of growth factors (Follistatin rich). The advanced composition is adipose-derived or bone marrow-derived stem cells (MSCs), endothelial progenitor cells, selected growth factors cocktail, selected exosomes, selected Micro RNAs, selected alkaloids, selected anti-inflammatory agents, nutrient hydrogel, organ specific matrix, amniotic fluid (240 growth factors), and cardiac derived cells or immature myoblasts.

The concentration of cells in the compositions is preferably about 50,000,000 cells/ml. The amniotic fluid is preferably as described in Pierce et al. "Collection and characterization of amniotic fluid from scheduled C-section deliveries," *Cell Tissue Bank*, DOI 10.1007/s10561-016-9572-7 (Springer, 2012) and is available from Irvine Scientific.

In certain embodiments, an organ regeneration mixed composition (e.g., a cardio angiogenic and cardio myogenic "cocktail" for heart treatment/regeneration) is loaded into a micro infusion pump (or in the case of limb salvage injected directly in the patient's leg with a needle and syringe). The pump may be refilled, e.g., weekly to achieve a slow, timed infusion delivery of the composition to the heart scar tissue. Administration of the composition(s) is combined with bioelectric stimulation to control the expression and/or release of more than twelve regeneration promoting proteins. Treatment times for assisting the heart may last 36 months.

For treating heart failure, a single (prior art) injection session is insufficient to fully recover a failing organ especially a failing heart. Furthermore, injecting just one cell type alone one time is not enough for full organ recovery. Bioelectric stimulation for controlled expression and/or release of SDF-1 in a subject is powerful to improve organ regeneration results. Bioelectric stimulation controlled expression and/or release of VEGF, eNOS and SDF-1 is powerful in improving blood flow to a failing organ. Nutrient hydrogels and organ specific matrixes can highly improve cell transplantation results. A mix of growth factors provides better organ recovery results than just one growth factor or just one cell type. Bioelectric stimulation controlled expression and/or release of a variety of growth factors offers more improvement than just one. Hepatocyte growth factor not only aides in organ regeneration, but also reduces arrhythmias risk in the heart. Follistatin injected or released via bioelectric stimulation can greatly improve muscle based organ regeneration results. Tropoelastin can improve elasticity of any treated organ, which in itself is valuable and is deemed to be especially valuable in the heart. An implantable micro infusion re-fillable programmable pump designed to reduce cell damage is better than injecting the patient's heart numerous times with separate procedures.

Bioelectric stimulation can be done with the described microstimulator, which has a pacing infusion lead with a corkscrew lead placed/attached at, e.g., the center of heart scar tissue. The microstimulator is actuated and runs through programmed signals to signal the expression and/or release of, e.g., SDF-1 and a differentiation signal. Described is a method of activating a tissue to differentiate a stem cell or to stimulate the tissue to produce a protein. The protein is selected from the group consisting of insulin-like growth factor 1 ("IGF1"), epidermal growth factor ("EGF"), hepatocyte growth factor ("HGF"), platelet-derived growth factor ("PDGF"), endothelial NOS ("eNOS"), vascular endothelial growth factor ("VEGF"), activin A, activin B, receptor activator of nuclear factor kappa-B ligand ("RANKL"), osteoprotegerin ("OPG"), tumor necrosis factor alpha ("TNF α"), follistatin, interleukin 6 ("IL-6"), hypoxia-inducible factor 1-alpha ("HIF-1-α"), and tropoelastin, the method including: stimulating the, e.g., human tissue with an electrical signal appropriate for the protein and tissue.

In such a method, when the electrical signal includes (within 15%): 0.1 V applied at a frequency of about 50 Hz with a duration of about three (3) minutes (wherein the electrical signal is as measured three (3) mm deep into the tissue), the protein produced is VEGF.

In such a method, when the electrical signal includes (within 2%): 200 picoamps for about 10 seconds for about one (1) hour and the pulse has an amplitude of about 5 volts and a width of about 0.5 milliseconds for about one (1) hour, with a duration of about one (1) minute (wherein the electrical signal is as measured three (3) mm deep into the tissue), stem cells differentiate.

In such a method, when the electrical signal includes (within 15%): 10 V at 50 Hz and 100 Hz for about 12 hours each (duration one (1) minute) (wherein the electrical signal is as measured three (3) mm deep into the tissue), the protein produced is follistatin.

In such a method, when the electrical signal includes (within 15%): 3.5 V stimulation in 10 second bursts, one (1) burst every 30 seconds at a frequency of about 50 Hz (duration 5 minutes) (wherein the electrical signal is as measured three (3) mm deep into the tissue), the protein produced is HGF.

In such a method, when the electrical signal includes (within 15%): 3 mv with a frequency of about 22 Hz, and a current of about one (1) mA for about fifteen (15) minutes and 3 ma for about fifteen (15) minutes (duration 5 minutes) (wherein the electrical signal is as measured three (3) mm deep into the tissue), the protein produced is IGF-1.

In such a method, when the electrical signal includes (within 15%): 0.06 V with 50 Hz alternating electrical field and a current of about 1 mA for about fifteen (15) minutes and 3 mA for about fifteen (15) minutes (duration 2 minutes) (wherein the electrical signal is as measured three (3) mm deep into the tissue), the protein produced is tropoelastin.

In such a method, when the electrical signal includes (within 15%): alternating high-frequency (HF) and medium-frequency signals (MF), symmetric, biphasic, trapezoid pulses, with 400-µs pulse duration and 1.5/1-s ramp-up/ramp-down duration, respectively (wherein the electrical signal is as measured three (3) mm deep into the tissue), the protein produced is eNOS. In such a method, when the HF consists of about 75 Hz pulses with six (6) seconds on and 21 seconds off for about fifteen (15) minutes. In such a method, when the MF consists of about 45 Hz pulses with 5 seconds on 12 seconds off for about fifteen (15) minutes followed by stimulation duration set as 20 minutes. In such a method, when the electrical signal includes (within 15%): one (1) Hz stimulation, stimulation applied for about nine (9) seconds, followed by a one (1) second silent period, a total of about 1080 stimulations for about 20 minutes. In such a method, when the electrical signal includes (within 15%): 20 Hz stimulation, stimulation applied for about two (2) seconds, followed by silent period for about 28 seconds, a total of about 1600 stimulations for about 20 minutes (duration 2 minutes).

In such a method, when the electrical signal includes (within 15%): 6 mv at 150 HZ Monophasic square wave pulse 0.1 ms in duration current of fifteen (15) mA for about fifteen (15) minutes (duration two (2) minutes) (wherein the electrical signal is as measured three (3) mm deep into the tissue), the protein produced is Activin B.

In such a method, when the electrical signal includes (within 15%): 10 V/cm, pulse-width 180 µs, 500 Hz (duration nine (9) minutes) (wherein the electrical signal is as measured three (3) mm deep into the tissue), the protein produced is EGF.

For example, up-regulation of RANKL, IGF-1, VEGF, and SDF-1 was achieved in cardiomyoctyes using such signals. Up-regulation of SDF-1 was achieved in pig heart. Up-regulation of VEGF, endothelial NOS ("eNOS"), hypoxia-inducible factor 1-alpha ("HIF-1-α"), and IL-6 was achieved in eye cells. Up-regulation of RANKL and osteoprotegerin ("OPG") was achieved in bone, tooth and gum.

Also described is a method of activating a tissue to produce SDF1, the method including: stimulating the (e.g., human) tissue with an electrical signal, wherein the electrical signal includes (within 15%): 30 pulses per second with a voltage of about 3.5 mV, and successively alternating currents of about 700 to 1500 picoamps for about one minute, and again with 700 to 1500 picoamps for about one minute and stimulated with current of about 0.25 mA, pulse duration of about 40 pulses/s, pulse width of about 100 µs, wherein the electrical signal is as measured three (3) mm deep into the tissue.

Further described is a method of activating a tissue to attract a stem cell, the method including: stimulating the (e.g., human) tissue with an electrical signal, wherein the electrical signal includes (within 2%): fifteen (15) mV and a current of about 500 picoamps at 70 pulses per minute for about three (3) hours and 20 pulses per minute, a pulse amplitude of from about 2.5-6 volts, and a pulse width of from about 0.2-0.7 milliseconds for about three (3) hours for about three (3) minutes, wherein the electrical signal is as measured three (3) mm deep into the tissue.

A combination bioelectric stimulator that controls expression and/or release in the scarred heart of SDF-1, IGF-1, HGF, EGF, eNOS, VEGF, Activin A and B, follistatin, tropoelastin, GDF-10, GDF-11 and Neurogenin 3 combined with repeat delivery of a mixed stem cell and growth factor cardiac matrix composition via an implantable re-fillable micro infusion pump may be advantageously used.

In some cases, SDF-1 recruits via a presumed homing signal new reparative stem cells to the damaged organ. VEGF causes new nutrient and oxygen producing blood vessels to grow into the area being treated. IGF-1 repairs damaged cells, tissues and organs. Follistatin repairs damaged muscle. Tropoelastin adds elasticity to treated tissues making them more compliant. HGF aides in all repair processes and in the specific case of the heart regeneration reduces the risk of arrhythmias. All of these proteins work together to fully regenerate an organ over time.

The healing process can be accelerated with the use of a micro infusion pump that is filled with various types of stem cells and growth factors and in some cases drugs.

In certain embodiments relating to the treatment of cancer and tumors, described is a method of inhibiting the growth of cancer cells in a target region, wherein the method includes treating the cancer cells with an anti-cancer drug; and applying an electric field to the target region for a period of time, wherein the electric field has frequency and field strength characteristics selected to inhibit the growth of cancer cells in the target region. In such a method, in the applying step, the field may be applied in at least two different directions in an alternating sequence.

In such a method, the drug dosage may be less than 20% of a standard dosage for the drug.

In such a method, the period of time is typically at least 24 hours.

In such a method, the field strength is typically at least one (1) V/cm.

In such a method, the drug typically comprises at least one of paclitaxel, doxorubicin cyclophosphamide, and cisplatin.

In such a method, the field strength is typically at least one (1) V/cm and the period of time is at least 24 hours.

Also described in certain embodiments is a method of killing or inhibiting the growth of cancer cells in a target region, wherein the method includes applying an electric field to the target region for a period of time while the cancer cells are being treated with an anti-cancer drug, wherein the electric field has a field strength in the target region of at least one (1) V/cm. In such a method, the drug dosage is less than 20% of a standard dosage for the drug. In such a method, the period of time is at least 24 hours. In such a method, the drug comprises at least one of paclitaxel, doxorubicin cyclophosphamide, and cisplatin. In such a method, the field strength is between one (1) V/cm and 5 V/cm and the period of time is at least 24 hours. In such a method, in the applying step, the field is applied in at least two different directions in an alternating sequence. Typically, the drug comprises cyclophosphamide, and typically, the period of time is at least 6 hours.

What follows are preferred signals from the stimulator. For example, described are two PDGF expression control signals, one low voltage and one higher voltage. The test tissue is sheep heart tissue. The test cells are mesenchymal stem cells.

30% PDGF increase >3 V/cm, 10 Hz, 2 micro amps (0.000002 amps) and the pulse duration 0.2 ms.

230% PDGF increase >20 V/cm 100 Hz, 0.25 mA (2.5e-7 amps) and pulse duration of 40 pulses/s, width of 100 µs.

40 minute treatment cycles 2 times a week for 4 weeks and then 3 times a week for 12 weeks.

PDGF Signal: 20 V for one (1) minute, 20 MVs for 10 minutes, current of 0.25 mA, pulse duration of 40 pulses/s, pulse width of 100 µs, and frequency of 100 Hz for 5 minutes followed by 528 Hz for 3 minutes and 432 Hz for 3 minutes and 50 Hz for 3 minutes.

VEGF—Blood vessel sprouting growth: 0.1 V applied at a frequency of 50 Hz. Duration 3 minutes.

SDF-1—Stem cell recruiting signal: 30 pulses per second with a voltage of 3.5 mV, and successively alternating currents of 700 to 1500 picoamps for one minute, and again with 700 to 1500 picoamps for one minute and stimulated with current of 0.25 mA, pulse duration of 40 pulses/s, pulse width of 100 µs, and frequency of 100 Hz—each signal for 40 minutes to 8 hours a day for 2 to 36 months as needed for ideal results. Duration 7 minutes.

Stem cell proliferation signals: 15 mV and a current of 500 picoamps at 70 pulses per minute for 3 hours and 20 pulses per minute, a pulse amplitude of from 2.5-6 volts, and a pulse width of from 0.2-0.7 milliseconds for 3 hours. Duration 3 minutes.

Stem cell differentiation signals to become muscle: 200 picoamps for 10 seconds for one (1) hour and the pulse has an amplitude of 5 volts and a width of 0.5 milliseconds for one (1) hour. Duration one (1) minute.

Another method is to reverse polarity and drop the voltage.

Follistatin—(muscle growth) production signal: 10 V at 50 Hz and 100 Hz at 0.25 mA. Duration one (1) minute.

HGF—Hepatocyte growth factor (arrhythmia reduction) signal: 3.5 V stimulation in 10 second bursts, one (1) burst every 30 seconds at frequency 50 Hz. Duration 5 minutes.

IGF-1: 3 mV with electric frequency of 22 Hz, and electric current of one (1) mA for 15 minutes and 3 mA for 15 minutes. Duration 5 minutes.

Tropoelastin: 0.06 V with 50 Hz alternating electrical field and electric current of 1 mA for 15 minutes and 3 mA for 15 minutes. Duration 2 minutes.

RANKL/TNF-α, nuclear factor-kappa B (NF-κB) ligand/TNF-α: 3 mV at 2/100 Hz alternating frequency with current of 3 mA followed by 15 Hz, one (1) Gauss EM field, consisting of 5-millisecond bursts with 5-microsecond pulses followed by 200-µs pulse duration at 30 Hz and with current amplitude of 140 mA. (Optional use depending on application.)

eNOS: Alternating high-frequency (HF) and medium-frequency signals (MF): Symmetric, biphasic, trapezoid pulses, with 400-µs pulse duration and 1.5/1-s ramp-up/ramp-down duration, respectively. HF consisted of 75 Hz pulses with 6 second on-21 second off for 15 minutes. MF consisted of 45 Hz pulses with 5 second on-12 second off for 15 minutes. Followed by stimulation duration set as 20 minutes for both one (1) Hz and 20 Hz stimulations. For one (1) Hz stimulation, stimulation is applied for 9 seconds, followed by a one (1) second silent period, a total of 1080 stimulations for 20 min. For 20 Hz stimulation, stimulation is applied for 2 seconds, followed by silent period for 28 seconds, a total of 1600 stimulations for 20 min. Duration 2 minutes.

Activin B: 6 mV at 150 Hz Monophasic square wave pulse 0.1 ms in duration current of 15 mA for 15 minutes. Duration 2 minutes.

EGF—10 V/cm, pulse-width 180 µs, 500 Hz. Duration 9 minutes.

An exemplary bioelectric signal sequence suggested for heart regeneration in humans split into six phases is as follows.

Phase—Prepare Scar ("soil prep"): 10 minutes
IGF-1 signal 3 minutes
PDGF signal 3 minutes
HGF signal 2 minutes
EGF signal 2 minutes
Phase II—Grow New Blood Vessels ("lay irrigation system"): 5 minutes
VEGF signal-3 minutes
SDF-1 signal-one (1) minute
eNOS signal-one (1) minute
Phase III—Recruit and Inject Stem Cells ("plant"): 15 minutes
SDF-1 signal-10 minutes
PDGF-1 signal 5 minutes
Phase IV—Build Tissue ("grow"): 25 minutes
Stem Cell Proliferation Signal-5 minutes
Stem Cell Differentiation Signal-5 minutes
Follistatin Signal-5 minutes
Tropoelastin Signal-5 minutes
GDF-10-2 minutes
GDF-11-3 minutes
Phase V—Post Tissue Growth Maintenance ("fertilize"): 30 minutes
VEGF-3 minutes
EGF-2 minutes
eNOS-2 minutes
HGF-5 minutes
PDGF-3 minutes
Tropoelastin-5 minutes
Relaxin-5 minutes
Follistatin-5 minutes
Phase VI—Protect Against Enemies ("pesticides"): 10 minutes
Activin A and B-5 minutes
IGF-1-5 minutes Results of Electrical Stimulation (ES) of Cells In Vitro IL-1β: mRNA expression was up-regulated from 16 up to more than 400 times when cells were treated with 10 to 20 V between 3 and 20 hours.

IL-6: mRNA expression was up-regulated from 3 times—as soon as 15 minutes—to 10 times.

IL-8: mRNA expression was stimulated by 5 to 50 times.

HGF: mRNA expression was up-regulated by more than 10 times.

TNFα: mRNA expression was up-regulated by 9 to 24 times.

MMP9: mRNA expression was up-regulated 9 to 23 times with 3 and 24 hours of ES, respectively.

CCL2: mRNA expression was up-regulated 15 to 64 times.

CXCL5: mRNA expression up-regulated thousands of times.

CXCL10: mRNA expression up-regulated a thousand times by long term, 24 hour, electrical stimulation in vitro. These experiments were performed on adipose derived stem cells (among other cell types).

A week after treatment, samples can be collected for morphometric evaluation by in-situ hybridization or RT-PCR.

The PCR machine used herein to detect protein expression was the Applied Biosystems 7900HT.

FIGS. 6-20 are images of the corresponding signals with the name, voltage, and frequency of each signal written on each image. eNOS and differentiation signals were omitted due to of complexity or lack of frequency parameters. The signals are to be further defined in terms of current and frequency, not voltage and frequency as shown. The voltage delivered to the cells will be different for each tissue type, but with current all of the signals can be kept constant regardless of tissue type. The device should have a current driven signal (instead of voltage driven like most other devices).

Figure 6:
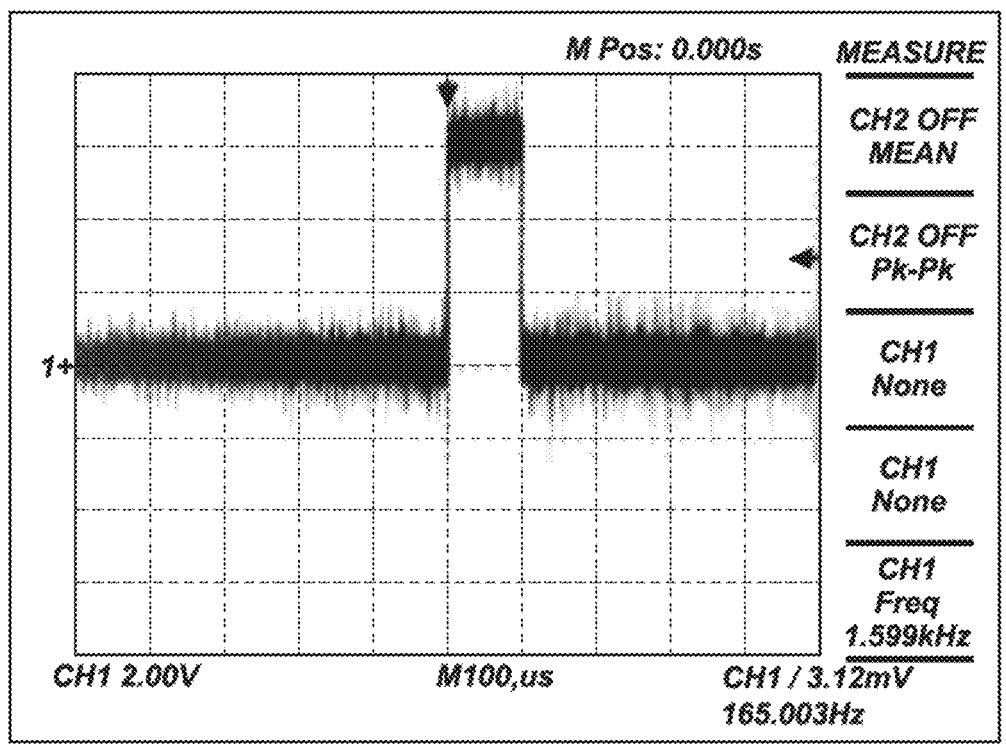
FIG. 6 depicts an image of the signal (voltage and frequency) associated with Activin B at 6.0 mV, pulse width 100 μs, square wave.
Figure 7:
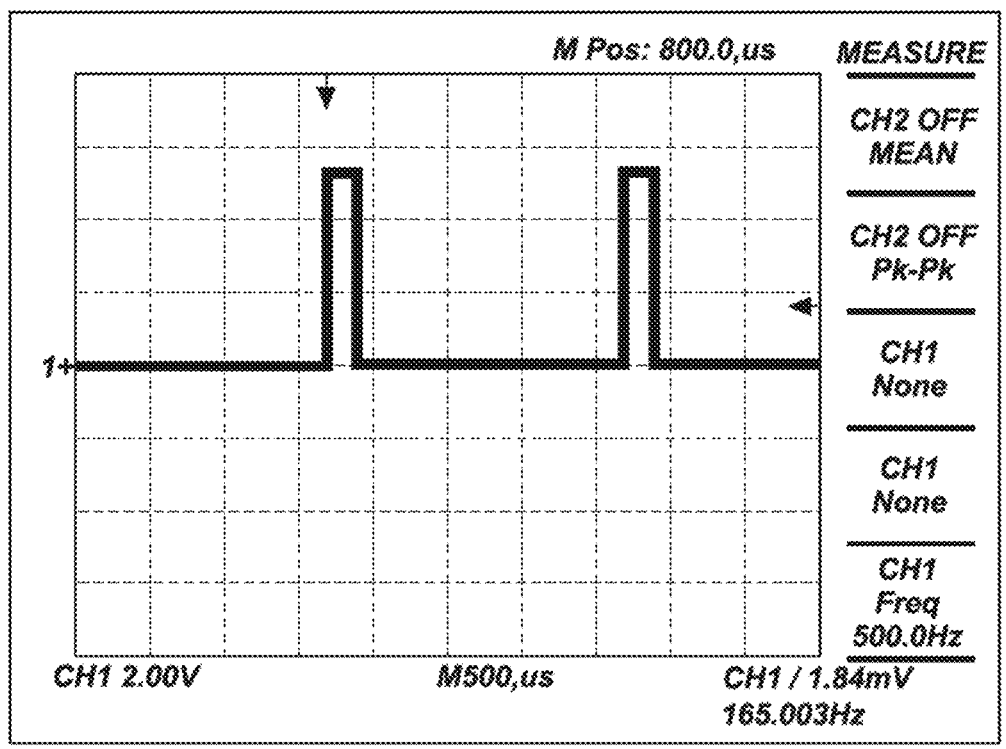
FIG. 7 depicts an image of the signal (voltage and frequency) associated with EGF at 10 V/cm (5 V here), 500 Hz, pulse width 180 μs, square wave.
Figure 8:
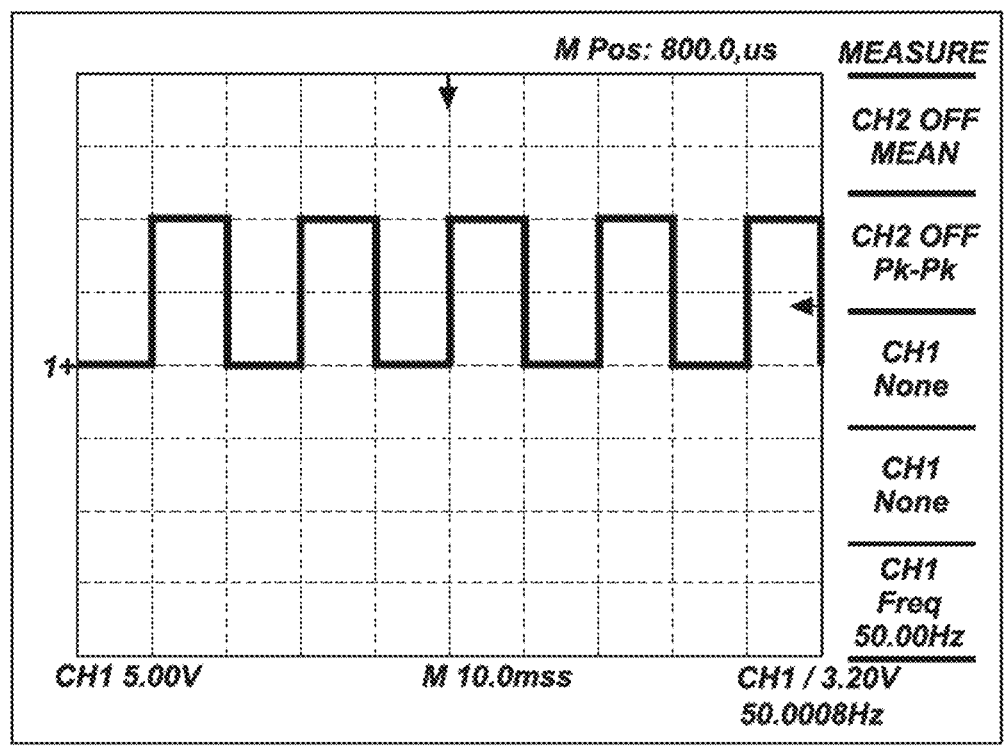
FIG. 8 depicts an image of the signal (voltage and frequency) associated with follistatin at 10 V/cm, 50 Hz, square wave.
Figure 9:
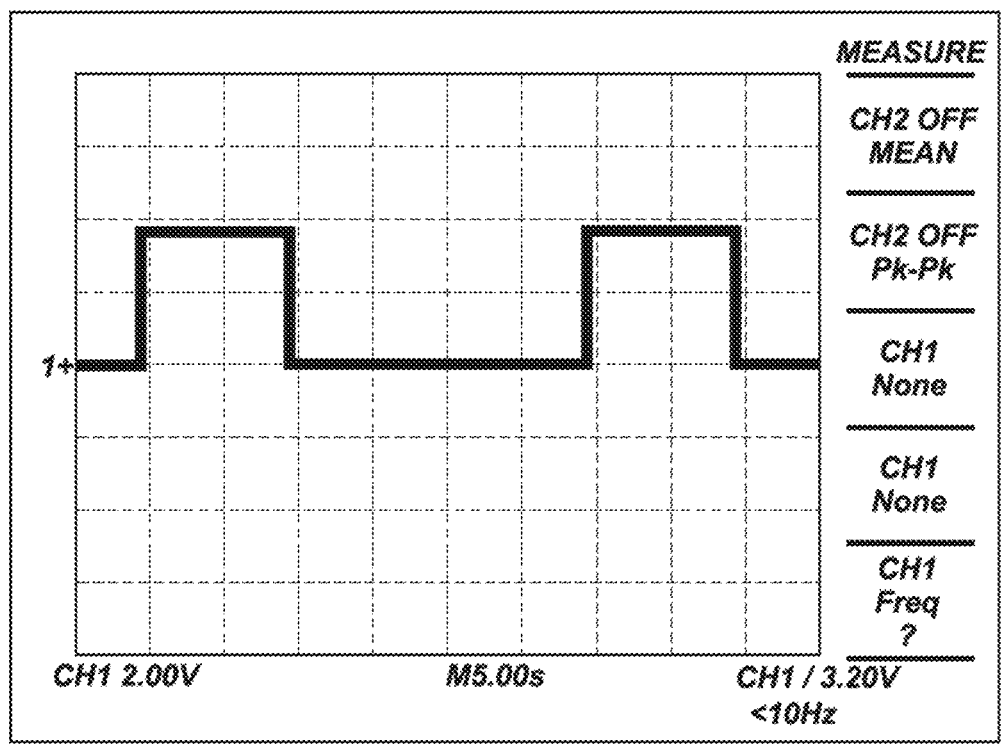
FIG. 9 depicts an image of the signal (voltage and frequency) associated with HGF at 3.5 V, 10 second burst every 30 seconds, square wave.
Figure 10:
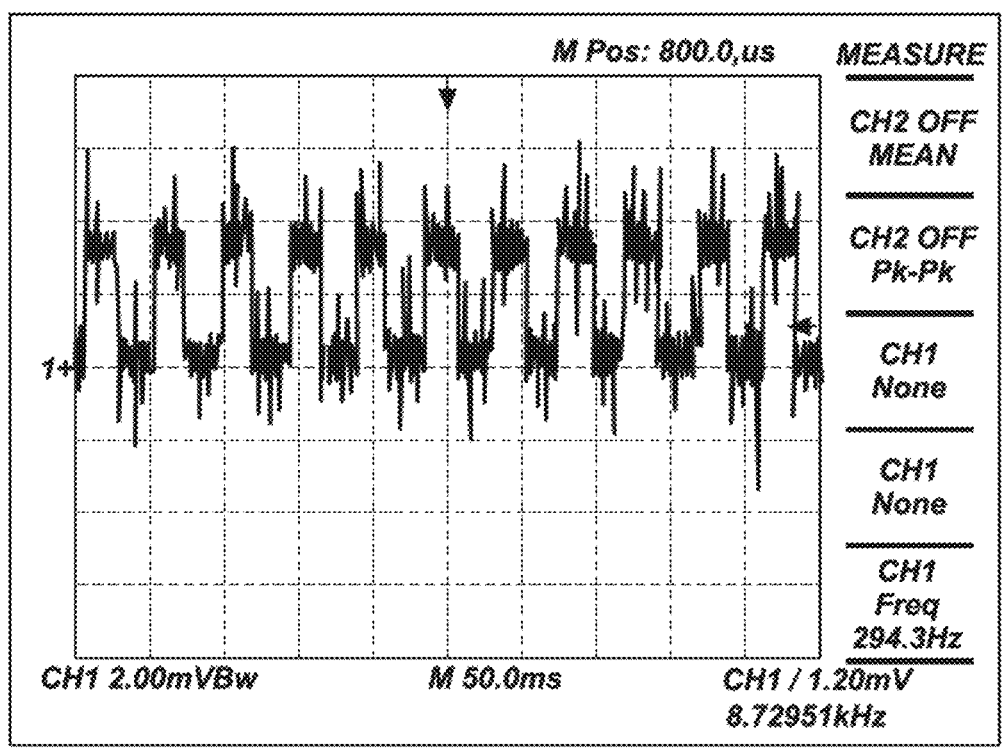
FIG. 10 depicts an image of the signal (voltage and frequency) associated with IGF-1: 3.0 mV, 22 Hz, square wave.
Figure 11:
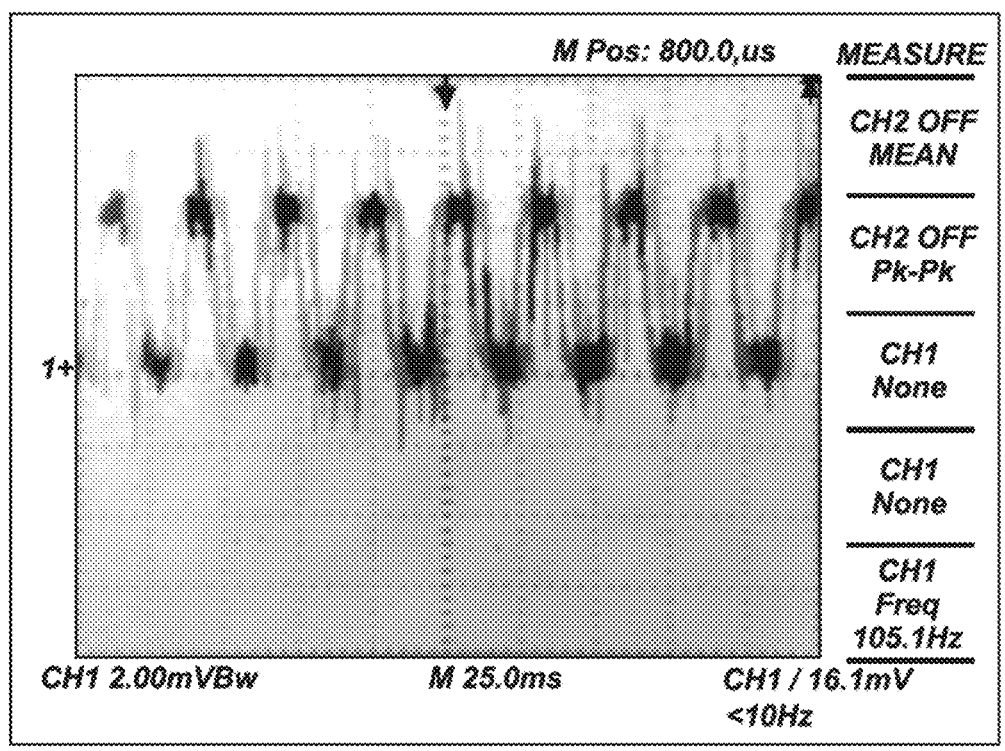
FIG. 11 depicts an image of the signal (voltage and frequency) associated with OPG: 4.0 mV, 2,000 Hz, square wave.
Figure 12:
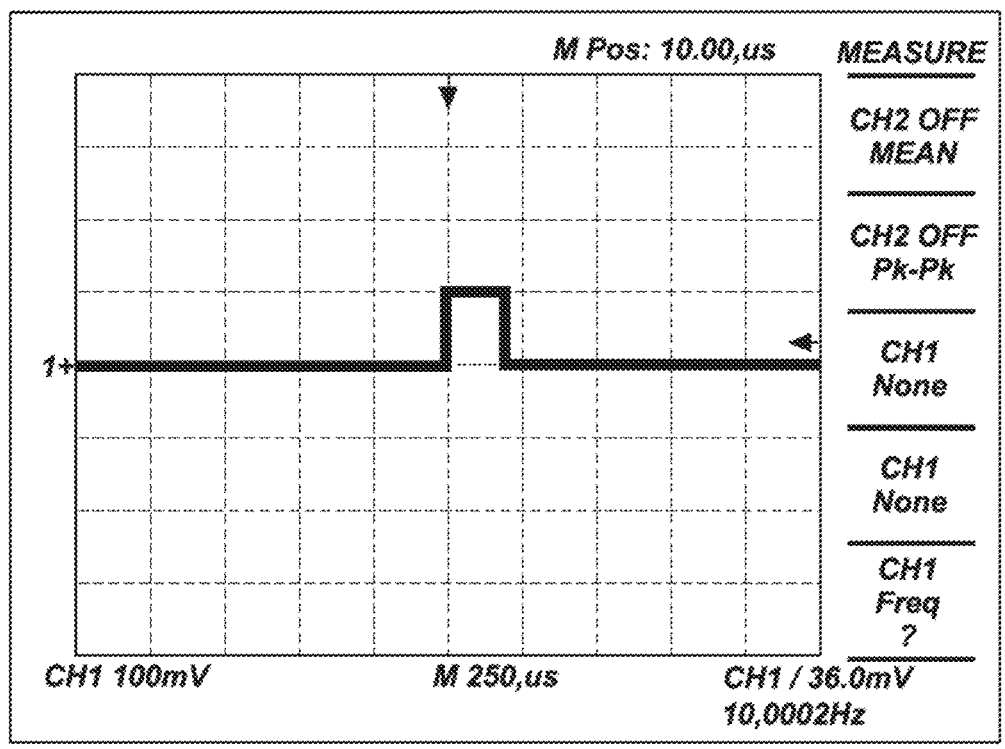
FIG. 12 depicts an image of the signal (voltage and frequency) associated with PDGF 30%: 3 V/cm (100 mV here), 10 Hz, pulse width 200 µs, square wave.
Figure 13:
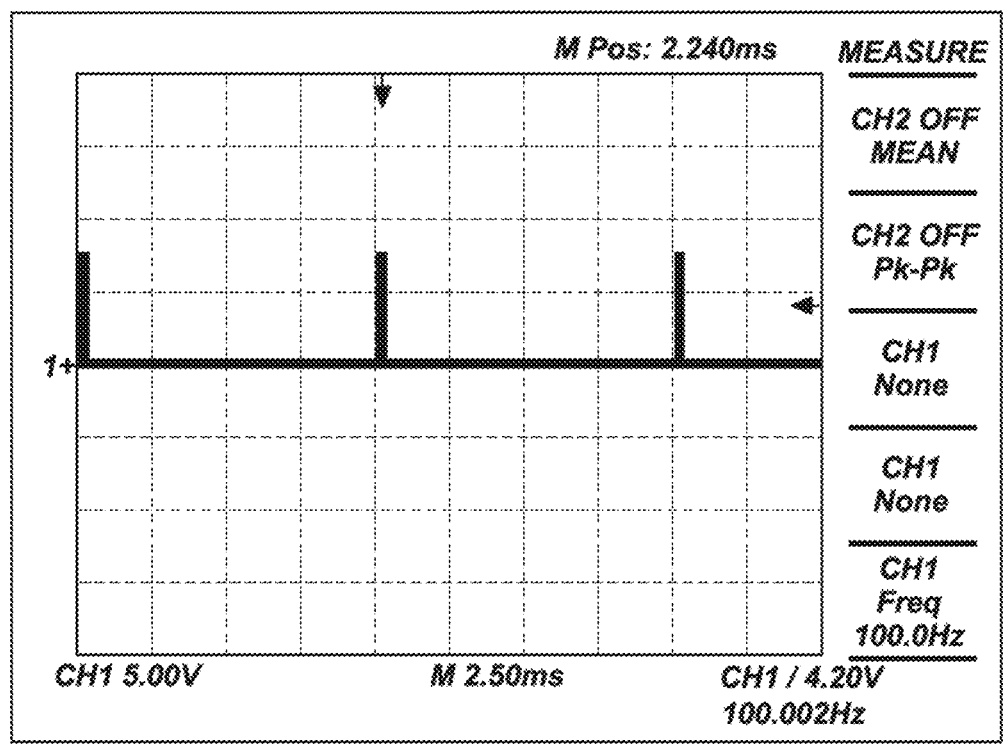
FIG. 13 depicts an image of the signal (voltage and frequency) associated with PDGF 230%: 20 V/cm (7.0 V here), 100 Hz, pulse width 100 µs, square wave.
Figure 14:
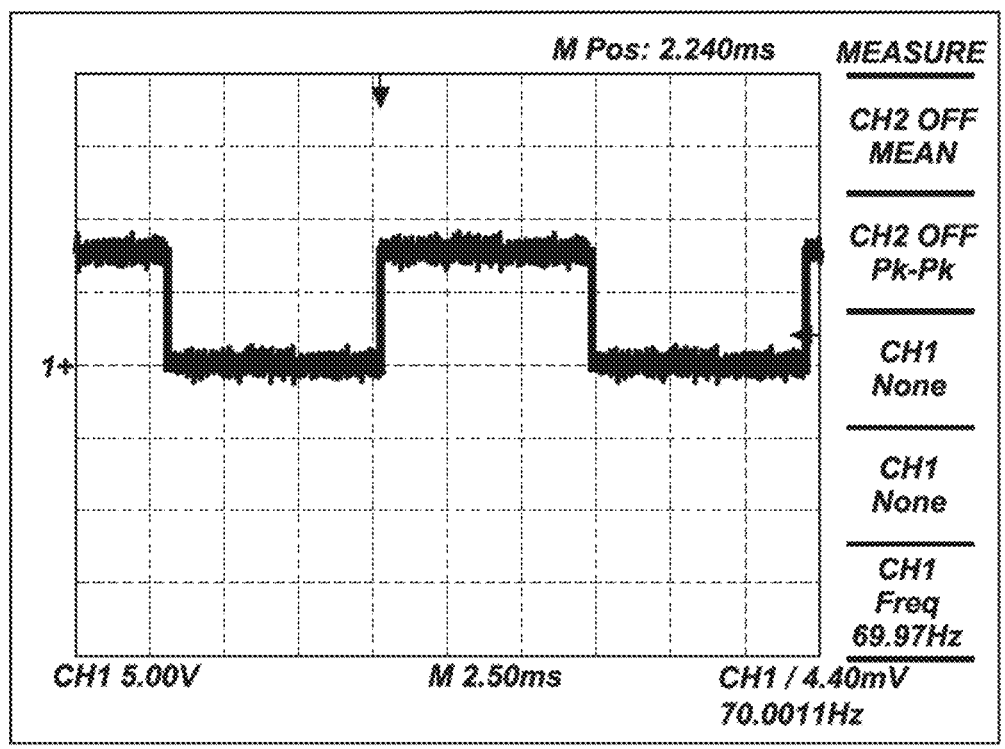
FIG. 14 depicts an image of the signal (voltage and frequency) associated with proliferation: 15 mV, 70 Hz, square wave.
Figure 15:
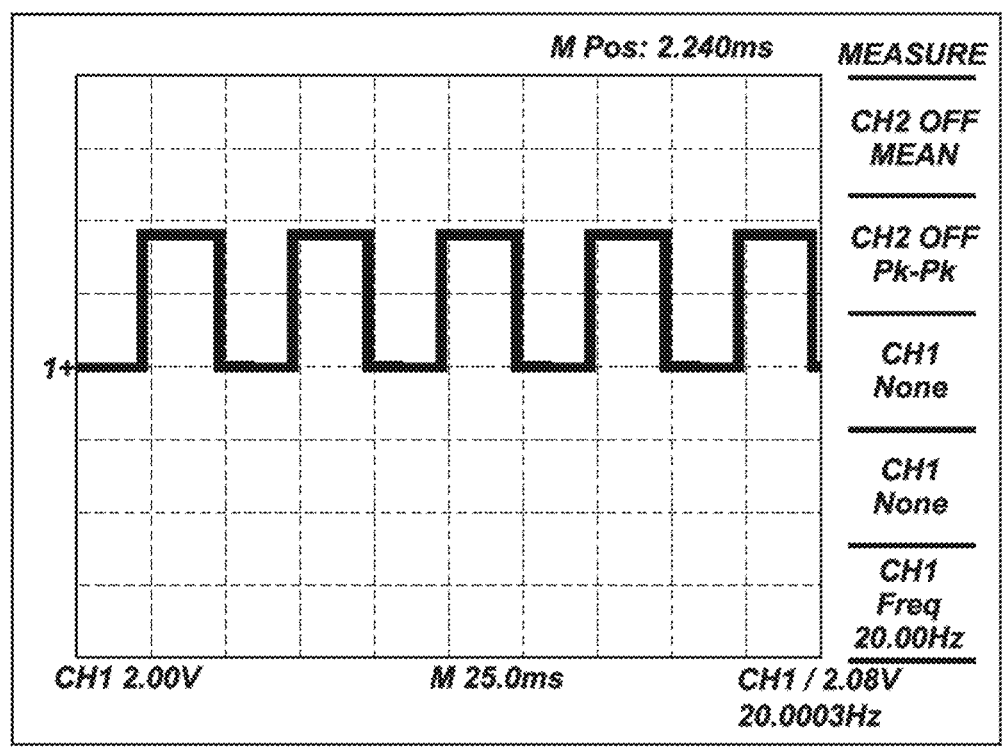
FIG. 15 depicts an image of the signal (voltage and frequency) associated with proliferation: 2.5-6.0 V (4 V here), 20 Hz, pulse width 200-700 µs, square wave.
Figure 16:
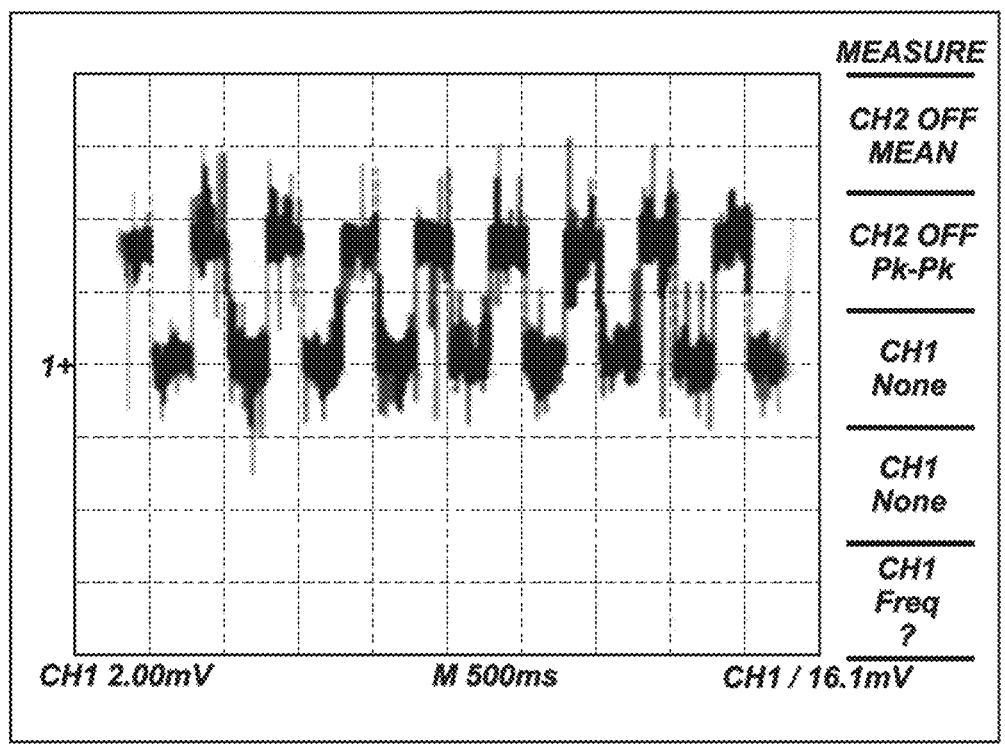
FIG. 16 depicts an image of the signal (voltage and frequency) associated with RANKL: 3.0 mV, 2 Hz, square wave.
Figure 17:
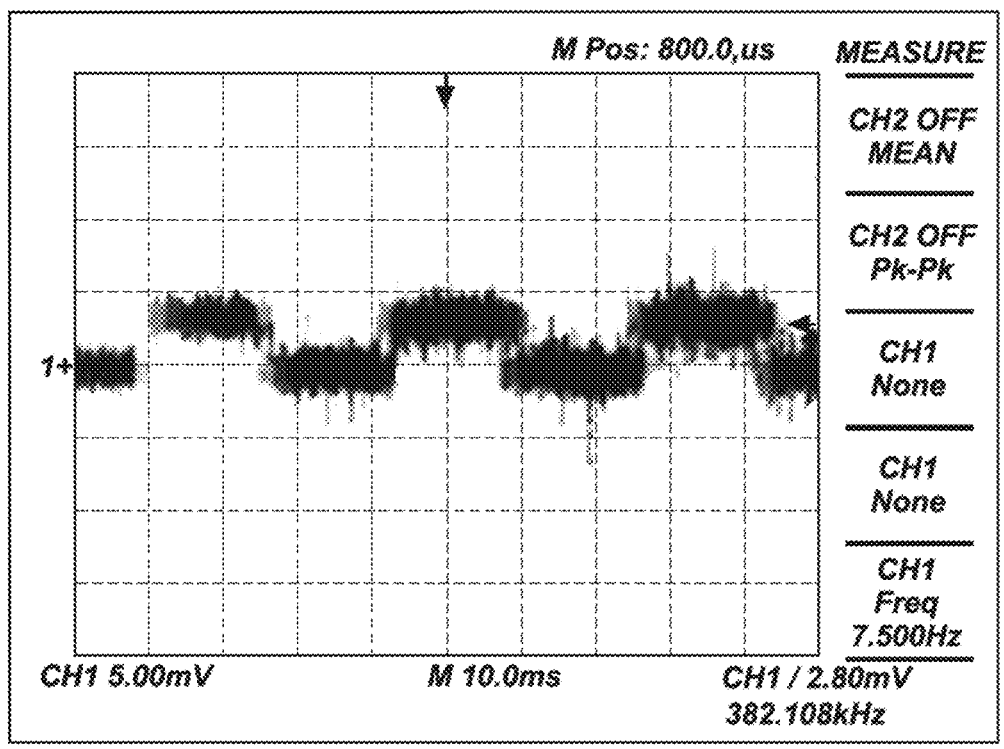
FIG. 17 depicts an image of the signal (voltage and frequency) associated with SDF-1: 3.5 mV, 30 Hz, square wave.
Figure 18:
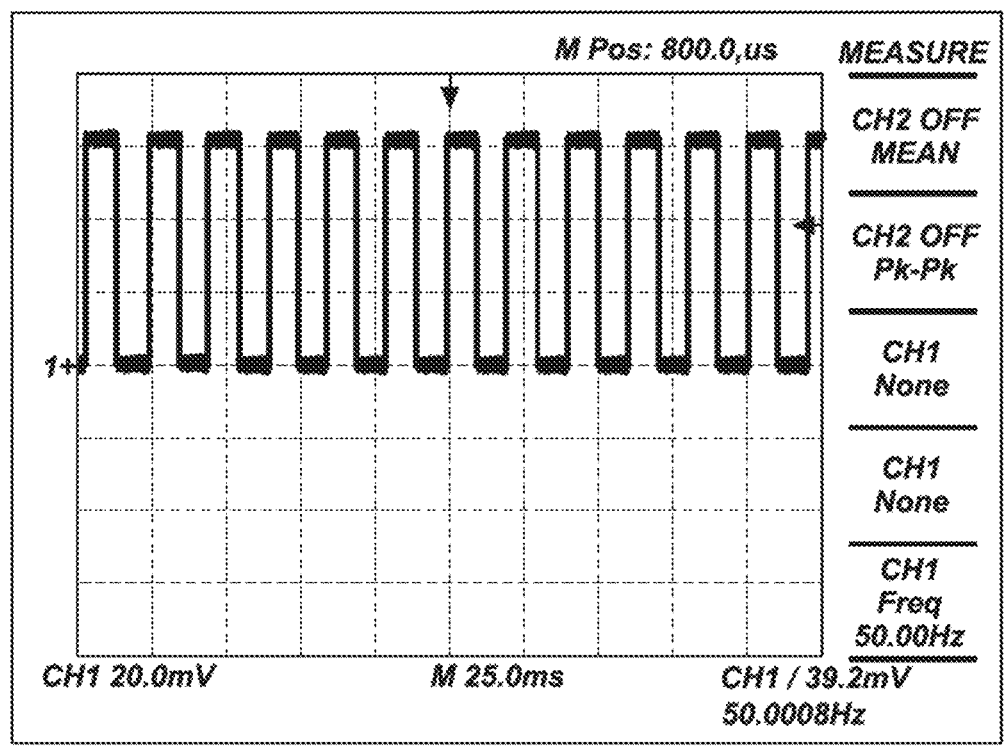
FIG. 18 depicts an image of the signal (voltage and frequency) associated with tropoelastin: 60 mV, 50 Hz, square wave.
Figure 19:
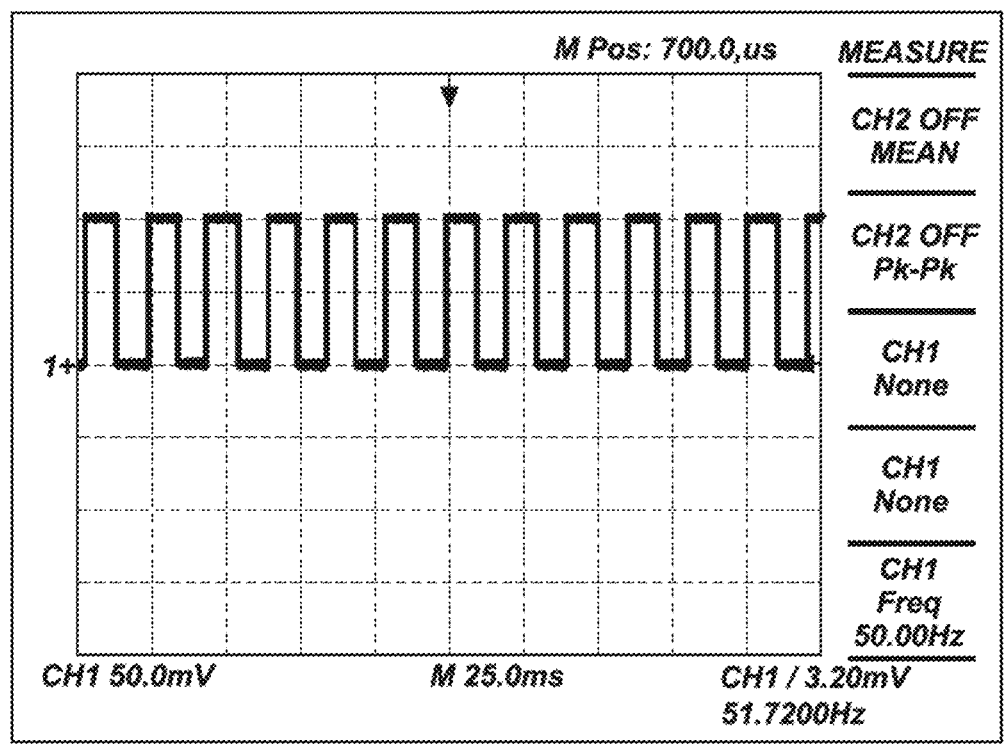
FIG. 19 depicts an image of the signal (voltage and frequency) associated with VEGF: 100 mV, 50 Hz, square wave.
Figure 20:
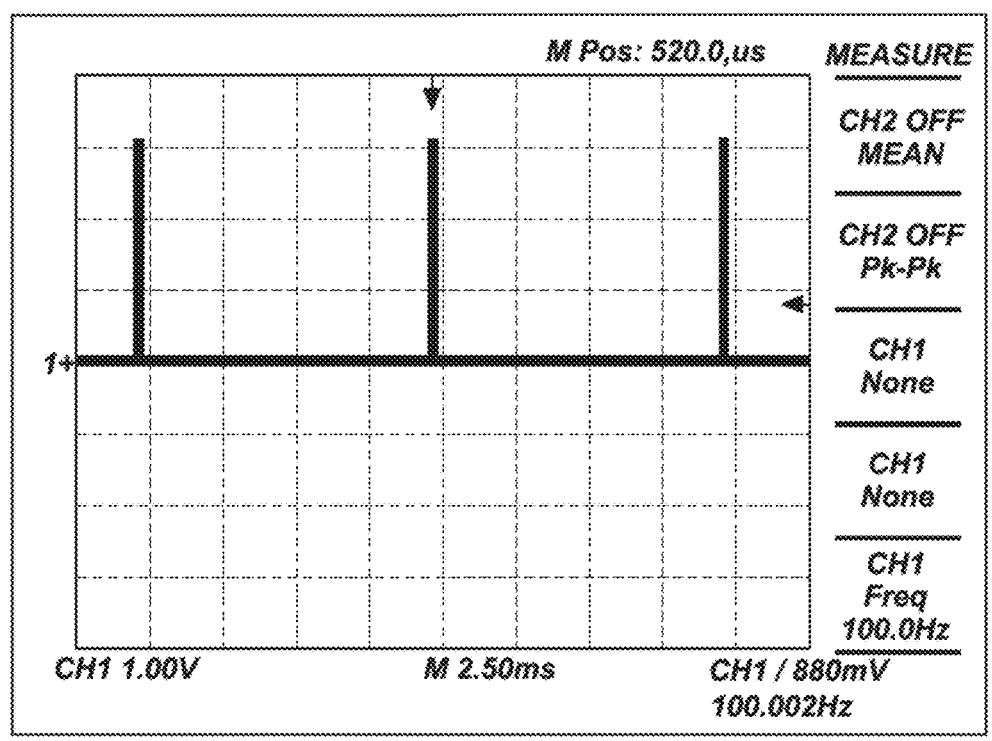
FIG. 20 depicts an image of the signal (voltage and frequency) associated with SDF-1 ($2^{nd}$ part): 0.25 mA (3.0 V shown here), 100 Hz, 100 µs pulse width, square wave.

Specifically, FIG. 6 depicts an image of the signal (voltage and frequency) associated with Activin B at 6.0 mV, pulse width 100 µs, square wave on a TEKTRONIX® TPS 2024 four channel digital storage oscilloscope. FIG. 7 depicts an image of the signal (voltage and frequency) associated with EGF at 10 V/cm (5V here), 500 Hz, pulse width 180 µs, square wave. FIG. 8 depicts an image of the signal (voltage and frequency) associated with follistatin at 10 V/cm, 50 Hz, square wave. FIG. 9 depicts an image of the signal (voltage and frequency) associated with HGF at 3.5 V, 10 second burst every 30 seconds, square wave. FIG. 10 depicts an image of the signal (voltage and frequency) associated with IGF-1: 3.0 mV, 22 Hz, square wave. FIG. 11 depicts an image of the signal (voltage and frequency) associated with OPG: 4.0 mV, 2,000 Hz, square wave. FIG. 12 depicts an image of the signal (voltage and frequency) associated with PDGF 30%: 3 V/cm (100 mV here), 10 Hz, pulse width 200 µs, square wave. FIG. 13 depicts an image of the signal (voltage and frequency) associated with PDGF 230%: 20 V/cm (7.0 V here), 100 Hz, pulse width 100 µs, square wave. FIG. 14 depicts an image of the signal (voltage and frequency) associated with proliferation: 15 mV, 70 Hz, square wave. FIG. 15 depicts an image of the signal (voltage and frequency) associated with proliferation: 2.5-6.0 V (4 V here), 20 Hz, pulse width 200-700 µs, square wave. FIG. 16 depicts an image of the signal (voltage and frequency) associated with RANKL: 3.0 mV, 2 Hz, square wave. FIG. 17 depicts an image of the signal (voltage and frequency) associated with SDF-1: 3.5 mV, 30 Hz, square wave. FIG. 18 depicts an image of the signal (voltage and frequency) associated with tropoelastin: 60 mV, 50 Hz, square wave. FIG. 19 depicts an image of the signal (voltage and frequency) associated with VEGF: 100 mV, 50 Hz, square wave. FIG. 20 depicts an image of the signal (voltage and frequency) associated with SDF-1 ($2^{nd}$ part): 0.25 mA (3.0 V shown here), 100 Hz, 100 µs pulse width, square wave.

Production of SDF-1 is best under control with two signals in sequence. If ones uses just one signal, the SDF-1 increased expression effect peaks at one (1) hour and then diminishes. If you use two signals, the SDF-1 expression effect does not diminish after one (1) hour.

In certain embodiments, a subject's organ(s) and/or tissue(s) are first scanned or analyzed with a device to determine what his or her needs may be before treatment begins. The scanning/analysis can be by, e.g., generating mechanical vibrations at position adjacent the location to be an analyzed as described in, e.g., U.S. 2003/0220556 A1 to Porat et al. (the contents of which are incorporated herein by this reference) and/or by measuring transmembrane voltage potential of a cell (see, e.g., Chernet and Levin, "Transmembrane voltage potential is an essential cellular parameter for the detection and control of tumor development in a Xenopus model," *Dis. Models and Mech.* 6, pp. 595-607 (2013); doi:10.1242/dmm.010835, the contents of which are also incorporated herein by this reference. See, also, Brooks et al. "Bioelectric impedance predicts total body water, blood pressure, and heart rate during hemodialysis in children and adolescents," *J. Ren. Nutr.,* 18(3):304-311 (May 2008); doi: 10.1053/j.jrn.2007.11.008, the contents of which are incorporated herein by this reference, describing the use of bioelectric impedance to evaluate the variability of blood pressure, systolic blood pressure, etc.

As used herein, "scanning" means measuring bioelectrical electrical activity of organs, sometimes by placement of a bion coil reader and transmitter in the organ, and direct that information to a computer. The computer stores the bioelectrical read measurements of diseased organs and healthy organs and makes a comparative exam classifying the organ into one category or another, which is much like a doctor using information to make a diagnosis.

Presently, the best approach for whole body and individual organ scanning is to use a combination of: (a) 3D Body Scannint, (b) Quantum Magnetic Resonance Scanning, (c) Biofeedback scanning, (d) Bioelectric scanning, (e) Bion implant scanning, (f) Nervous system scanning, and (g) Light-activated cell reaction reading.

Scanners such as the Ina' Chi scanner, the Quantum Magnetic Resonance Analyzer (QMRA), the 3D Quantum Health Analyzer Scan whole body organ health 2, Body-Scan® scanner, and the "BIONic muscle spindle" are also useful.

See, also, P. Collins "Bioelectric Signals Can Be Used to Detect Early Cancer," *Tufts News*, http://now.tufts.edu/news-releases/bioelectric-signals-used-detect-early-cancer (Feb. 1, 2013) reported that scientists had discovered a bioelectric signal that can identify cells likely to develop into tumors, and that they could lower the incidence of cancerous cells by manipulating the electrical charge across cell membranes. After the subject's needs in this regard are determined, then treatment (e.g., enhanced tissue growth or regeneration) may be initiated as needed and/or desired, preferably with the same device.

U.S. Pat. No. 9,032,964 to Schuler, the contents of which are incorporated herein by this reference, entitled "Method and system for processing cancer cell electrical signals for medical therapy" describes a scientific computer system with processor capable of recording, storing, and reprogramming the natural electrical signals of cancer cells as found in tumors of humans and animals. The reprogramming process is designed to create a confounding electrical signal for retransmission into a malignant tumor to damage or shutdown the cellular internal electrical communication system. Altering the electrical charge on the glycocalyx of the outer cell membrane is also part of the treatment by application of ions. The system causes cancer cell death as a medical treatment using ultra-low voltage and amperage encoded signals which are reprogrammed from cancer cell communication signals.

For example, the subject is positioned for analysis with a device, preferably with a non-invasive testing device for evaluating, e.g., the autonomic nervous system, organ function(s), and risk factors associated with heart disease, diabetes, and stroke. The non-invasive testing device may analyze data from, e.g., the subject's skin galvanic response, skin color, oximeter, blood pressure, and body composition analyzer to determine hardening and thickening of the subject's arteries, the subject's heart health, exercise capacity, thyroid function, neurotransmitter balance, and multiple other markers for health. See, also, Fatemi et al. "Imaging elastic properties of biological tissues by low-frequency harmonic vibration" *Proceedings of the IEEE,* 91(10): 1503-1519 (October 2003).

In an alternative embodiment, the analysis conducted by the device comprises (or further includes) detecting minute energy fields around the human body with, e.g., a "SQUID magnetometer" (SQUID is an acronym for "Superconducting Quantum Interference Device"), able to detect biomagnetic fields associated with physiological activities in the subject's body. A quantum resonant magnetic analyzer analyzes such fields. The magnetic frequency and energy of a subject's organ(s) and/or tissue(s) are collected by appropriately positioning the sensor with respect to the portion of the subject's organ(s) and/or tissue(s) to be analyzed, and after amplification of the signal by the instrument, the data are compared with standard quantum resonant spectrum of diseases, nutrition, and other indicators/markers to determine whether the sample waveforms are irregular using a Fourier approach.

Treatment may include, e.g., moving magnets or changing magnetic fields (pulsed electromagnetic fields) about the tissue and/or organ, for example, to reduce inflammation or treat pain or induce tissue growth in the subject.

The subject's body is scanned to detect non-cancerous tissue damage. When non-cancer damage is detected, treatment may be initiated/indicated/scheduled.

The invention is further described with the aid of the following illustrative Examples.

EXAMPLES

Example

Controlling Expression of Follistatin

Low voltage pulsed electrical stimulation device for controlling expression of follistatin, a muscle formation promotion protein, from tissues.

Epicardial stimulation is especially useful for heart regeneration.

In one embodiment, the system stimulates the controlled production/release of follistatin, a known myostatin inhibitor, thus promoting the formation of new muscle and repair of damaged or weakened muscle including heart muscle post heart attack. Follistatin-like 1 (FSTL1) is a protein that encourages the growth of healthy cells, contractile muscle tissue and even blood vessels, helping supply the newly created muscle tissue with oxygen and nutrients. This therapy was originally designed to reduce or eliminate scarring of the heart following a heart attack and reversing heart failure, but may also be applicable to treating other organs suffering from muscle loss or degradation.

The electrical stimulation device promotes the reliable controlled expression and/or release of follistatin with practical, safe, low voltages. The version of the system described in this Example includes the following components: Micro voltage signal generator (micro-stimulator from QIG Greatbatch); pacing and infusion lead; corkscrew tip; conductive polymer bandage wrap or patch; signal programmer; and external battery charging wand.

Relationship Between The Components:

The micro voltage signal generator is attached to the pacing infusion lead with, e.g., a corkscrew tip or conductive polymer bandage or patch to the tissue or organ to be treated. An external signal programmer may be used to program the micro voltage signal generator with the proper signals for treatment including the follistatin producing signal. The device battery may be re-chargeable with an external battery charging wand.

In use, the signal generator sends a signal to the target tissue organ that causes the genes within the DNA of that tissue to start the follistatin synthesis process on demand. The signal generator sends a signal to the target tissue organ that causes the genes within the DNA of that tissue to start releasing follistatin on demand. The follistatin—(muscle growth) production signal is preferably 10 V at 50 HZ and 100 HZ 0.25 mA alternating back and forth. A 3 V signal is being developed.

The system not only controls the DNA to build ribosomes and proteins, but also controls the gates of the cell membranes opening and closing correctly to promote regeneration.

The essential elements are the micro voltage signal generator and the means for delivering the signal to the target tissue.

A micro infusion pump is included to the system for delivering other supportive substances or even follistatin in greater volume more quickly.

The signal generator may be external or internal. The transmission of the signal may be wireless, via liquid and/or via wires.

The tissue contact interface may be a patch or bandage or may be via electrodes or leads.

The described system produces follistatin under precise dosing control at safe and comfortable low voltages.

The signal generator programmed with the follistatin expression and/or release signal is directed via a lead, bandage of patch to the target organ tissue in need of muscle repair or build up. As the signal is in stimulation mode the tissue releases follistatin and muscle is built or repaired as needed until full function resumes or the desired enhanced function is reached.

Example

Treatment of the Pancreas with Bioelectric Controlled Protein

Treatment of the pancreas with bioelectric controlled protein expression and micro infusion pump stem cell composition delivery A pancreas regeneration system includes three primary components. First, the micro bioelectric regeneration stimulator (micro-stimulator from QIG Greatbatch) that controls expression and/or release of 10 regeneration promoting proteins including SDF-1 a stem cell homing signal, IGF-1, HGF, EGF, activin A and B, eNOS, VEGF, follistatin and tropoelastin. Second, a programmable, re-fillable micro infusion pump. Third, a fifteen component stem cell-based regeneration composition comprising a variety of cell types, growth factors, BMP-7, PDLI-1, HGH, selected alkaloids, micro RNAs, nutrient hydrogel, NADA and pancreatic matrix.

In use, the stimulator and pump are implanted just below the subject's skin with a re-fillable silicone septum port with pacing infusion lead directed to the pancreas with a total conductive infusion wrap tip that is gentle on the pancreatic tissue. One portion of the pacing infusion lead is directed to the interior portion of the pancreas.

Example

Brain and Organ Regeneration Device Based on Bioelectric IGF-1 Stimulation

An organ regeneration device that produces controlled expression and/or release of platelet-derived growth factor by bioelectric stimulation is disclosed. The system provides controlled sustained and repeated expression and/or release of PDGF via a wire conduction lead or wireless signal delivery and may be combined with a micro infusion pump for maximum results in severe organ failure cases.

A Brain and Organ Regeneration Device based on Bioelectric IGF-1 Stimulation is disclosed. The system directs a lead to exactly the right position with the target organ and stimulates controlled expression of IGF-1 in combination with SDF-1, VEGF, HGH, HGF, Follistatin and tropoelastin in the proper sequence to optimize repair and regeneration.

Damaged aged or cancer stricken organs and tissues are unable to be regenerated back to their original health with prior art therapies. Further, injections wash away and needle pricks are painful and the entry site is too far away from the organ. Other prior art electrical stimulation devices do not: produce the expression IGF-1 or other combination useful proteins in the most effective sequence.

The disclosed system directs a lead to exactly the right position with the target organ and stimulates controlled expression of IGF-1 in combination with SDF-1, VEGF, HGH, HGF, follistatin, and tropoelastin in the proper sequence to optimize repair and regeneration.

IGF-1 can transport raw materials to the cells for repair and renovation. IGF-1 promotes raw material transport to the cells. Meanwhile, nucleic acids are helpful in repairing the damage in the DNA, while stimulating cell division. IGF-1 is able to minimize the DNA and cell stellar damage, but also treat the DNA and the cell. The IGF repair cells and thus tissues and organs, especially when delivered over time in combination with other factors such as SDF-1, VEGF, HGH, HGF, follistatin, and tropoelastin.

Controlled on demand expression of IGF-1 can help repair cells, tissues and organs including brain, muscle, pancreas, lung, skin, kidney and liver.

IGF-1 injections and infusions do not get enough repair material to the target organ or tissue and cause inflammation, which is counterproductive to regeneration. Thus electrical stimulation is preferred. Prior art electrical stimulation systems failed to express the right regenerative proteins at the right time.

The system directs a lead to exactly the right position with the target organ and stimulates controlled expression of IGF-1 in combination with SDF-1, VEGF, HGH, HGF, Follistatin, and tropoelastin in the proper sequence to optimize repair and regeneration. Also, it can produce hearts, kidneys, livers, lungs, brains, pancreas, lung, skin, knees, and elbows, skin, penis, breasts, aorta, arteries, and limbs.

The version of the system discussed for this Example includes the following components: bioelectric regeneration stimulator (micro-stimulator from QIG Greatbatch); signal for causing controlled expression and/or release of IGF-1: applied 20V at one (1) Hz with a frequency of 5 ms for 24 hours; signal for causing controlled expression and/or release of SDF-1; signal for causing controlled expression and/or release of VEGF; signal for causing controlled expression and/or release of HGH; signal for controlled expression and/or release of HGF; signal for controlled expression and/or release of follistatin; signal for controlled expression and/or release of tropoelastin; pacing infusion lead to implant in organ or tissue to be treated; infusion and electrode wide area patch (optional); wireless transmitter for all signals listed above (optional); refillable micro pump (optional); external programmer; and external battery charger.

The regeneration stimulator may be implanted just below the skin of the patient or may be external, especially if the wireless option is chosen. For the implantable model, an infusion conduction lead is directed from the stimulator to the organ or tissue to be repaired. The tip of the lead is lodged into the tissue with a corkscrew or other fixation tip. The regeneration stimulator is programmed by an external programmer. The stimulator is programmed to cause expression and/or release of specific regeneration proteins in a preferred sequence to optimize organ repair starting with VEGF, then SDF-1, then IGF-1, then HGH, then HGF, then follistatin, then tropoelastin. The wireless version is applied externally with the signal pointed to the organ to be regenerated. The signal may be constantly calibrated to adjust for fat, skin, and other obstacles between the signal generator and the organ of Interest to be treated. The device may be recharged with an external charger. In cases of very widespread organ damage, a wide array infusion and electrode patch may be used to cover the damaged organ area more completely. To accelerate the organ regeneration, an implantable, programmable, refillable micro infusion pump may be used to deliver various stem cells, nutrient hydrogels Micro RNA's and growth factors and (in some cases) drugs.

SDF-1 recruits via homing signal new reparative stem cells to the damaged organ, VEGF causes new nutrient and oxygen producing blood vessels to grow into the area being treated. IGF-1 repairs damaged cells, tissues and organs. Follistatin repairs damaged muscle. Tropoelastin adds elasticity to treated tissues making them more compliant. HGF aides in all repair processes and in the specific case of heart regeneration, reduces the risk of arrhythmias. All of these proteins work together to fully regenerate an organ over time. The process am be accelerated with the use of a micro infusion pump that is filled with various types of stem cells and growth factors and in some cases drugs.

The construction of electric signal generators, and pacemakers, are known to the art and can be obtained from OEM suppliers as well as their accompanying chargers and programmers. What is unique is the programming of specific signals to use specific protein expressions at precisely the right time for optimal organ regeneration. Pacing infusion leads may be purchased from a variety of OEM vendors. An infusion and electrode wide area pitch may be constructed by cutting conduction polymer to shape and forming plastic into a flat bag with outlet ports in strategic locations.

Any one of the protein expression signals work well on their own for organ regeneration, but they work better together. As previously identified herein, SDF-1 is the most powerful regeneration protein followed by IGF-1.

A wireless, single lumen infusion pacing lead or infusion conduction wide array patch may all be used to deliver the regeneration signals and substances to the organ of interest to be treated or they may be used in combination.

A bionic neuron ("BION") device (injectable microstimulator) may be adapted to provide the requisite stimulation. Such a device is typically the size of a long grain of rice (2 mm wide by 15 mm long) and comprises an integrated circuit chip sandwiched inside an antenna coil.

The regeneration stimulator lead or wireless signal is directed to the organ to be regenerated and the protein signals are delivered. Again, the most important is SDF-1 which recruits new stem cells to the site and its accompanying reverse polarity signal which triggers differentiation of the recruited stem cells into useful tissues.

The second most important is IGF-1, which is highly potent in cell repair. VE'GF helps grow in blood vessels for feeding the newly created and newly regenerated tissues.

Example

PDGF

Described herein is the bioelectric controlled expression of platelet derived growth factor (PDGF). PDGF is a powerful organ regeneration protein/cytokine. PDGF is one of the most potent growth factors in promoting cell, tissue and organ repair applicable to a wide variety of uses. It has been demonstrated to be especially useful in heart regeneration.

Described is the precise bioelectric signal for triggering PDGF expression from tissues. PDGF combined with the programmable micro-infusion pump and fifteen component organ regeneration composition is to help patients with degenerating and diseased organs to recover. Both wireless non-invasive and implantable wire lead based means may be utilized to get the regeneration and healing promoting bioelectric signals to organs.

PDGF constitute a family of four gene products (PDGF-A-D) acting by means of two receptor tyrosine kinases, PDGFRα and β. Three of the ligands (PDGF-A, PDGF-B, and PDGF-C) bind to PDGFRα with high affinity. PDGF signaling is essential for epicardial cell proliferation. PDGF signaling plays important roles in coronary vessel formation.

PDGF also induces DNA synthesis in cardiomyocytes. PDGF recruits stem/progenitor cells. PDGF can trigger controlled cell proliferation. PDGF can contribute to cell reprogramming and transformation into induced multipotent stem cells. PDGF downstream effects include regulation of gene expression and the cell cycle. PDGF can be used to create cell-specific antifibrotic compounds including those needed for liver regeneration. PDGFs are required for normal kidney development via recruitment of mesenchymal cells to both glomeruli and the interstitium. PDGF exerts essential roles from the gastrulation period to adult neuronal maintenance by contributing to the regulation of development of preplacodal progenitors, placodal ectoderm, and neural crest cells to adult neural progenitors, in coordinating with other factors. PDGF plays critical roles for maintenance of many specific cell types in the nervous system together with vascular cells through controlling the blood brain barrier homeostasis. PDGF modulates neuronal excitability through adjusting various ion channels, and affecting synaptic plasticity and function. PDGF stimulates survival signals, majorly PI3-K/Akt pathway but also other ways, rescuing cells from apoptosis. PDGF in dendrite spine morphology is critical for memory in the developing brain. PDGF has been found to stimulate regeneration of periodontal tissues and bone. PDGF signaling is essential in regeneration of hearts in animals. PDGF signaling induces DNA synthesis in the cells and is required for cardiomyocyte proliferation during heart regeneration. PDGF was used in biological pacemaker development, and it worked well to help form new sino atrial node cells from atrial myocytes. PDGF has been found useful in regeneration of other organs such as eyes, lungs, kidneys, brains, and aortas.

Described is an organ regeneration device that produces controlled expression and/or release of PDGF by bioelectric stimulation. Failing organs cannot produce enough PDGF to fully regenerate.

Other devices only provide one time delivery of PDGF, which is insufficient to fully regenerate a failing organ. Infusion systems lose too much therapeutic agent.

The system provided herein provides controlled sustained and repeated delivery of PDGF via a wire conduction lead or wireless signal delivery and may be combined with a micro infusion pump for maximum results in severe organ failure cases.

The bioelectric stimulator preferably reads the needs of an organ and produces expression and/or release of PDGF in just needed amounts to enhance organ regeneration. Researchers previously conducted organ regeneration studies of one time injection of PDGF with a needle and syringe. This is impractical and will not work for major organ repair.

A onetime dose is not enough to fully regenerate an organ. To access the organ with a needle and syringe is very invasive, dangerous and painful. Injected or infused PDGF has a high wash out loss rate.

The system provides controlled sustained and repeated expression and/or release of PDGF via, e.g., a wire conduction lead or wireless signal delivery and may be combined with a micro infusion pump for maximum results in severe organ failure cases.

Also, it can produce the device may also be used for organ enhancement instead of just organ repair such as brain function enhancement.

The version of the system discussed for this Example includes the following components: micro bioelectric signal generator; programming wand; programming computer; pacing infusion lead; micro infusion pump; PDGF bioelectric signal program; PDGF solution; organ reading device and processor; organ reading software program and analysis software; and wireless energy beam transmitter.

Relationship Between The Components:

The micro bioelectric stimulator is programmed with the programming wand connected to the programming computer with the PDGF bioelectric signal of 20 V, 50 Hz, and 0.2 amps. The micro stimulator is connected to the pacing infusion lead and the other side of that lead is affixed in the central portion of the damaged or diseased target organ. The programming wand connected to the programming computer can active the micro bioelectric stimulator to become an organ reading device. When programmed with the organ reading and analysis software the organ reader is able to read all the bioelectric activity of the failing organ as well as its phenotype, genotype including genetic defects and variation and chemical and biologically metabolism.

The bioelectric stimulation controlled PDGF expression causing new blood vessels to grow into the failing organ(s) and new healthy organ tissue to form. The reader adjusts the therapeutic dose as needed. The micro infusion pump refilled daily with a mixed stem cell based composition that includes PDGF and may also include SDF-1, IGF, EGF, HGF, HGH, Activin A and B, eNOS, VEGF, follistatin, tropoelastin. GDF-10, GDF-11 and Neurogenin-3, selected alkaloids, and selected anti-inflammatory factors may be used to supplement the bioelectric stimulation therapy for organ repair in seriously failing organs.

If the organ failure is severe, an added programmable, implantable, re-fillable micro infusion pump may be added to the therapy. The micro pump is refilled daily with about 2 ml of stem cell-based organ regeneration composition that includes PDGF. If it is not easy or desirable to reach the organ to be treated with a wire-based pacing infusion lead, the operator may utilize a wireless energy beam transmitter to deliver the bioelectric regeneration signals wirelessly to the organ.

In this embodiment, the stimulator, lead, and programmer are essential. The micro infusion pump and mixed organ regeneration composition are optional.

The micro stimulator, and if chosen, the micro infusion pump are implanted somewhere below the skin of the patient with the pump silicone septum ports accessible for refilling just below the skin. The stimulator must be in a location reachable by the programming wand attached to a portable computer. The pacing infusion lead form the stimulator and pump is directed to the central damaged portion of the damaged organ, i.e., heart, kidney, pancreas, liver. The micro stimulator may optionally be non-invasive and external and can deliver its signal to the failing organ via a focalized wireless energy beam. Much like how they focalize radiation to treat cancer tumors, but this energy stimulates organ regeneration.

Additionally: The micro stimulator may be programmed for additional protein expressions. The micro pump may be used a stand-alone device. The sequence of use may be changed.

The device may also be used for organ enhancement instead of just organ repair such as brain function enhancement.

Two PDGF expression control signals. One low voltage and one higher voltage. The test tissue is sheep heart tissue, while the test cells are mesenchymal stem cells. 30% PDGF increase with 3 V/cm, 10 Hz, 2 micro amps (0.000002 amps) and the pulse duration 0.2 ms. 230% PDGF increase with 20 V/cm 100 Hz, 0.25 mA ($2.5e^{-7}$ amps) and pulse duration of 40 pulses/s, width of 100 µs.

Example

Treating Cancer Tumors Using Bioelectric Stimulation in Combination with Micro Infusion Previous cancer treatments failed to address the combination of stopping cell proliferation and blood supply followed by regenerating the damaged tissue or organ.

Cytokine and Chemotherapeutic and regenerative treatment for certain cancers may be combined with low intensity, intermediate frequency alternating electric fields that are tuned to expression and/or release specific beneficial proteins at specific time intervals. More specifically, cell proliferation inhibition and halting blood supply to tumors in the first treatment stage. The bioelectric stimulation treatment may be increased in volume and efficacy by the combination use of an implantable, programmable, re-fillable micro infusion pump that delivers anti-cell proliferation and anti-blood vessel growth proteins as well, if desired, standard cancer treatment drugs such as chemo therapy agents. The second stage of treatment is focused regeneration of cancer damaged tissues back to their most optimal healthy state. The regenerative phase comprises a sequence of recruiting reparative stem cells to the damaged organ by bioelectrically stimulating the expression and/or release of SDF-1 (stem cell homing factor), followed by a controlled proliferation signal, a controlled blood vessel supply signal (VEGF) and if desired and useful expression and/or release of Follistatin, tropoelastin, HGF, IGF-1 and Activin. The stimulation cycle causing expression and/or release of beneficial proteins for regeneration may be upgraded in volume and speed of delivery by the combination use of an implantable, re-fillable, programmable micro infusion pump for delivering a higher quantity of stem cells, nutrient hydrogel, matrix and beneficial tissue and organ regeneration promotion proteins.

Cytokine and Chemotherapeutic and regenerative treatment for certain cancers comprising a combination low intensity, intermediate frequency alternating electric fields that are tuned to expression and/or release particular beneficial proteins in two stages, stage (1) is stopping cancer spread by halting cell proliferation and halting tumor blood supply and stage (2) regenerating the cancer damaged tissue or organ back to optimal health. In many cases, the resulting cell proliferation inhibition is significantly higher than the inhibition obtained by drug-only regimens of treatment.

A method of killing or inhibiting the growth of cancer cells in a target region followed by regenerating the tissue or organ back to optimal health, the method comprising the steps of:

Stage 1=Stop cancer growth by:

Applying, to the target region, a series of bioelectric signals that damages the cancer cells or inhibits the growth of the cancer cells via stopping cell proliferation and halting blood supply temporarily, but leaves normal cells in the target region substantially unharmed; and Treating the cancer cells with another anti-cancer regimen via programmable micro pump infusion, wherein the applying step and the treating step are performed simultaneously.

Stage 2=Regeneration of post cancer tissue or organ by:

Treating the target region with a series of bioelectric signals to recruit stem cells, grow healthy blood vessels and re-grow healthy functional tissues in the previous cancer damaged region In such a method, in the applying step, the field may be applied in at least two different directions in an alternating sequence to halt cell proliferation and to stop blood supply to the tumor.

In such a method, the other anti-cancer regimen may comprise treating the cancer cells with an anti-cancer drug. In this method, the drug may comprise at least one drug selected from the group consisting of paclitaxel, doxorubicin cyclophosphamide, and cisplatin. In such a case, the drug dosage may be less than 20% of a standard dosage for the drug.

In such a method, the bioelectric stimulation may expression and/or release any one of these regeneration of tissue and organ beneficial proteins SDF-1, IGF-1, Activin, HGF, VEGF, Follistatin or tropoelastin and in specific sequences for optimal organ health.

In such a method, all bioelectric regeneration signal may be delivered wirelessly and/or non-invasively.

In such a method, the target cancer may be breast cancer and the target regenerative organ may be breast reconstruction.

In such a method, the target cancer may be brain cancer and the target regenerative organ is brain.

In such a method, the target cancer may be prostate cancer and the target regenerative organ may be the prostate.

In such a method, the target cancer may be colon cancer and the target regenerative organ may be the colon.

In such a method, the target cancer may be throat or esophageal cancer and the target regenerative organ may be throat or esophagus.

In such a method, the target cancer may be pancreas cancer and the target regenerative organ may be the pancreas with improved insulin production.

In such a method, the target cancer may be lung cancer and the target regenerative organ may be lung(s).

In such a method, the target cancer may be eye cancer and the target regenerative organ may be the eye.

Example

A combination protein expression stimulator, micro infusion pump, and fifteen (15) component stem cell-based composition for saving brain function in a subject following stroke or injury.

Brain function is lost when a stroke or brain injury occurs in a subject due to lack of oxygen and nutrients reaching a particular portion of the brain. Prior art therapies are typically drugs that do nothing to regenerate lost brain tissue. Chemical drugs do not do anything to affect neurogenesis (the growth of new brain tissue to replace damaged brain tissue). For example, the most popular simply dissolves blood clots, stopping further damage, but doing nothing to recover brain tissue already lost.

Prior art electrical stimulation devices do not have the correct signals for homing stem cells or for regenerating brain tissue. Existing electrical stimulation devices deliver one signal and that signal does not promote regeneration of lost brain tissue. Burst electrical pulses of old-type stimulators do nothing to affect neurogenesis.

Prior art one-time stem cell injections of one type of stem cell or modified stem cell have achieved some success, but this therapy is limited and incomplete. One-time needle injection cell therapies are too limited to recover major lost brain function. One-time injection of stem cells on a stand-alone basis mostly die out without a support system and cannot affect major neurogenesis.

The herein described combination of bioelectric stimulation of ten (10) key regeneration proteins via bioelectric signals, 24 hours a day for seven days a week, combined with daily or weekly infusions of the herein described fifteen component compositions provides much more complete repair, recovery, and regeneration of lost brain function.

The herein described device, method, and system practice all forms of "good farming" to grow a "new crop" of functional brain tissue in the skulls of post-stroke and post-injury subjects.

The herein described system rapidly and easily delivers ten (10) brain regeneration promoting bioelectric signals to the subject within minutes, combined with a micro infusion pump that delivers fifteen (15) component angiogenic and regeneration compositions rapidly and safely. This, in combination, can fully restore brain functionality back to normal.

The ten (10) key regeneration proteins are SDF-1 (stem cell homing signal), IGF-(1 DNA repair and brain regeneration signal), HGF, EGF, Activin A and B, eNOS, VEGF, follistatin, and tropoelastin signal as described herein.

The system discussed in this Example preferably includes: the bioelectric signal generator, a programmable, re-fillable micro infusion pump, a brain saving helmet with electroacupuncture needles built in, micro infusion leads stereotaxic directed to deep brain regions, a fifteen component angiogenic composition, a fifteen component regeneration composition, human placenta, fetal serum, a cell proliferation signal, and a cell controlled differentiation signal.

In use, the bioelectric signal generator and the micro infusion pump are both attached to the brain saving helmet with electroacupuncture needles (not shown). The helmet is placed on the head of the patient. If the brain saving helmet with electroacupuncture needles is not used, one may use "off the shelf" standard, readily available electro-acupuncture needles. The bioelectric signal generator stimulator is activated and the micro infusion pump is filled with first the fifteen component angiogenic composition to increase blood flow and then the next day with the fifteen component regeneration composition.

The bioelectric stimulator cycles through the SDF-1 signal for stem cell homing, then IGF-1 for DNA repair, then HGF, EGF, Activin A and B, eNOS, VEGF, follistatin, tropoelastin, cell proliferation, and cell differentiation. The micro infusion pump may be re-loaded with fetal serum and placenta in severe cases to enhance results. Anti-inflammatory agents may also be used. The bioelectric signal generator stimulator recruits stem cells, causes expression and/or release of regeneration support factors, and multiples cells, and then controls their differentiation into healthy full functioning brain tissue.

The micro infusion pump is filled daily or week with the fifteen component angiogenic and regeneration compositions designed to facilitate neurogenesis. The fifteen component angiogenic and regenerative compositions provide much more complete repair, recovery, and regeneration of lost brain function.

If electrical stimulation alone does not work, the micro pump is filled with angiogenic and regeneration compositions for daily delivery. If those compositions do not work, then fetal serum and placenta may be added.

A bioelectric signal generator can be as described otherwise herein. For some signals, a drop down resistor in the pacing infusion lead may be necessary to drop the lowest voltage and current from the standard pacemakers down to a natural micro voltage level (the same level of natural electricity in a human body). A micro infusion pump can be as described otherwise herein and may be sourced from various drug delivery pump manufacturers and adapted by taking any filters out. The compositions for angiogenic and regeneration purposes are comprised of mixing together components that can be obtained from a person's own body as described herein further processed in a standard cell culturing laboratory (many contract manufacturers are available) or from reliable known suppliers.

The bioelectric signal generator is essential. All other components may be optional. The micro infusion pump, compositions, fetal serum, placenta, and anti-inflammatory agents are only necessary if the bioelectric stimulation on its own has not restored complete function or (e.g., in emergency recovery cases) where time is of the essence such as in an acute stroke situation.

One could use the compositions on their own injected by needle syringe. One could use the micro infusion pump on its own filled with other mixes of stem cells or drugs. One could use the bioelectric stimulator on its own running only one or a few signal programs instead of all of them, or one could program the bioelectric stimulator for entirely different signaling.

Upon arrival to the location of an acute stroke patient, a rapid assessment is made including video phone examination of the patient. A clot dissolving drug is first administered. Then, the brain-saving helmet (e.g., FIG. 23) is placed on the patient's head, and the bioelectric signal generator is turned on running though all ten (10) regeneration signals and the micro infusion pump is loaded first with an angiogenic composition followed immediately thereafter with a regeneration composition. If normal brain function is not restored in the subject with the above steps, the micro infusion pump may be re-filled with fetal serum, placenta, and anti-inflammatory agents, which are then administered.

EXAMPLE

In bioelectric stimulation tissue studies, a 2000% and increase in IL-6 was achieved.

IL-6 is a key promoter of regeneration. With respect to IL-6, Mosteiro et al. (2016) shows that tissue damage is a relevant factor for cells to go back to an embryonic state. Nobel Prize winner Shinya Yamanaka opened the door to regenerative medicine by cell reprogramming, based on introducing a combination of four genes known as OSKM (for genes, OCT4, SOX2, KLF4, and MYC), which reverts adult cells to an embryonic-like state, and transforms these cells into pluripotent cells. Cell reprogramming was later achieved within a living organism (i.e., a mouse) in 2013.

Mosteiro et al. (2016) analyzes what happens in living tissues when reprogramming is induced using OSKM. OSKM was found to be inefficient at inducing reprogramming or pluripotency in the highly specialized cells that constitute adult tissues. Tissue damage plays a critical role by complementing the activity of the OSKM genes.

This relationship between damage and reprogramming is mediated by the proinflammatory molecule, interleukin-6 (IL-6). Without IL-6 being present, the OSKM genes are far less efficient at inducing the reprogramming process. These findings suggest the following sequence of events: the expression of the OSKM genes results in damage to the cells; accordingly, they secrete IL-6; the presence of this molecule induces the reprogramming of some neighboring cells.

Both wireless non-invasive and/or implantable wire lead ("electrode") based means may be used to deliver the regeneration and healing promoting bioelectric signals to target organs.

The controlled expression of Hypoxia Inducible Factor 1 ("HIF-1α") for, e.g., promoting organ regeneration (particularly liver regeneration) is also described herein. HIF-1α is a powerful organ regeneration protein. A more than 286% increase of HIF-1α on demand in test article tissues was achieved with a specific, optimized bioelectric signal. In other experiments, a 2300% increase in expression of HIF-1α was achieved.

Hypoxia has been proven as a critical element in the organ regeneration process. HIF-1α is a master regulator of the adaptive response to hypoxia. HIF-1α over expression in cells mimics the mechanisms triggered by hypoxia in injured or diseased tissues and increases their therapeutic potential without direct hypoxia stimulation.

Potential useful properties of HIF-1α for organ regeneration include: HIF-1α signaling promotes heart regeneration, HIF-1α signaling reduces infarction size and attenuates cardiac dysfunction, HIF-1α induces coronary collateral vessel formation, HIF-1α is a tumor suppressor, HIF-1α has been reported a gateway controller of cancer, HIF-1α promotes liver regeneration, HIF-1α promotes lung regeneration via alveolar development, HIF-1α promotes brain saving following traumatic brain injury or stroke, HIF-1α promotes retinal eye regeneration, HIF-1α management seems to be important to healthy kidney function and can protect against kidney injury, HIF-1α helps promote muscle regeneration, HIF-1α helps promote wound healing, HIF-1α promotes extracellular matrix, HIF-1α has a critical role in bone development and healing, HIF-1α may be important to stabilize teeth positions after accelerated tooth movement, and HIF-1α is an essential regulator of inflammation.

REFERENCES (The contents of the entirety of each of which is incorporated herein by this reference.)

Corrigan et al. "Neurogenic inflammation after traumatic brain injury and its potentiation of classical inflammation", *Journal of Neuroinflammation*, 2016, 13:264; doi://doi.org/10.1186/s12974-016-0738-9.

Liesz et al. "Editorial: Mechanisms of neuroinflammation and inflammatory neurodegeneration in acute brain injury" *Front. Cell. Neurosci.*, 2015. doi://doi.org/10.3389/fncel.2015.00300.

Schimmel et al. "Neuroinflammation in traumatic brain injury: A chronic response to an acute injury" *Brain Circ*, 2017, 3(3):135-142.

Xiong et al. "Current understanding of neuroinflammation after traumatic brain injury and cell-based therapeutic opportunities" *Chin J Traumatol*. 2018 June; 21(3): 137-151. doi: 10.1016/j.cjtee.2018.02.003.

Thattaliyath et al. "Modified Skeletal Myoblast Therapy For Cardiac Failure Using AAV SDF1," *Proc. Intl. Soc. Mag. Reson. Med.* 16, page 579 (2008).

Prochazka et al. "Cocktail of Factors from Fat-derived Stem Cells Shows Promise for Critical Limb Ischemia," http://www.sciencenewsline.com/news/2016012204520017.html (Jan. 21, 2016).

Wei et al. "Epicardial FSTL1 reconstitution regenerates the adult mammalian heart," *Nature* 525: 479-485 (24 Sep. 2015).

"Hearts build new muscle with this simple protein patch," jacobsschool.ucsd.edu/news/news_releases/release.sfe?id=1813 (Sep. 16, 2015).

Salcedo et al. "Low current electrical stimulation up-regulates cytokine expression in the anal sphincter," *Int. J. Colorectal Dis.*, 2012 February; 27(2):221-5. doi: 10.1007/s00384-011-1324-3. Epub (October 2011).

Marie Ellis "Cure for baldness? Stem cells bring hope," http://www.medicalnewstoday.com/articles/271898.php.

Robert Ferris "Battle against baldness turns to stem cells," http://www.cnbc.com/2015/01/29/studies-indicate-its-possible-to-use-stem-cells-to-cure-baldness.html (Jan. 29, 2015).

Thattaliyath et al. "Modified Skeletal Myoblast Therapy For Cardiac Failure Using AAV SDF1," *Proc. Intl. Soc. Mag. Reson. Med.* 16, p. 579 (2008).

"Electrical brain stimulation could support stroke recovery," https://www.sciencedaily.com/releases/2016/03/160316151108.htm (Mar. 16, 2016).

"Electric Tumor Treatment Fields," No. 0827 Policy, http://www.aetna.com/cpb/medical/data/800_899/0827.html (Nov. 18, 2016).

D. Grady "Electrical Scalp Device Can Slow Progression of Deadly Brain Tumors," *New York Times*, https://www.nytimes.com/2014/11/16/health/electrical-scal p-device-can-slow-progression-of-deadly-brain-tumors.html?_r=0 (Nov. 15, 2014).

B. Borgobello "FDA approves the treatment of brain tumors with electrical fields," *New Atlas*, http://newatlas.com/treatment-of-brain-tumors-with-electrical-fields/21433/ (Feb. 13, 2012).

Hopkins Medicine "Overview of Pacemakers and Implantable Cardioverter Defibrillators (ICDs)," http://www.hopkinsmedicine.org/healthlibrary/conditions/cardiovascular_diseases/overview_of_pacemakers_and_implantable_cardioverter_defibrillators_icds_85,P00234/.

Medtronic "Cardiac Resynchronization Therapy (CRT) Devices For Heart Failure," http://www.medtronic.com/us-en/patients/treatments-therapies/crt-devices.html.

Columbia "Implant Procedure Concepts-Pacemaker, ICD and CRT Overview," http://www.columbia.edu/itc/hs/medical/hickey/docs/Pacemaker,%20ICD%20and%20CRT%20Overview%20022007.pdf.

"FDA Approves Algovita Spinal Cord Stimulation System from Greatbatch," http://www.odtmag.com/contents/view_breaking-news/2015-12-02/fda-approves-algovita-spinal-cord-stimulation-system-from-greatbatch (Dec. 2, 2015).

Mass Device "Greatbatch wins FDA PMA for Algovita SCS," http://www.massdevice.com/greatbatch-wins-fda-pma-for-algovita-scs/ (Dec. 1, 2015).

P. Banerjee "Electrical muscle stimulation for chronic heart failure: an alternative tool for exercise training?" *Curr. Heart Fail. Rep.*, 7(2):52-8. doi: 10.1007/s11897-010-0013-9 (June 2010).

HN Sabbah "Electrical vagus nerve stimulation for the treatment of chronic heart failure," *Cleve. Clin. J. Med.*, 78 Suppl. 1:S24-9. doi: 10.3949/ccjm.78.s1.04 August 2011).

Bio-Leonhardt "Micro Stimulator," http://www.bioleonhardt.com/micro-stimulator/.

HU Klein "Vagus Nerve Stimulation: A new approach to reduce heart failure," *Cardiology Journal* (2010).

"Israeli innovation uses nerve stimulation to treat heart failure," https://www.issrael21c.org/israeli-innovation-uses-nerve-stimulation-to-treat-heart-failure/ (Feb. 11, 2007).

Sahoo and Losordo "Exosomes and Cardiac Repair After Myocardial Infarction," *Circulation Research*, 114:333-344 (Jan. 16, 2014).

Tamaki et al. "Cardiomyocyte Formation by Skeletal Muscle-Derived Multi-Myogenic Stem Cells after Transplantation into Infarcted Myocardium," *PLoS ONE* 3(3): e1789. doi:10.1371/journal.pone.0001789 (March 2008).

W. Hoffmann "Regeneration of the gastric mucosa and its glands from stem cells," *Curr. Med. Chem*, 15(29):3133-44 (2008).

Cerrada et al. "Hypoxia-Inducible Factor 1 Alpha Contributes to Cardiac Healing in Mesenchymal Stem Cells-Mediated Cardiac Repair," *Stem Cells and Development*, 22(3): 501-511 (2013).

Fatemi et al. "Imaging elastic properties of biological tissues by low-frequency harmonic vibration," *Proceedings of the IEEE*, 91(10):1503-1519 (October 2003) DOI: 10.1109/JPROC.2003.817865.

Guimardes-Camboa and Evans "Redox Paradox: Can Hypoxia Heal Ischemic Hearts?" *Cell*, 39(4):392-394, (21 Nov. 2016) DOI: http://dx.doi.org/10.1016/j.devcel.2016.11.007.

Huang et al. "Myocardial transfection of hypoxia-inducible factor-1α and co-transplantation of mesenchymal stem cells enhance cardiac repair in rats with experimental myocardial infarction," *Stem Cell Research and Therapy* 5:22 (2014) DOI: 10.1186/scrt410.

Kido et al. "Hypoxia-Inducible Factor 1-Alpha Reduces Infarction and Attenuates Progression of Cardiac Dysfunction after Myocardial Infarction in the Mouse," *JACC*, Volume 46, Issue 11, 6 Dec. 2005, Pages 2116-2124. https://doi.org/10.1016/j.j acc.2005.08.045.

Mosteiro et al. "Tissue damage and senescence provide critical signals for cellular reprogramming in vivo." *Science*, 2016; 354 (6315): aaf4445 DOI: 10.1126/science.aaf4445

Tajima et al. "HIF-1α is necessary to support gluconeogenesis during liver regeneration," *Biochem. Biophys. Res. Commun.* 2009 Oct. 2; 387(4):789-94. doi: 10.1016/j.bbrc.2009.07.115. Epub 2009 Jul. 28.

Tamaki et al. "Cardiomyocyte Formation by Skeletal Muscle-Derived Multi-Myogenic Stem Cells after Transplantation into Infarcted Myocardium," *PLoS ONE* 3(3): e1789. doi:10.1371/journal.pone.0001789 (2008).

Paulus, "Cytokines and heart failure," *Heart Fail. Monit.* 2000; 1(2):50-6.

Gullestad et al. "Inflammatory cytokines in heart failure: mediators and markers," *Cardiology*. 2012; 122(1):23-35. doi: 10.1159/000338166. Epub 2012 Jun. 12.

Mann, "Innate Immunity and the Failing Heart: The Cytokine Hypothesis Revisited," *Circ. Res.* 2015 Mar. 27; 116(7): 1254-1268.

Deswai et al. "Cytokines and Cytokine Receptors in Advanced Heart Failure An Analysis of the Cytokine Database from the Vesnarinone Trial (VEST)," *Circulation.* 2001; 103:2055-2059; ://doi.org/10.1161/01.CIR.103.16.2055.

Matsumori, "Cytokines and Heart Failure: Pathophysiological Roles and Therapeutic Implications," *Heart Failure*, Springer, Tokyo; doi.org/10.1007/978-4-431-68331-5_3.

Blum and Miller "Role of cytokines in heart failure," *American Heart Journal*, Volume 135, Issue 2, February 1998, Pages 181-186; doi.org/10.1016/50002-8703(98) 70080-8.

Ueland et al. "Inflammatory cytokines as biomarkers in heart failure," *Clinica Chimica Acta*, Volume 443, 30 Mar. 2015, Pages 71-77; doi.org/10.1016/j.cca.2014.09.001.

What is claimed is:

1. A device that determines a subject's level of inflammation following organ and/or tissue injury in the subject and then, in response to said determination, is programmed to provide at least one bioelectric signal to tissue of the subject so as to regulate expression of selected protein(s) by the tissue, so as to balance inflammation in the subject for organ and/or tissue healing and recovery in the subject, wherein the device comprises:

sensor(s) for determining the subject's level of inflammation;

a microprocessor that, based upon the subject's level of inflammation, is programmed to provide at least one bioelectric signal in order to balance inflammation in the subject; and electrode(s) for applying bioelectric signal(s) to tissue of the subject, wherein the applied bioelectric signal(s) influence expression of protein(s) in the tissue of the subject to which a bioelectric signal or signals is applied.

2. The device of claim 1, wherein the device is programmed to produce bioelectric signals comprising at least each of the following:

a bioelectric signal of, within 15%, 100 mV, 50 Hz, square wave;

a bioelectric signal of 3 V, 10 Hz, square wave, and/or 20 V, 100 Hz, square wave;

a bioelectric signal of, within 15%, alternating high-frequency and medium-frequency signals, symmetric, biphasic, trapezoid pulses, with 400-μs pulse duration and 1.5/1-s ramp-up/ramp-down duration, respectively, and a bioelectric signal of, within 15%, 3.5 V stimulation in 10 second bursts, one (1) burst every 30 seconds at a frequency of about 50 Hz.

3. A method of using the device of claim 2 to treat a subject with a concussion or other brain injury, the method comprising:

applying the bioelectric signals to the subject's tissue.

4. The device of claim 1, wherein the device is programmed to produce at least one bioelectric signal selected from the group consisting of (a) within 15%, 3 mV with a frequency of about 22 Hz, and a current of about 1 mA, followed by 3 mA;

(b) a biphasic, continuous current of 10 μA at 50 Hz;

(c) 3 mV at 2/100 Hz, alternating frequency, with current of 3 mA, followed by 15 Hz, 1 Gauss EM field, consisting of 5-millisecond bursts with 5-microsecond pulses followed by 200 µs pulse duration at 30 Hz and with current amplitude of 140 mA;

(d) 20 V, 1 Hz with a pulse of 5 ms: and any combination thereof.

5. A method of using the device of claim 4 in a subject to regenerate brain cells in the subject, the method comprising:

generating bioelectric signals from the device to upregulate the expression of a protein in the subject, wherein the protein is selected from the group consisting of insulin-like growth factor 1 ("IGF1"), tumor necrosis factor alpha ("TNF-α"), C—X—C motif chemokine 5 ("CXCL5"), and any combination thereof.

6. The method according to claim 5, further comprising:

separately delivering to the subject stem cells and/or growth factors comprising any combination of IGF1, insulin-like growth factor 1 ("IGF1"), interleukin 6 ("IL-6"), interleukin 10 ("IL-10"), interleukin-1β("IL-1β"), transforming growth factor-β("TGFβ"), TNF-α, CXCL5, and any combination thereof.

7. The device of claim 1, wherein the upregulation of expression of the selected protein(s) in the subject occurs without a diminishing effect over time.

8. A method of treating a subject suffering from a brain concussion or traumatic brain injury ("TBI"), the method comprising:

utilizing the device of claim 1 to treat the subject's brain by applying said bioelectric signal(s) to tissue of the subject.

9. The method according to claim 8, comprising the application of bioelectric protein expression and/or release sequence(s) to the subject comprises:

from about five (5) to about forty (40) minutes, to increase IL-1β, wherein the device then determines and adjusts the bioelectric protein expression signals to the subject's tissue for about five (5) minutes of an IL-1β inhibition shut off signal, and then from about five (5) to forty (40) minutes, a rise in TNF-α, wherein the device then determines and adjusts the bioelectric protein expression signals to the subject's tissue for about five (5) minutes of TNF-α inhibition shut off signal, and then from about five (5) to forty (40) minutes rise in TGFβ, and wherein the device then determines and adjusts the bioelectric protein expression signals to the subject's tissue for about five (5) minutes of a TGFβ inhibition shut off signal, and then about three (3) minutes of a rise in IL-10.

10. A method of using the device of claim 1 to treat a subject having heart failure, the method comprising:

delivering selected bioelectric protein expression and/or release signals to the subject so as to control protein expression and/or release of a protein or proteins selected from the group consisting of tumor necrosis factor alpha ("TNF-α"), vascular endothelial growth factor ("VEGF"), endothelial NOS ("eNOS"), SDF, C—X—C motif chemokine 5 ("CXCL5"), and any combination thereof to aid in the treatment of the subject's heart.

11. The method according to claim 10, further comprising:

separately delivering to the subject a cocktail of regenerative agents comprising any combination of the following: stem cells, endothelial progenitor cells, selected exosomes, selected alkaloids, selected anti-inflammatory agents, nutrient hydrogel, organ specific matrix, selected growth factors, amniotic fluid, placenta fluid, cord blood, and embryonic sourced growth factors and cells.

12. A method of using the device of claim 1 in a subject's tissue to control expression and/or release of a protein, wherein the electrical signal stimulates the production of a protein selected from the group consisting of insulin-like growth factor 1 ("IGF1"), tumor necrosis factor alpha ("TNF-α"), C—X—C motif chemokine 5 ("CXCL5"), and any combination thereof.

13. A method of using the device of claim 1 to achieve a desired result in a subject, wherein the desired result is selected from the group consisting of brain regeneration, cognitive function brain improvement, treatment of brain stroke, treatment of traumatic injury, treatment of eye injury, and ear hearing regeneration.

14. The device of claim 1, wherein the device is programmed to produce bioelectric signals comprising at least each of the following:

a bioelectric signal of, within 15%, a frequency of 50 Hz, square wave;

a bioelectric signal of 10 a frequency of Hz, square wave, and/or a frequency of 100 Hz, square wave;

a bioelectric signal of, within 15%, alternating high-frequency and medium-frequency signals, symmetric, biphasic, trapezoid pulses, with 400-µs pulse duration and 1.5/1-s ramp-up/ramp-down duration, respectively, and a bioelectric signal of one (1) burst every 30 seconds at a frequency of about 50 Hz.

15. The device of claim 1, wherein the device is programmed to produce at least one bioelectric signal selected from the group consisting of (a) within 15%, a frequency of about 22 Hz;

(b) a biphasic, continuous current at a frequency of 50 Hz;

(c) a frequency of 2/100 Hz, alternating frequency, followed by a frequency of 15 Hz, 1 Gauss EM field, consisting of 5-millisecond bursts with 5-microsecond pulses followed by a frequency of 30 Hz and 200 µs pulse duration;

(d) a frequency of 1 Hz with a pulse of 5 ms: and (e) any combination thereof.

* * * * *